United States Patent
Goto et al.

(10) Patent No.: US 9,523,036 B2
(45) Date of Patent: Dec. 20, 2016

(54) PHENOLIC COMPOUND HAVING CARBONYL AS NEIGHBORING GROUP AND APPLICATION THEREOF

(71) Applicants: Mayumi Goto, Ichihara (JP); Yasuyuki Sasada, Ichihara (JP)

(72) Inventors: Mayumi Goto, Ichihara (JP); Yasuyuki Sasada, Ichihara (JP)

(73) Assignees: JNC CORPORATION, Tokyo (JP); JNC PETROCHEMICAL CORPORATION, Tokyo (JP)

( * ) Notice: Subject to any disclaimer, the term of this patent is extended or adjusted under 35 U.S.C. 154(b) by 0 days.

(21) Appl. No.: 13/896,603

(22) Filed: May 17, 2013

(65) Prior Publication Data
US 2013/0306909 A1  Nov. 21, 2013

(30) Foreign Application Priority Data

May 18, 2012  (JP) ................................. 2012-114318

(51) Int. Cl.
| | | |
|---|---|---|
| C07C 49/225 | (2006.01) | |
| C07C 49/825 | (2006.01) | |
| C09K 19/06 | (2006.01) | |
| C09K 19/20 | (2006.01) | |
| C09K 19/30 | (2006.01) | |
| C09K 19/04 | (2006.01) | |
| C09K 19/34 | (2006.01) | |

(52) U.S. Cl.
CPC ......... *C09K 19/3003* (2013.01); *C07C 49/825* (2013.01); *C09K 19/06* (2013.01); *C09K 19/062* (2013.01); *C09K 19/20* (2013.01); *C09K 19/3066* (2013.01); *C09K 19/3098* (2013.01); *C07C 49/225* (2013.01); *C09K 2019/0444* (2013.01); *C09K 2019/0466* (2013.01); *C09K 2019/3422* (2013.01)

(58) Field of Classification Search
CPC ... C07C 49/225; C07C 49/825; C09K 19/062; C09K 19/3066; C09K 2019/0444
See application file for complete search history.

(56) References Cited

U.S. PATENT DOCUMENTS

| | | | |
|---|---|---|---|
| 6,177,152 B1 * | 1/2001 | Terada et al. .................. | 428/1.1 |
| 2007/0225290 A1 * | 9/2007 | Berger et al. ................. | 514/248 |
| 2008/0312316 A1 * | 12/2008 | Culshaw et al. .............. | 514/456 |
| 2011/0309300 A1 * | 12/2011 | Masukawa et al. ..... | 252/299.61 |

FOREIGN PATENT DOCUMENTS

EP   1818384 A1   8/2007

OTHER PUBLICATIONS

Cube et al., A Brain Penetrant Allosteric Potentiator at the Metabotropic Glutamate Receptor 2(mGluR2), Mar. 28, 2005, Bioorganic and Medicinal Chemistry Letters, 15, 2389-2393.*
Ahluwalia et al., A Convenient Synthesis of Psoralen Derivatives Oxygenated in the Pyrone Ring, 1979, Australian Journal of Chemistry, 32, 1361-1367.*

* cited by examiner

Primary Examiner — Cynthia H Kelly
Assistant Examiner — Anna Malloy
(74) Attorney, Agent, or Firm — Hogan Lovells US LLP

(57) ABSTRACT

To provide a liquid crystal compound having a large negative value of dielectric anisotropy ($\Delta\epsilon$). A compound is represented by formula (1):

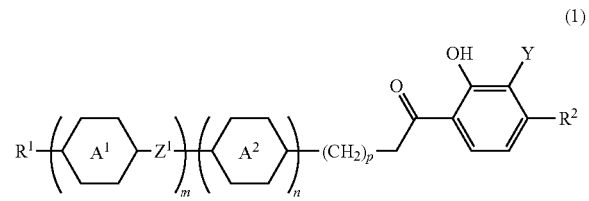

wherein, in formula (1), $R^1$ and $R^2$ are hydrogen, halogen or alkyl having 1 to 10 carbons, and in the alkyl, at least one of —$CH_2$— may be replaced by —O—, at least one of —$(CH_2)_2$— may be replaced by —CH=CH—, and at least one of hydrogen may be replaced by halogen; ring $A^1$ and ring $A^2$ are 1,4-cyclohexylene or 1,4-phenylene; $Z^1$ is a single bond, —$(CH_2)_2$—, —$CH_2O$—, —$OCH_2$—, —$CF_2O$—, —$OCF_2$—, —COO—, or —OCO—; Y is halogen, —$CF_3$, —$CF_2H$ or —$CH_2F$; and m, n and p are 0, 1 or 2, and a sum (m+n) of m and n is 0, 1 or 2.

10 Claims, No Drawings

PHENOLIC COMPOUND HAVING CARBONYL AS NEIGHBORING GROUP AND APPLICATION THEREOF

This is a Non-Provisional application, which claims priority to Japanese Patent Application No. 2012-114318, filed on May 18, 2012; the contents of which are all herein incorporated by this reference in their entireties. All publications, patents, patent applications, databases and other references cited in this application, all related applications referenced herein, and all references cited therein, are incorporated by reference in their entirety as if restated here in full and as if each individual publication, patent, patent application, database or other reference were specifically and individually indicated to be incorporated by reference.

TECHNICAL FIELD

The invention relates to a new liquid crystal compound, liquid crystal composition and liquid crystal display device. More specifically, the invention relates to a liquid crystal compound that has a carbonyl group as a neighboring group and has a negative value of dielectric anisotropy ($\Delta\epsilon$), a liquid crystal composition containing the compound and a liquid crystal display device including the liquid crystal composition.

BACKGROUND ART

A liquid crystal display device is widely utilized for a display of a personal computer, a television and so forth. The device utilizes optical anisotropy and dielectric anisotropy of a liquid crystal compound. As an operating mode of the liquid crystal display device, various modes are known, such as a phase change (PC) mode, a twisted nematic (TN) mode, a super twisted nematic (STN) mode, a bistable twisted nematic (BTN) mode, an electrically controlled birefringence (ECB) mode, an optically compensated bend (OCB) mode, an in-plane switching (IPS) mode, a vertical alignment (VA) mode and a polymer sustained alignment (PSA) mode.

Among the modes, the ECB mode, the IPS mode, the VA mode and so forth are based on the operating mode utilizing vertical alignment of liquid crystal molecules. In particular, the IPS mode and the VA mode are known to have capability of improving narrowness of viewing angle being a disadvantage of the operating mode such as the TN mode and the STN mode.

In a liquid crystal display device to be operated according to the IPS mode and the VA mode, a liquid crystal composition having a negative dielectric anisotropy is mainly used. In order to further improve characteristics of the device, the liquid crystal compound contained in the liquid crystal composition preferably has physical properties as shown in (1) to (8):

(1) high stability to heat, light and so forth;
(2) high clearing point;
(3) low minimum temperature of a liquid crystal phase;
(4) small viscosity ($\eta$);
(5) suitable value of optical anisotropy ($\Delta n$);
(6) large negative value of dielectric anisotropy ($\Delta\epsilon$);
(7) suitable elastic constant ($K_{33}$: bend elastic constant); and
(8) excellent solubility in other liquid crystal compounds.

An effect of the physical properties of the liquid crystal compound on the characteristics of the device is as described below.

A compound having a high stability to heat, light and so forth as described in (1) increases a voltage holding ratio of the device. Thus, a service life of the device becomes long. A compound having a high clearing point as described in (2) extends a temperature range in which the device can be used. A compound having a low minimum temperature of the liquid crystal phase such as a nematic phase or a smectic phase as described in (3), particularly, a compound having a low minimum temperature of the nematic phase, also extends the temperature range in which the device can be used. A compound having a small viscosity as described in (4) shortens a response time of the device.

A compound having a suitable optical anisotropy as described in (5) improves a contrast of the device. According to a design of the device, a compound having a large optical anisotropy or small optical anisotropy, more specifically, a compound having a suitable optical anisotropy is required. When a response time is shortened by decreasing a cell gap of the device, a compound having a large optical anisotropy is suitable. A compound having a large dielectric anisotropy as described in (6) decreases a threshold voltage of the device. Thus, an electric power consumption of the device becomes small.

With regard to (7), a compound having a large elastic constant shortens a response time of the device; and a compound having a small elastic constant decreases a threshold voltage of the device. Accordingly, a suitable elastic constant is required according to characteristics to be desirably improved.

A compound having an excellent solubility in other liquid crystal compounds as described in (8) is preferred. The reason is that physical properties of the liquid crystal composition are adjusted by mixing liquid crystal compounds having different physical properties.

Various kinds of liquid crystal compounds having a large dielectric anisotropy have been synthesized so far. The reason is that (i) excellent physical properties that are not developed by a conventional compound are expected for a new compound, and that (ii) a suitable balance between two of arbitrary physical properties of the physical properties required upon preparing the liquid crystal composition is expected for a new compound.

For example, as disclosed in Patent literature No. 1, examples of reports have been found so far for a phenolic compound having a phenolic moiety, and a carbonyl group bonded with a carbon atom in a benzene ring of the phenolic moiety. However, the examples are limited to a compound having a relatively small negative value of dielectric anisotropy.

CITATION LIST

Patent Literature

Patent literature No. 1: JP 2007-217288 A.

SUMMARY OF INVENTION

Technical Problem

An object of the invention is to provide a liquid crystal compound having a large negative value of negative dielectric anisotropy ($\Delta\epsilon$), a liquid crystal composition containing the compound and a liquid crystal display device including the liquid crystal composition.

Solution to Problem

The present inventors have diligently conducted research for achieving the object. As a result, the present inventors have found that a liquid crystal compound having a structure as described below has a large negative value of dielectric anisotropy (Δ∈), and thus have completed the invention.

More specifically, the invention concerns a compound represented by formula (1):

Formula 1

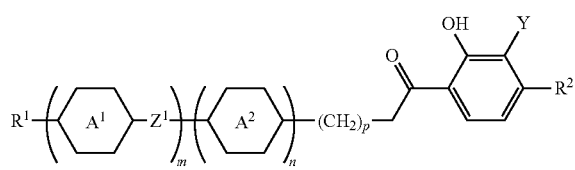
(1)

wherein, in formula (1), $R^1$ and $R^2$ are independently hydrogen, halogen or alkyl having 1 to 10 carbons, and in the alkyl, at least one of —$CH_2$— may be replaced by —O—, at least one of —$(CH_2)_2$— may be replaced by —CH=CH—, and at least one of hydrogen may be replaced by halogen; ring $A^1$ and ring $A^2$ are independently 1,4-cyclohexylene or 1,4-phenylene, at least one of —$(CH_2)_2$— constituting 1,4-cyclohexylene may be replaced by —CH=CH—, at least one of Formula 2

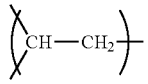

constituting 1,4-cyclohexylene may be replaced by

Formula 3

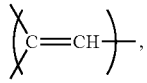

at least one of —$CH_2$— constituting 1,4-cyclohexylene may be replaced by —O— or —CO—, and at least one of hydrogen directly bonded with the rings may be replaced by halogen, —$CF_3$, —$CF_2H$ or —$CH_2F$; $Z^2$ is a single bond, —$(CH_2)_2$—, —$CH_2O$—, —$OCH_2$—, —$CF_2O$—, —$OCF_2$—, —COO— or —OCO—; Y is halogen, —$CF_3$, —$CF_2H$ or —$CH_2F$; and m, n and p are independently 0, 1 or 2, and a sum (m+n) of m and n is 0, 1 or 2.

In formula (1), $R^1$ and $R^2$ are independently hydrogen, alkyl having 1 to 10 carbons, alkenyl having 2 to 10 carbons, alkoxy having 1 to 9 carbons, alkoxyalkyl having 2 to 9 carbons or alkenyloxy having 2 to 9 carbons, and in the groups, at least one of hydrogen may be replaced by halogen; and ring $A^1$ and ring $A^2$ are independently preferably 1,4-cyclohexylene, 1,4-cyclohexenylene, tetrahydropyran-2,5-diyl, 1,4-phenylene, 2-fluoro-1,4-phenylene or 2,3-difluoro-1,4-phenylene.

In formula (1), Y is preferable fluorine. In formula (1), preferably, a relational expression: m=n=1 applies, a relational expression: m=0 and n=1 applies, or a relational expression: m=n=p=0 applies.

The invention also concerns use of the compound represented by formula (1) as a component of a liquid crystal composition. The invention further concerns a liquid crystal composition containing at least one kind of compound represented by formula (1), in which the liquid crystal composition preferably further contains at least one kind selected from an optically active compound and a polymerizable compound, or preferably further contains at least one kind selected from an antioxidant and an ultraviolet absorber. The invention still further concerns a liquid crystal display device including the liquid crystal composition.

Advantageous Effects of Invention

The invention provides a liquid crystal compound having a large negative value of negative dielectric anisotropy (Δ∈), a liquid crystal composition containing the compound and a liquid crystal display device including the liquid crystal composition.

DESCRIPTION OF EMBODIMENTS

Hereinafter, a liquid crystal compound having a large negative value of negative dielectric anisotropy (Δ∈), a liquid crystal composition containing the compound and a liquid crystal display device including the liquid crystal composition according to the invention will be explained with showing specific examples.

Usage of terms herein is as described below.

"Liquid crystal compound" is a generic term for a compound having a liquid crystal phase such as a nematic phase or a smectic phase, and a compound having no liquid crystal phase but being useful as a component of the liquid crystal composition.

"Liquid crystal display device" is a generic term for a liquid crystal display panel and a liquid crystal display module.

"Liquid crystal display device" may be occasionally abbreviated as "display device" or "device."

"Clearing point" is one of values of physical properties measured using the liquid crystal compound per se as a sample, and is a phase transition temperature between the liquid crystal phase (examples: a nematic phase or smectic phase) and an isotropic phase in the liquid crystal compound.

"Minimum temperature of the liquid crystal phase" is one of values of physical properties measured using the liquid crystal compound per se as a sample, and is a phase transition temperature between a crystal phase and the liquid crystal phase (examples: a nematic phase or smectic phase) in the liquid crystal compound.

"Maximum temperature of the nematic phase" is a phase transition temperature between the nematic phase and the isotropic phase in the liquid crystal composition, or a phase transition temperature between the nematic phase and the isotropic phase (in the liquid crystal compound) as calculated according to an extrapolation method from a measured value of a mixture of the liquid crystal compound and a base liquid crystal, and may be occasionally abbreviated as "maximum temperature."

"Minimum temperature of the nematic phase" is a phase transition temperature between the nematic phase and the crystal phase or between the nematic phase and the smectic phase in the liquid crystal composition, or a phase transition temperature between the nematic phase and the crystal phase or between the nematic phase and the smectic phase (in the liquid crystal compound) as calculated according to an extrapolation method from a measured value of a mixture of the liquid crystal compound and a base liquid crystal, and may be occasionally abbreviated as "minimum temperature."

A compound represented by formula (i) (symbol (i) represents the formula number) may be occasionally abbreviated as "compound (i)." In the explanation of formula (1), ring $A^1$ to ring $A^3$ are generically referred to simply as "ring A." In the explanation of each formula, a symbol such $A^1$, $B^1$ and $C^1$ surrounded by a hexagonal shape corresponds to ring $A^1$, ring $B^1$, ring $C^1$ or the like, respectively.

In the explanation of each formula, "halogen" is preferably fluorine or chlorine.

In the explanation of each formula, an expression "at least one of "A" may be replaced by "B"" means that, when the number of "A" is one, a position of "A" is arbitrary, and also when the number of "A" is two or more, positions thereof can be selected without limitation.

For example, an expression "at least one of "A" may be replaced by "B," "C" or "D"" includes a case where arbitrary "A" is replaced by "B," a case where arbitrary "A" is replaced by "C," a case where arbitrary "A" is replaced by "D," and also a case where a plurality of "A" are replaced by at least two of "B," "C" and "D."

Specifically, "alkyl in which at least one of —$CH_2$— may be replaced by —O—, and at least one of —$(CH_2)_2$— may be replaced by —CH=CH—" includes alkyl, alkoxy, alkoxyalkyl, alkenyl, alkenyloxy, alkoxyalkenyl and alkenyloxyalkyl.

In addition, in consideration of stability of the compound, replacement of two successive —$CH_2$— in alkyl or the like by —O— to form —O—O— or the like is not preferred. Moreover, replacement of —$CH_2$— in a terminal methyl part (—$CH_2$—H) in alkyl or the like by —O— to form —O—H is not preferred, either.

In the explanation of formula (1), 2-fluoro-1,4-phenylene means two divalent groups as described below. More specifically, 2-fluoro-1,4-phenylene may have any direction.

Formula 4

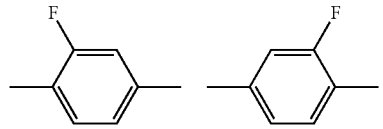

For example, when ring $A^1$ is 2-fluoro-1,4-phenylene, formula (1) may be any of (a) and (b) as described below. In the explanation of ring $A^1$ to ring $A^2$ in formula (1), ring $B^1$ to $B^4$ in formulas (2) to (7) as described later, and ring $C^1$ to ring $C^3$ in formulas (8) to (10) as described later, the rule is also applied to a left-right asymmetrical divalent group such as 2,3-difluoro-1,4-phenylene and tetrahydropyran-2,5-diyl.

Formula 5

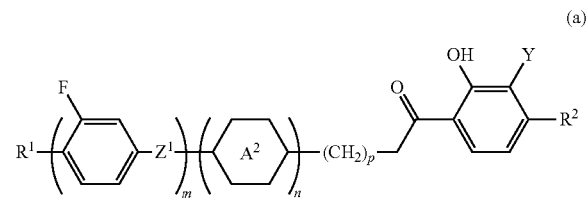

(a)

-continued

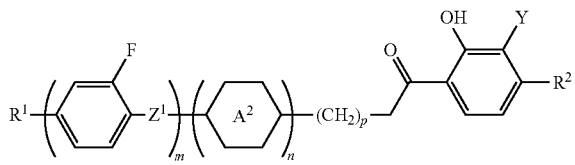

(b)

1. Liquid Crystal Compound
1-1. Structure of Liquid Crystal Compound

The liquid crystal compound of the invention is represented by formula (1).

Formula 6

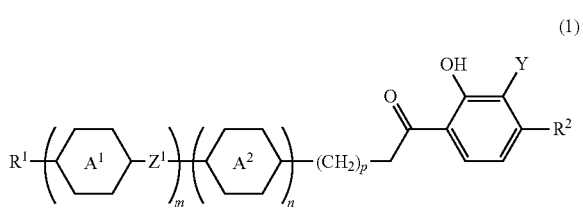

(1)

Hereinafter, terminal groups $R^1$ and $R^2$, ring $A^1$ and ring $A^2$, bonding group $Z^1$, substituent Y on a benzene ring and the number of repetition m, n, and p in formula (1) will be explained. Compound (1) may contain isotopes such as $^2H$ (deuterium) and $^{13}C$ in an amount higher than an amount of natural abundance because compound (1) has no large difference in the physical properties.

Terminal Groups $R^1$ and $R^2$

In formula (1), $R^1$ and $R^2$ are independently hydrogen, halogen or alkyl having 1 to 10 carbons. In the alkyl, at least one of —$CH_2$— may be replaced by —O—, at least one of —$(CH_2)_2$— may be replaced by —CH=CH—, and at least one of hydrogen may be replaced by halogen. Hereinafter, a group in which the replacement is made in the alkyl is also referred to as "substituted alkyl."

Specific examples of the substituted alkyl include alkoxy, alkoxyalkyl, alkenyl, alkenyloxy, alkoxyalkenyl and alkenyloxyalkyl, and a group in which at least one of hydrogen in alkyl or the group exemplified in the paragraph is replaced by halogen (alkyl halide, alkoxy halide, alkoxyalkyl halide, alkenyl halide, alkenyloxy halide, alkoxyalkenyl halide and alkenyloxyalkyl halide).

The number of carbons of alkyl is ordinarily 1 to 10, preferably, 1 to 5. Specific examples of alkyl include —$CH_3$, —$C_2H_5$, —$C_3H_7$, —$C_4H_9$, —$C_5H_{11}$, —$C_6H_{13}$ and —$C_7H_{15}$, preferably, —$CH_3$, —$C_2H_5$, —$C_3H_7$, —$C_4H_9$ and —$C_5H_{11}$.

The number of carbons of alkoxy is ordinarily 1 to 9, preferably, 1 to 5. Specific examples of alkoxy include —$OCH_3$, —$OC_2H_5$, —$OC_3H_7$, —$OC_4H_9$, —$OC_5H_{11}$ and —$OC_6H_{13}$, preferably, —$OCH_3$, —$OC_2H_5$, —$OC_3H_7$, —$OC_4H_9$ and —$OC_5H_{11}$.

The number of carbons of alkoxyalkyl is ordinarily 2 to 9, preferably, 2 to 5. Specific examples of alkoxyalkyl include —$CH_2OCH_3$, —$CH_2OC_2H_5$, —$CH_2OC_3H_7$, —$(CH_2)_2OCH_3$, —$(CH_2)_2OC_2H_5$, —$(CH_2)_2OC_3H_7$, —$(CH_2)_3OCH_3$, —$(CH_2)_4OCH_3$ and —$(CH_2)_5OCH_3$, preferably, —$CH_2OCH_3$, $(CH_2)_2OCH_3$ and —$(CH_2)_3OCH_3$.

The number of carbons of alkenyl is ordinarily 2 to 10, preferably, 2 to 7. Specific examples of alkenyl include —CH=$CH_2$, —CH=$CHCH_3$, —$CH_2CH$=$CH_2$, —CH═CHC₂H₅, —CH₂CH═CHCH₃, —(CH₂)₂CH═CH₂, —CH═CHC₃H₇, —CH₂CH═CHC₂H₅, —(CH₂)₂CH═CHCH₃, —(CH₂)₃CH═CH₂, —CH═CHC₄H₉, —CH₂CH═CHC₃H₇, —(CH₂)₂CH═CHC₂H₅, —(CH₂)₃CH═CHCH₃, —(CH₂)₂CH═CHC₃H₇, —(CH₂)₃CH═CHC₂H₅ and —(CH₂)₃CH═CHC₃H₇, preferably, —CH₂CH═CH₂, —CH₂CH═CHCH₃, —(CH₂)₂CH═CH₂, —CH₂CH═CHC₂H₅, —(CH₂)₂CH═CHCH₃, —(CH₂)₃CH═CH₂, —(CH₂)₃CH═CHCH₃, —(CH₂)₂CH═CHC₃H₇, —(CH₂)₃CH═CHC₂H₅, —(CH₂)₃CH═CHC₃H₇.

A preferred configuration of —CH═CH— in alkenyl depends on a position of a double bond. A trans configuration is preferred in alkenyl having the double bond in an odd-numbered position, such as —CH═CHCH₃, —CH═CHC₂H₅, —CH═CHC₃H₇, —CH═CHC₄H₉, —(CH₂)₂CH═CH₂, —(CH₂)₂CH═CHCH₃ and —(CH₂)₂CH═CHC₂H₅. A cis configuration is preferred in alkenyl having the double bond in an even-numbered position, such as —CH₂CH═CH₂, —CH₂CH═CHCH₃, —CH₂CH═CHC₂H₅, —CH₂CH═CHC₃H₇ and —(CH₂)₃CH═CH₂. An alkenyl compound having the preferred configuration has a wide temperature range of the liquid crystal phase, a small viscosity and a large elastic constant ($K_{33}$: bend elastic constant).

The number of carbons of alkenyloxy is ordinarily 2 to 9, preferably, 2 to 5. Specific examples of alkenyloxy include —OCH₂CH═CH₂, —OCH₂CH═CHCH₃ and —OCH₂CH═CHC₂H₅.

Alkyl and substituted alkyl as exemplified as $R^1$ or $R^2$ are a straight-chain group or a branched-chain group, and do not include a cyclic group such as cyclohexyl. As alkyl and substituted alkyl, a straight-chain alkyl or substituted alkyl is preferred to a branched-chain alkyl or substituted alkyl.

When $R^1$ or $R^2$ has a straight chain, compound (1) has a wide temperature range of the liquid crystal phase, and a small viscosity. When $R^1$ or $R^2$ has a branched chain, compound (1) has improved solubility in other liquid crystal compounds. A compound in which $R^1$ is an optically active group is useful as a chiral dopant. When the compound is added to the liquid crystal composition, a reverse twisted domain generated in the liquid crystal display device can be prevented. A compound in which $R^1$ is not an optically active group is useful as a component of the liquid crystal composition.

$R^1$ and $R^2$ are independently preferably hydrogen, alkyl, alkoxy, alkoxyalkyl, alkenyl, alkenyloxy, or a group in which at least one of hydrogen in the groups is replaced by halogen; independently further preferably, alkyl, alkoxy, alkoxyalkyl or alkenyl; independently still further preferably, alkyl, alkoxy or alkenyl; and independently particularly preferably, —CH₃, —C₂H₅, —C₃H₇, —OCH₃, —OC₂H₅, —OC₃H₇, —OC₄H₉, —(CH₂)₂CH═CH₂, —(CH₂)₂CH═CHCH₃ and —(CH₂)₂CH═CHC₃H₇.

$R^1$ and $R^2$ are preferably not identical. If $R^1$ and $R^2$ are not identical, compound (1) easily develops the liquid crystal phase, and solubility of compound (1) in the liquid crystal composition tends to increase. Moreover, any one of $R^1$ and $R^2$ is preferably a group other than hydrogen, and both of $R^1$ and $R^2$ are further preferably groups other than hydrogen.

Ring $A^1$ and Ring $A^2$

In formula (1), ring $A^1$ and ring $A^2$ are independently 1,4-cyclohexylene or 1,4-phenylene. At least one of —(CH₂)₂— constituting 1,4-cyclohexylene may be replaced by —CH═CH—, at least one of Formula 7

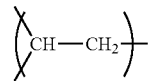

constituting 1,4-cyclohexylene may be replaced by

Formula 8

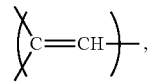

at least one of —CH₂— constituting 1,4-cyclohexylene may be replaced by —O— or —CO—, and at least one of hydrogen directly bonded with the rings may be replaced by halogen, —CF₃, —CF₂H or —CH₂F.

Specific examples of rings in which at least one of —(CH₂)₂— is replaced by —CH═CH— in 1,4-cyclohexylene, groups in which at least one of Formula 9

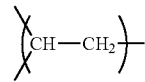

is replaced by

Formula 10

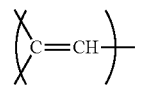

in 1,4-cyclohexylene, and rings in which at least one of —CH₂— is replaced by —O— or —CO— in 1,4-cyclohexylene include preferably rings represented by formula (11-1) to formula (11-8). Among the rings, a ring represented by formula (11-1), formula (11-2), formula (11-7) or formula (11-8) is preferred.

Formula 11

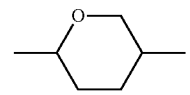 (11-1)

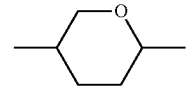 (11-2)

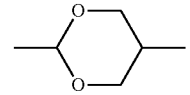 (11-3)

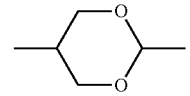 (11-4)

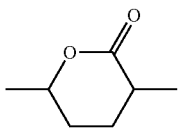 (11-5)

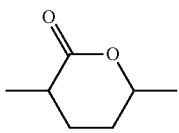 (11-6)

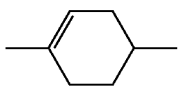 (11-7)

 (11-8)

Specific examples of the rings in which at least one of hydrogen is replaced by halogen, —CF$_3$, —CF$_2$H or —CH$_2$F in the rings include rings represented by formulas (12-1) to (12-18). Among the rings, a ring represented by formula (12-1), formula (12-2), formula (12-3), formula (12-10), formula (12-11), formula (12-12), formula (12-13), formula (12-14) or formula (12-15) is preferred, and a ring represented by formula (12-1), formula (12-2) or formula (12-3) is further preferred.

Formula 12

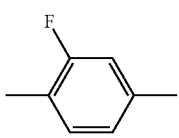 (12-1)

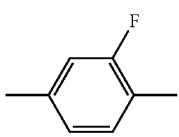 (12-2)

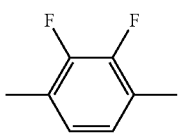 (12-3)

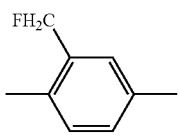 (12-4)

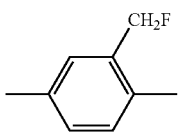 (12-5)

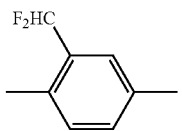 (12-6)

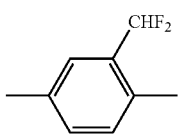 (12-7)

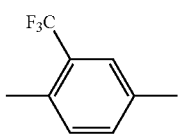 (12-8)

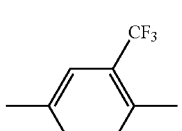 (12-9)

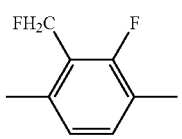 (12-10)

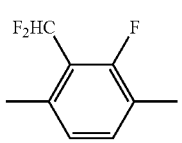 (12-11)

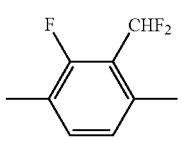 (12-12)

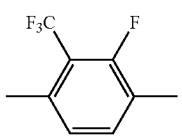 (12-13)

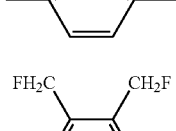 (12-14)

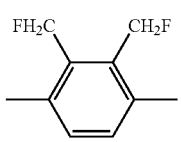 (12-15)

(12-16)

-continued

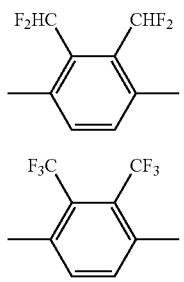

(12-17)

(12-18)

Ring A¹ and ring A² are independently preferably 1,4-cyclohexylene, 1,4-cyclohexenylene, tetrahydropyran-2,5-diyl, 1,4-phenylene, 2-fluoro-1,4-phenylene or 2,3-difluoro-1,4-phenylene; and independently further preferably 1,4-cyclohexylene or 1,4-phenylene. Then, 1,4-cyclohexylene has a cis configuration and a trans configuration. From a viewpoint of a high maximum temperature, a trans configuration is preferred.

When at least one of ring A¹ and ring A² is 1,4-cyclohexylene, compound (1) has a small viscosity. When the compound is added to the liquid crystal composition, the viscosity of the liquid crystal composition can be decreased.

When at least one of ring A¹ and ring A² is 1,4-phenylene, compound (1) tends to have a large optical anisotropy. When the compound is added to the liquid crystal composition, the optical anisotropy of the liquid crystal composition can be increased.

When at least one of ring A¹ and ring A² is 2,3-difluoro-1,4-phenylene, compound (1) has a large negative dielectric anisotropy. When the compound is added to the liquid crystal composition, the dielectric anisotropy of the liquid crystal composition can be negatively increased.

Substituent Y on a Benzene Ring

In formula (1), Y is halogen, —CF₃, —CF₂H or —CH₂F. From a viewpoint of a dipole moment, Y is preferably fluorine, —CF₃ or —CF₂H, and from a viewpoint of narrowing spread of molecules in the minor axis direction, Y is particularly preferably fluorine.

Bonding Group Z¹

In formula (1), Z¹ is a single bond, —(CH₂)₂—, —CH₂O—, —OCH₂—, —CF₂O—, —OCF₂—, —COO— or —OCO—.

A compound in which Z¹ is a single bond is preferred because the viscosity is small. A compound in which Z¹ is —(CH₂)₂—, —CF₂O— or —OCF₂— is preferred because the viscosity is small. A compound in which Z¹ is —CH₂O— or —OCH₂— is preferred because the dielectric anisotropy is negatively large. A compound in which Z¹ is —COO— or —OCO— is preferred because the maximum temperature is high.

When the stability of compound (1) is taken into consideration, Z¹ is preferably a single bond, —(CH₂)₂—, —CH₂O— or —OCH₂—, further preferably, a single bond or —(CH₂)₂—, and particularly preferably a single bond.

Number of Repetitions m, n and p

In formula (1), m, n and p are independently 0, 1 or 2, and a sum (m+n) of m and n is 0, 1 or 2. When a sum of m and n is 0, compound (1) has a small viscosity. When a sum of m and n is 2, compound (1) has a high maximum temperature. When p is 0, compound (1) has a small viscosity. When p is 2, compound (1) tends to have a high clearing point.

1-2. Examples of Suitable Liquid Crystal Compounds

Compound (1) of the invention further preferably include a compound represented by formula (1-1) (in formula (1), a relational expression: m=n=1 applies), a compound represented by formula (1-2) (in formula (1), a relational expression: m=0 and n=1 applies), or a compound represented by formula (1-3) (in formula (1), a relational expression: m=n=p=0 applies).

Formula 13

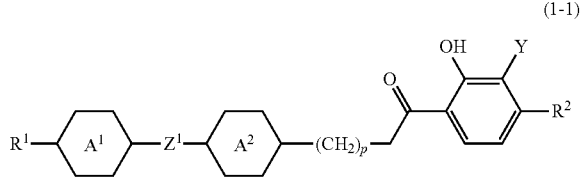

(1-1)

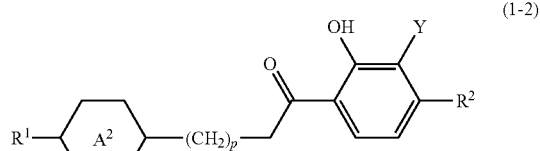

(1-2)

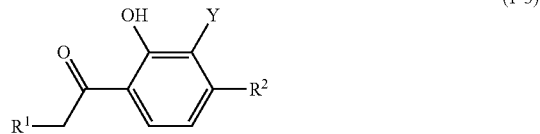

(1-3)

In formula (1-1) to formula (1-3), R¹ and R² are independently hydrogen, alkyl having 1 to 10 carbons, alkenyl having 2 to 10 carbons, alkoxy having 1 to 9 carbons, alkoxyalkyl having 2 to 9 carbons or alkenyloxy having 2 to 9 carbons, and in the groups, at least one of hydrogen may be replaced by halogen; ring A¹ and ring A² are independently 1,4-cyclohexylene, 1,4-cyclohexenylene, tetrahydropyran-2,5-diyl, 1,4-phenylene, 2-fluoro-1,4-phenylene or 2,3-difluoro-1,4-phenylene; and Z¹, Y and p are defined in a manner identical with the definitions of the identical symbols in formula (1). A further preferred embodiment of R¹, R², ring A¹, ring A², Z¹, Y and p is as shown in individual paragraphs in "1-1. Structure of liquid crystal compound."

1-3. Physical Properties of Liquid Crystal Compound

Compound (1) of the invention simultaneously has, in the molecule, a phenolic moiety, a carbonyl group bonded with a carbon atom of a benzene ring of the phenolic moiety, a phenolic hydroxyl group and polar group Y as faced in the minor direction of the molecule. The carbonyl group is bonded with a carbon atom on a 2-position of the benzene ring of the phenolic moiety, and therefore an intramolecular hydrogen bond is formed between an oxygen atom of the carbonyl group, and a hydrogen atom of the phenolic hydroxyl group. As a result, the carbonyl group, the phenolic hydroxyl group and polar group Y are faced in an identical minor axis direction of the molecule. Compound (1) has such a structure, and therefore has a large negative dielectric anisotropy, a suitable optical anisotropy and a suitable elastic constant $K_{33}$.

Moreover, compound (1) of the invention has general physical properties required as the liquid crystal compound, specifically, a high stability to heat and light, a high clearing point and a high maximum temperature, a low minimum temperature of the liquid crystal phase, a small viscosity and excellent solubility in other liquid crystal compounds, and is the liquid crystal compound having an excellent balance of physical properties.

The liquid crystal composition containing compound (1) according to the invention has a high maximum temperature, a low minimum temperature, a small viscosity, a suitable optical anisotropy, a large negative dielectric anisotropy and a suitable elastic constant. The liquid crystal composition is stable under conditions in which the device is ordinarily used. Even if the liquid crystal composition is stored at a low temperature, compound (1) of the invention does not precipitate as a crystal or the smectic phase. Accordingly, compound (1) of the invention can be particularly preferably used as a component of the liquid crystal composition to be used for the liquid crystal display device according to an operating mode such as an IPS mode, a VA mode or a PSA mode.

1-4. Synthesis of Liquid Crystal Compound

A process for synthesizing compound (1) of the invention will be explained. Compound (1) can be prepared by suitably combining methods in synthetic organic chemistry. A method for introducing objective terminal groups $R^1$ and $R^2$, ring $A^1$ and ring $A^2$, and bonding group $Z^1$, or the like into a starting material is described in books such as "Organic Syntheses" (John Wiley & Sons, Inc.), "Organic Reactions" (John Wiley & Sons, Inc.), "Comprehensive Organic Synthesis" (Pergamon Press) and "New Experimental Chemistry Course (Shin Jikken Kagaku Koza in Japanese)" (Maruzen Co., Ltd.).

1-4-1. Formation of Bonding Group $Z^1$ or the Like

An example of a method for forming bonding group $Z^1$ or the like in compound (1) of the invention is shown in a scheme as described below. In the scheme, $MSG^1$ or $MSG^2$ represents a monovalent organic group having at least one ring. A plurality of monovalent organic groups represented by $MSG^1$ or $MSG^2$ may be identical or different. Compounds (1A) to (1E) correspond to compound (1) of the invention.

Formula 14

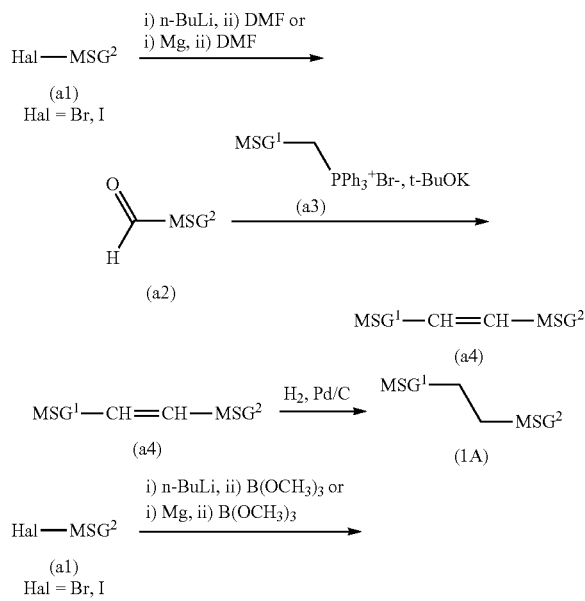

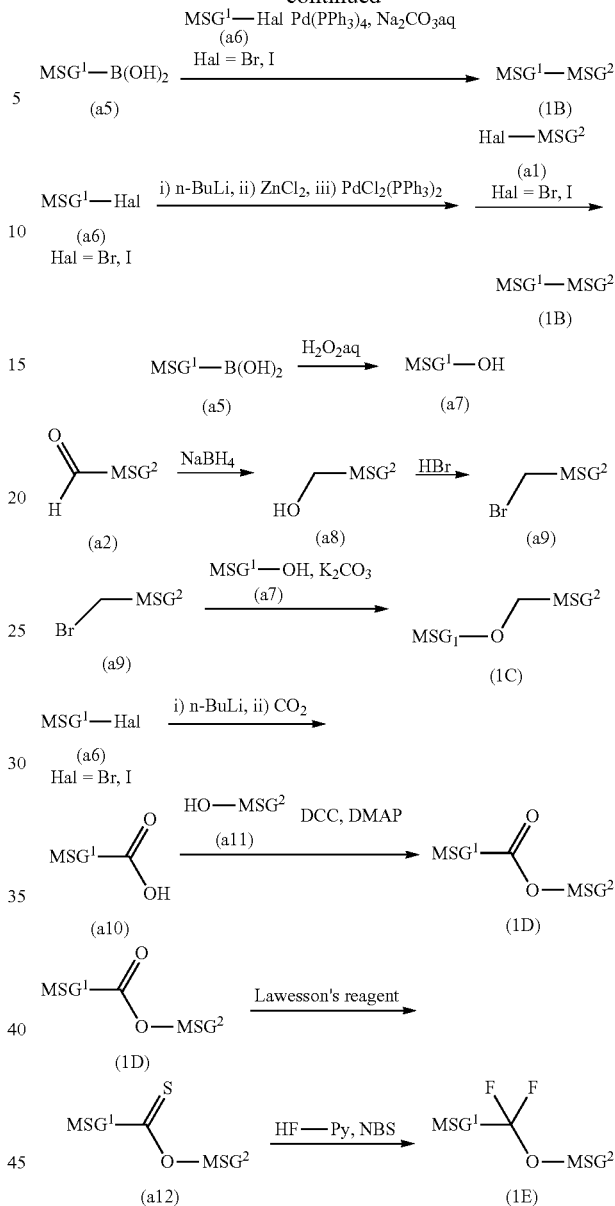

(1) Formation of —(CH$_2$)$_2$—

Aldehyde (a2) is obtained by allowing formamide such as N,N-dimethylformamide (DMF) to react with an intermediate obtained by allowing organohalogen compound (a1) to react with n-butyllithium or magnesium. Compound (a4) having a double bond is obtained by allowing aldehyde (a2) to react with phosphorus ylide obtained by treating phosphonium salt (a3) with a base such as potassium tert-butoxide. Compound (1A) having —(CH$_2$)$_2$— is prepared by hydrogenating compound (a4) in the presence of a catalyst such as palladium on carbon (Pd/C).

(2) Formation of a Single Bond

A lithium salt or a Grignard reagent is prepared by allowing organohalogen compound (a1) to react with n-butyllithium or magnesium. Dihydroxyborane (a5) is obtained by allowing the lithium salt or Grignard reagent to react with a boric acid ester such as trimethyl borate, and then hydrolyzing the resulting reaction product in the presence of acid such as hydrochloric acid. Compound (1B) is prepared by allowing dihydroxyborane (a5) to react, in an aqueous solution of carbonate and in the presence of a catalyst such as tetrakis(triphenylphosphine)palladium (Pd(PPh$_3$)$_4$), with organohalogen compound (a6).

A method as described below can also be applied. Organohalogen compound (a6) is allowed to react with N-butyllithium, and further with zinc chloride. Compound (1B) is prepared by allowing an intermediate obtained to react, in the presence of a catalyst of bistriphenylphosphinedichloropalladium (PdCl$_2$(PPh$_3$)$_2$), with organohalogen compound (a1).

(3) Formation of —CH$_2$O— or —OCH$_2$—

Hydroxyl group-containing compound (a7) is obtained by oxidizing dihydroxyborane (a5) with an oxidizing agent such as hydrogen peroxide. Independently, alcohol (a8) is obtained by reducing aldehyde (a2) with a reducing agent such as sodium borohydride. Halide (a9) is obtained by halogenating alcohol (a8) with hydrobromic acid or the like. Compound (1C) having —CH$_2$O— is prepared by allowing halide (a9) to react, in the presence of potassium carbonate or the like, with hydroxyl group-containing compound (a7) previously obtained. A compound having —OCH$_2$— can also be prepared according to the method.

(4) Formation of —COO— or —OCO—

Carboxylic acid (a10) is obtained by allowing organohalogen compound (a6) to react with n-butyllithium, and subsequently with carbon dioxide. Compound (1D) having —COO— is prepared by dehydrating carboxylic acid (a10) and hydroxy group-containing compound (a11) in the presence of 1,3-dicyclohexylcarbodiimide (DDC) and 4-dimethylaminopyridine (DMAP). A compound having —OCO— can also be prepared according to the method.

(5) Formation of —CF$_2$O— or —OCF$_2$—

Compound (a12) is obtained by treating compound (1D) with a thiation reagent such as Lawesson's reagent. Compound (1E) having —CF$_2$O— is prepared by fluorinating compound (a12) with a hydrogen fluoride-pyridine complex and N-bromosuccinimide (NBS). See M. Kuroboshi et al., Chem. Lett., 1992, 827. Compound (1E) can also be prepared by fluorinating compound (a12) with (diethylamino)sulfurtrifluoride (DAST). See W. H. Bunnelle et al., J. Org. Chem. 1990, 55, 768. A compound having —OCF$_2$— can also be prepared according to the method. The bonding groups can also be formed according to the method described in Peer. Kirsch et al., Angew. Chem. Int. Ed. 2001, 40, 1480.

1-4-2. Synthetic Scheme

An example of a method for synthesizing compound (1) of the invention is shown in a scheme as described below.

Formula 15

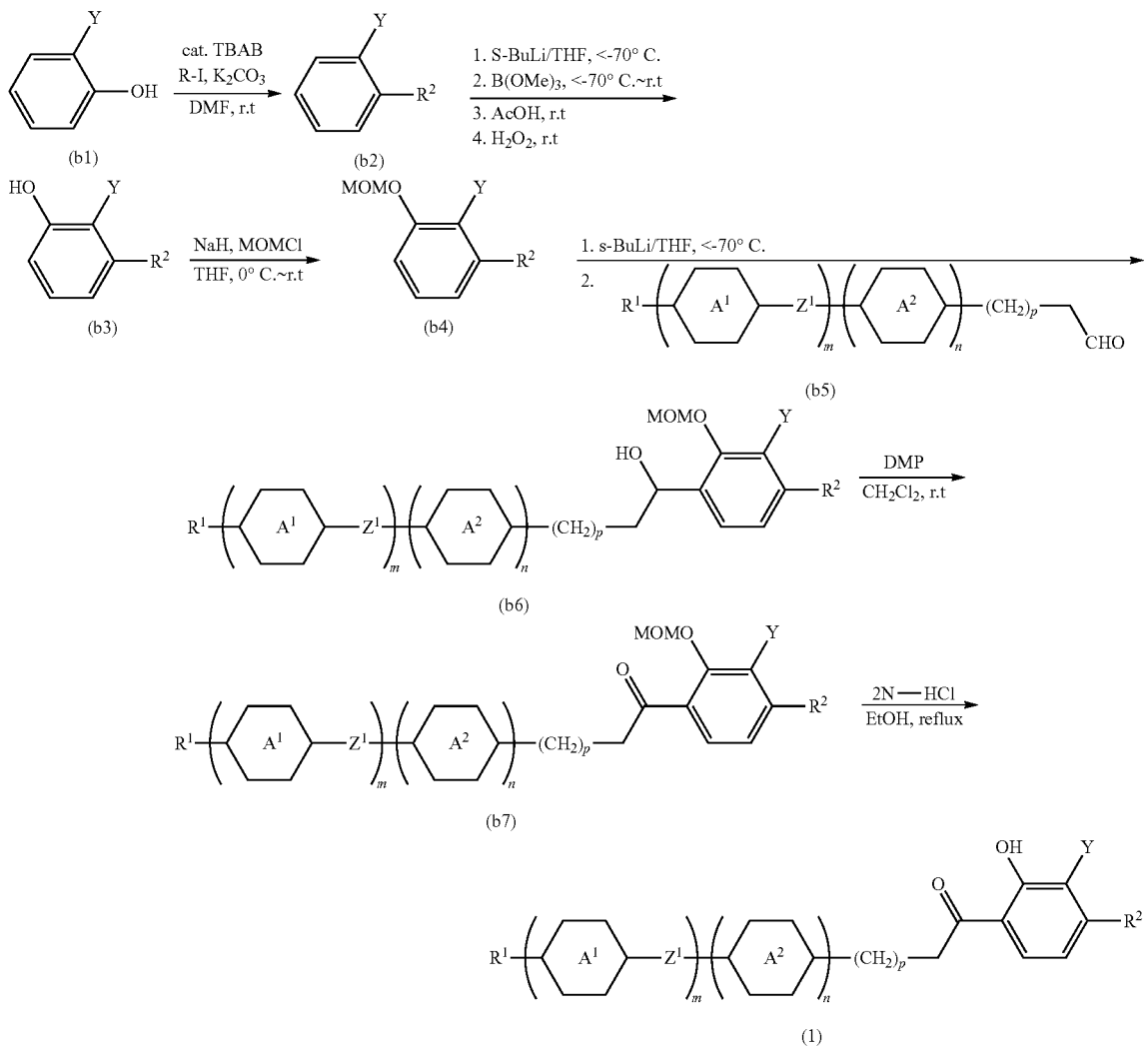

In the scheme, $R^1$, ring $A^1$, ring $A^2$, $Z^1$, Y, m, n and p are defined in a manner identical with the definitions of the identical symbols in formula (1); and $R^2$ is alkoxy.

A method for synthesizing compound (1) of the invention includes, for example, a step for obtaining compound (b2) by treating phenol (b1), in the presence of potassium carbonate and a tetrabutylammonium bromide (TBAB) catalyst at room temperature in an N,N-dimethylformamide solvent, with alkyl iodide, and etherifying the treated product; a step for obtaining phenol (b3) by treating compound (b2), at low temperature of −70° C. or lower in a tetrahydrofuran solvent, with s-butyllithium, and then adding trimethoxyborone to increase temperature to room temperature, and treating the resulting material with acetic acid and hydrogen peroxide; a step for obtaining compound (b4) by protecting a hydroxyl group of phenol (b3) using sodium hydride and chloromethyl methyl ether from 0° C. to room temperature in a tetrahydrofuran solvent; a step for obtaining alcohol (b6) by treating compound (b4), at a low temperature of −70° C. or lower in a tetrahydrofuran solvent, with s-butyllithium, and then allowing the treated product to react with aldehyde (b5); a step for obtaining ketone (b7) by oxidizing alcohol (b6), at room temperature in a dichloromethane solvent, with Dess-Martin periodinane (DMP); and a step for obtaining compound (1) of the invention by removing a protective group of a phenolic hydroxyl group of ketone (b7) using 2 N hydrochloric acid.

Compound (1) of the invention can also be prepared by suitably combining methods in synthetic organic chemistry in a case where, in formula (1), $R^2$ is a group other than alkoxy or in any other cases.

2. Liquid Crystal Composition

The liquid crystal composition of the invention contains compound (1) of the invention as component A. The liquid crystal composition of the invention may contain only one kind of compound (1) or two or more kinds of compound (1). Moreover, the liquid crystal composition of the invention may contain, as components of the liquid crystal composition, two or more kinds of compound (1) only, or compound (1) and various kinds of liquid crystal compounds that are not described herein.

The liquid crystal composition of the invention preferably contains component A in a ratio of approximately 1 to approximately 99% by mass, further preferably, approximately 3 to approximately 60% by mass, particularly preferably, approximately 5 to approximately 20% by mass, based on the total mass of the liquid crystal composition. The content of component A in the range is preferred in view of developing excellent characteristics (examples: a temperature range of the liquid crystal phase, a value of dielectric anisotropy, a value of optical anisotropy, viscosity) of the liquid crystal composition.

The liquid crystal composition of the invention preferably contains at least one kind of component selected from component B and component C. Component B is at least one kind of compound selected from the group of compounds represented by formulas (2) to (7) as described later. Component C is at least one kind of compound selected from the group of compounds represented by formulas (8) to (10) as described later.

The liquid crystal composition of the invention may further contain at least one kind selected from an optically active compound and a polymerizable compound, or at least one kind selected from an antioxidant and an ultraviolet absorber, according to an application.

2-1. Component B (Compounds (2) to (7))

The liquid crystal composition of the invention may contain at least one kind of compound (component B) selected from the group of compounds represented by formulas (2) to (7). Component B has a negative dielectric anisotropy, and has a benzene ring in which lateral positions are replaced by two halogen atoms, such as 2,3-difluoro-1,4-phenylene.

When component B is added to the liquid crystal composition, the elastic constant of the liquid crystal composition can be adjusted, and a voltage-transmittance curve of the device can be adjusted. Component B is used in a case where a liquid crystal composition mainly for application to the IPS mode, the VA mode, the PSA mode or the like.

Formula 16

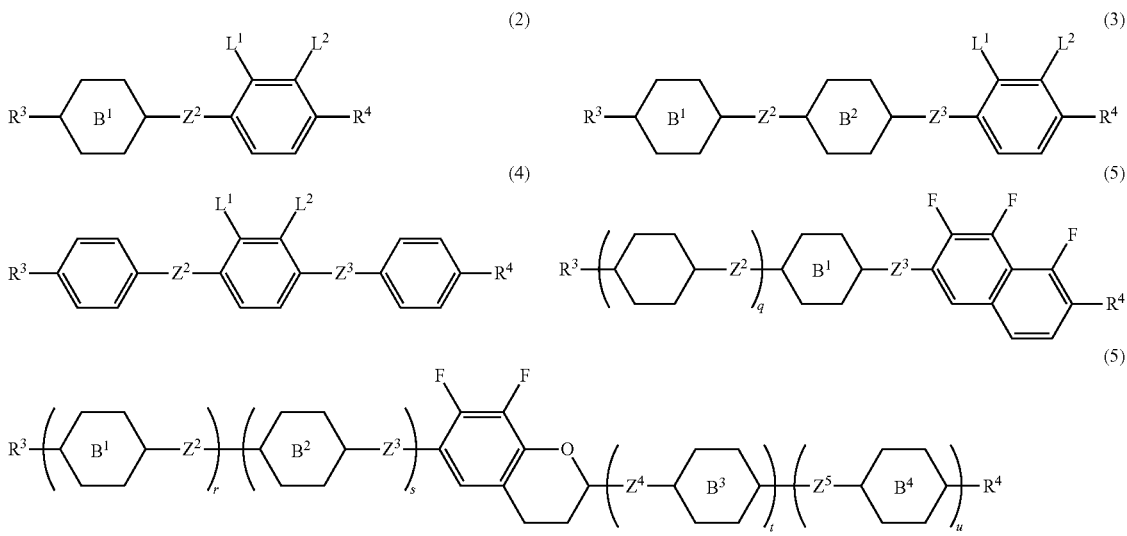

-continued (5)

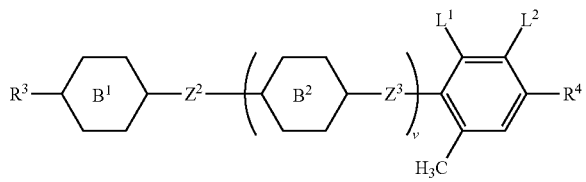

In formulas (2) to (7), a meaning of each symbol is as described below.

$R^3$ and $R^4$ are independently alkyl having 1 to 10 carbons or alkenyl having 2 to 10 carbons, and in the alkyl and the alkenyl, at least one of hydrogen may be replaced by fluorine, and at least one of —$CH_2$— may be replaced by —O—.

Ring $B^1$, ring $B^2$, ring $B^3$ and ring $B^4$ are independently 1,4-cyclohexylene, 1,4-cyclohexenylene, 1,4-phenylene, tetrahydropyran-2,5-diyl or decahydro-2,6-naphthalene, and in the 1,4-phenylene, at least one of hydrogen may be replaced by fluorine.

$Z^2$, $Z^3$, $Z^4$ and $Z^5$ are independently —$(CH_2)_2$—, —COO—, —$CH_2O$—, —$OCF_2$—, —$OCF_2(CH_2)_2$— or a single bond.

$L^1$ and $L^2$ are independently fluorine or chlorine.

Then, q, r, s, t, u and v are independently 0 or 1.

A sum of r, s, t and u is 1 or 2.

Compound (2) is a bicyclic compound, and therefore effective mainly in adjusting the viscosity, the dielectric anisotropy or the optical anisotropy. Compound (3) and compound (4) each is a tricyclic compound, and therefore effective in increasing the maximum temperature, increasing the dielectric anisotropy, increasing the optical anisotropy, or the like. Compounds (5) to (7) each are effective in increasing the dielectric anisotropy, or the like.

If the content of component B is increased, the dielectric anisotropy of the liquid crystal composition increases, but the viscosity increases, and therefore the content is preferably decreased, as long as the requirement for the dielectric anisotropy of the liquid crystal composition is satisfied. However, an absolute value of dielectric anisotropy of component B is approximately 5. Accordingly, in order to allow sufficient voltage driving, the content of component B is preferably in the range of approximately 40% by mass or more, further preferably, in the range of approximately 50 to approximately 95% by mass, based on the total mass of the liquid crystal composition. In the case, content of component A is preferably in the range of approximately 2 to approximately 40% by mass based on the total mass of the liquid crystal composition. The liquid crystal composition having the content of component B in the range is preferred as a liquid crystal composition for application to the IPS mode, the VA mode or the PSA mode, or the like.

On the other hand, when component B is mixed with the liquid crystal composition having a positive value of dielectric anisotropy, the content of component B is preferably in the range of approximately 30% by mass or less, further preferably, in the range of approximately 10% by mass or less, based on the total mass of the liquid crystal composition.

2-2. Component C (Compounds (8) to (10))

The liquid crystal composition of the invention may contain at least one kind of compound (component C) selected from the group of compounds represented by formulas (8) to (10). Component C has alkyl or the like as two terminal groups and has a small absolute value of dielectric anisotropy, and therefore is close to neutrality. When component C is used, the threshold voltage, the temperature range of the liquid crystal phase, the value of dielectric anisotropy, the value of optical anisotropy, the viscosity or the like can be adjusted.

Formula 17

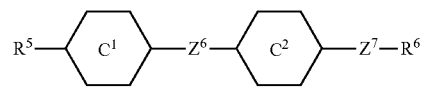

(8)

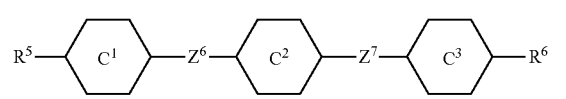

(9)

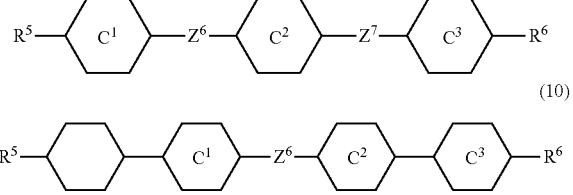

(10)

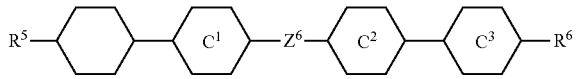

In formulas (8) to (10), a meaning of each symbol is as described below.

$R^5$ and $R^6$ are independently alkyl having 1 to 10 carbons or alkenyl having 2 to 10 carbons, and in the alkyl and the alkenyl, at least one of hydrogen may be replaced by halogen, and at least one of —$CH_2$— may be replaced by —O—.

Ring $C^1$, ring $C^2$ and ring $C^3$ are independently 1,4-cyclohexylene, pyrimidine-2,5-diyl, 1,4-phenylene, 2-fluoro-1,4-phenylene or 2,5-difluoro-1,4-phenylene.

$Z^6$ and $Z^7$ are independently —C≡C—, —COO—, —$(CH_2)_2$—, —CH=CH— or a single bond.

Compound (8) is effective mainly in adjusting the viscosity or the optical anisotropy. Compound (9) and compound (10) each are effective in extending the temperature range of the nematic phase, such as increasing the maximum temperature, or adjusting the optical anisotropy.

If content of component C is increased, the viscosity of the liquid crystal composition decreases, but the dielectric anisotropy of the liquid crystal composition decreases, and therefore the content is preferably increased, as long as the requirement for the dielectric anisotropy of the liquid crystal composition is met.

For example, when preparing a liquid crystal composition for application to the IPS mode, the VA mode or the PSA mode, or the like, the content of component C is preferably in the range of approximately 30% by mass or more, further preferably, in the range of approximately 40% by mass or more, based on the total mass of the liquid crystal composition. In the case, the content of component A is preferably in the range of approximately 1 to approximately 40% by mass based on the total mass of the liquid crystal composition.

2-3. Description of Specific Examples of Component B to Component C
Among types of component B, specific examples of suitable compounds represented by formulas (2) to (7) include compounds represented by formulas (2-1) to (2-6), formulas (3-1) to (3-15), formula (4-1), formulas (5-1) to (5-3), formulas (6-1) to (6-11) and formulas (7-1) to (7-10), respectively.
Formula 18
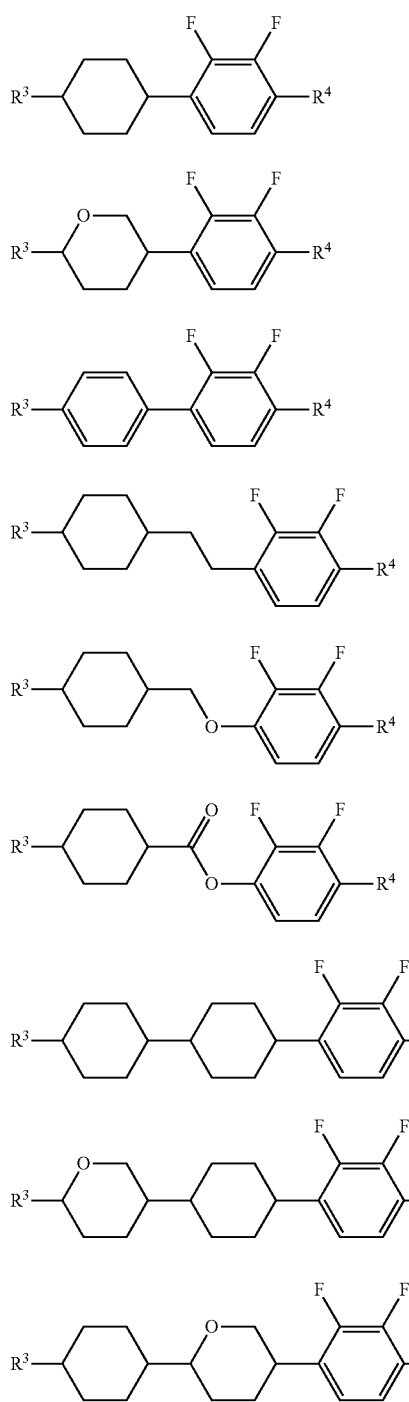
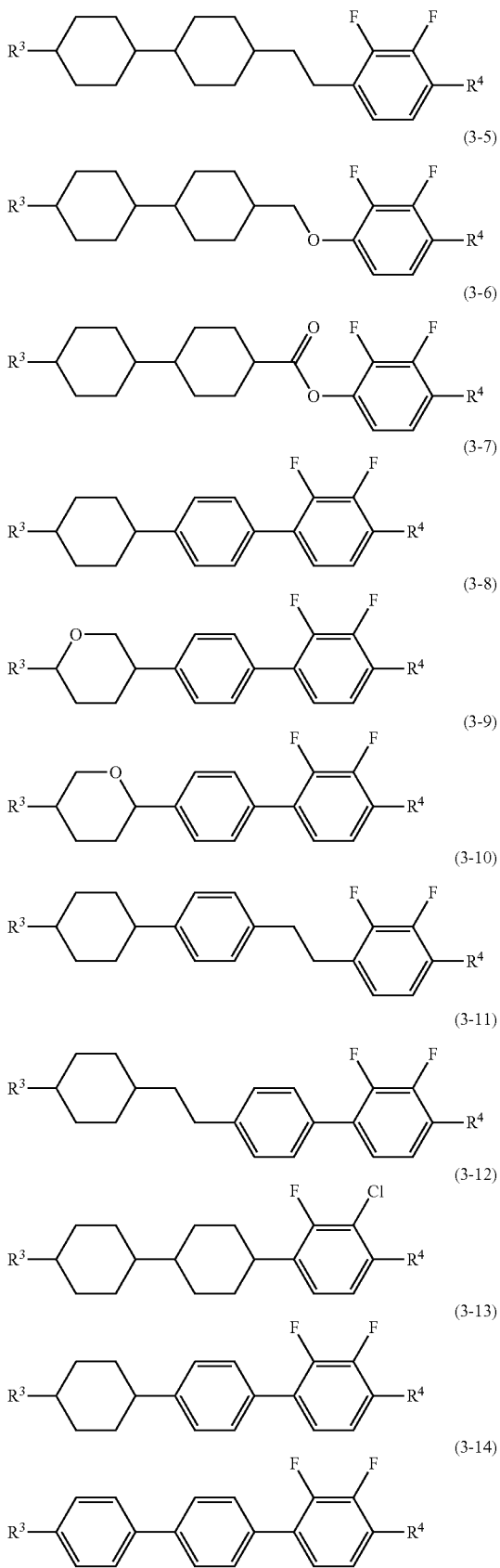

-continued (3-15)

(4-1)

(5-1)

(5-2)

(5-3)

(6-1)

(6-2)

(6-3)

(6-4)

Formula 19

(6-5)

(6-6)

(6-7)

(6-8)

(6-9)

(6-10)

(6-11)

(7-1) 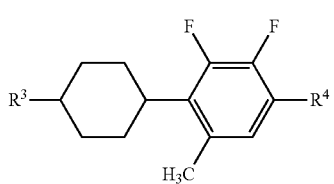
(7-2) 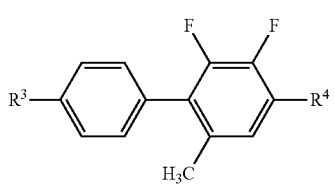
(7-3) 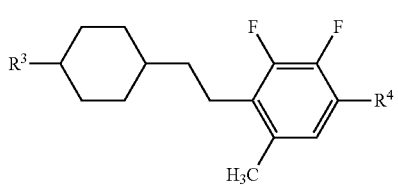
(7-4) 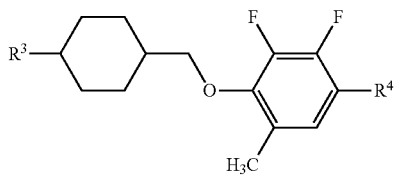
(7-5) 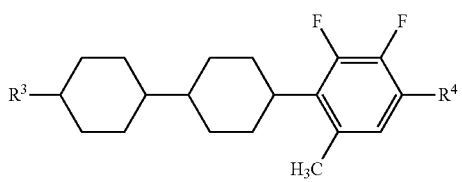
(7-6) 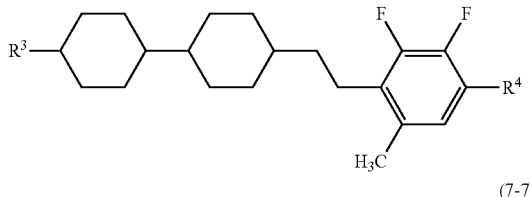
(7-7) 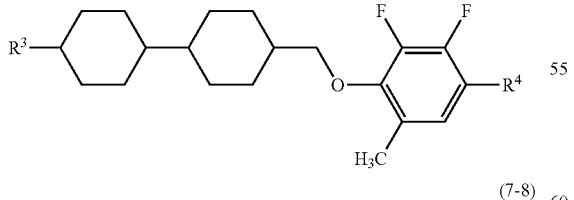
(7-8) 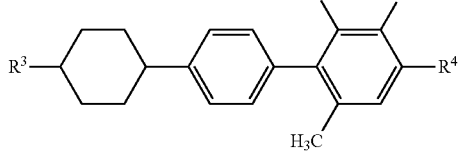
(7-9) 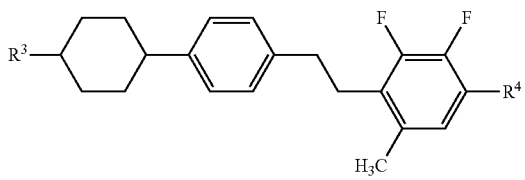
(7-10) 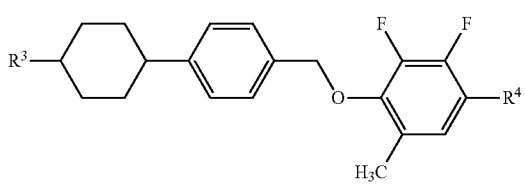
wherein, in the formulas, $R^3$ and $R^4$ are defined in a manner identical with the definitions of the identical symbols in formulas (2) to (7).
Among types of component C, specific examples of suitable compounds represented by formulas (8) to (10) include compounds represented by formulas (8-1) to (8-11), formulas (9-1) to (9-19) and formulas (10-1) to (10-6), respectively.
Formula 20
(8-1) 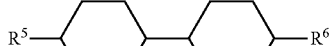
(8-2) 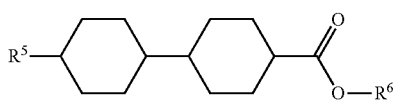
(8-3) 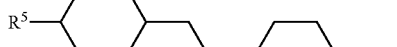
(8-4) 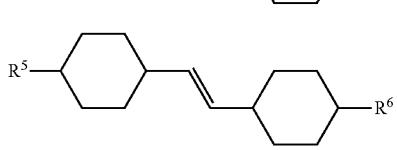
(8-5) 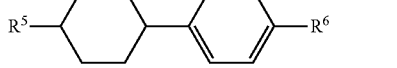
(8-6) 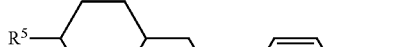
(8-7) 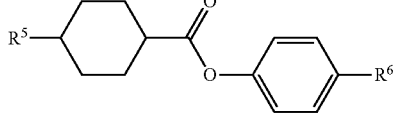

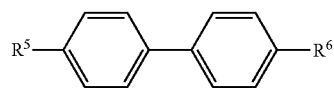 (8-8)
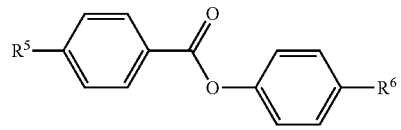 (8-9)
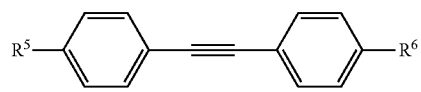 (8-10)
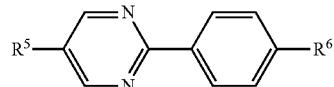 (8-11)
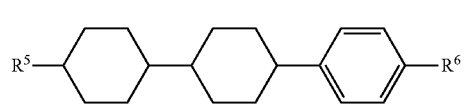 (9-1)
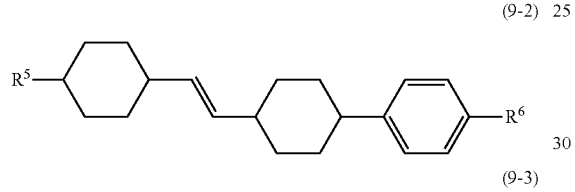 (9-2)
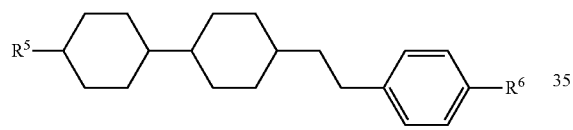 (9-3)
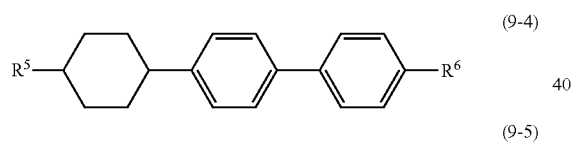 (9-4)
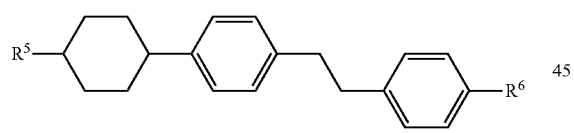 (9-5)
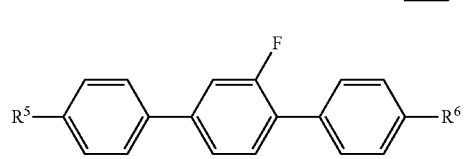 (9-6)
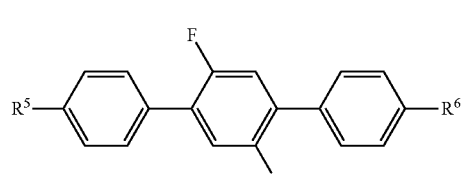 (9-7)
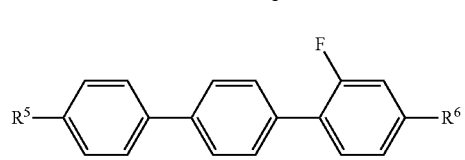 (9-8)
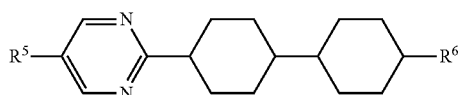 (9-9)
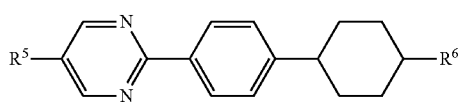 (9-10)
 (9-11)
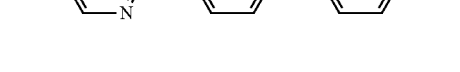 (9-12)
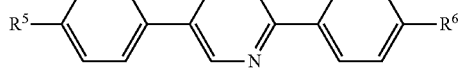 (9-13)
 (9-14)
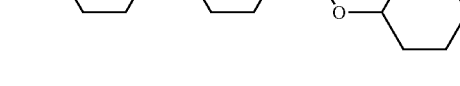 (9-15)
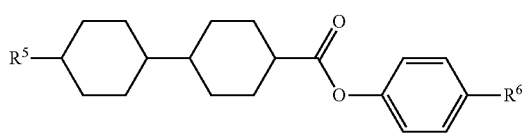 (9-16)
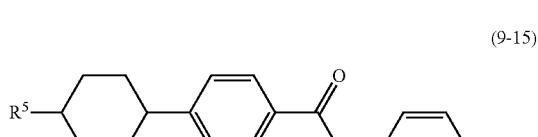 (9-17)
 (9-18)

Formula 21

(9-19)
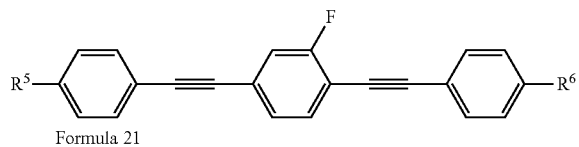

(10-1)
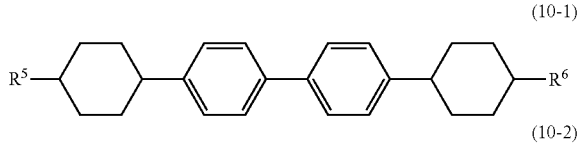

(10-2)
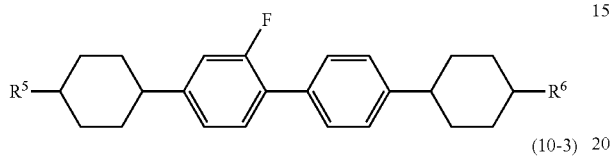

(10-3)
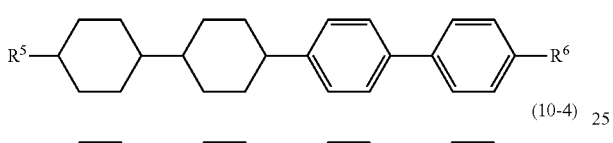

(10-4)
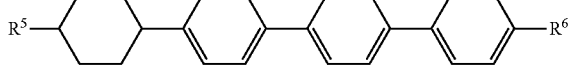

(10-5)
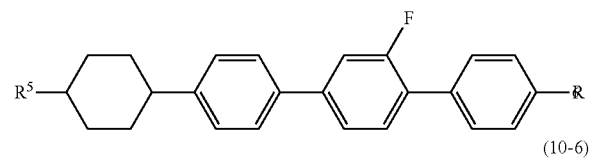

(10-6)
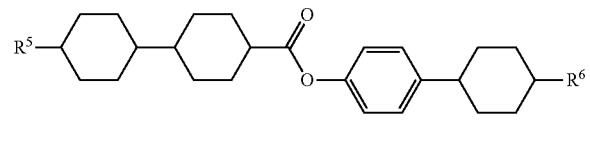

wherein, in the formulas, $R^5$ and $R^6$ are defined in a manner identical with the definitions of the identical symbols in formulas (8) to (10).

2-4. Optically Active Compound

The liquid crystal composition of the invention may contain one kind of optically active compound, or two or more kinds of optically active compounds. Specific examples of the optically active compounds include a publicly known chiral dopant. The chiral dopant is effective in inducing a helical structure of liquid crystals to give a required twist angle, and thus preventing an inverted twist, or the like. Specific examples of the chiral dopants include optically active compounds represented by formulas (Op-1) to (Op-13).

Formula 22

(Op-1)
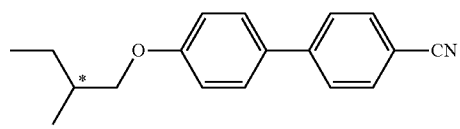

(Op-2)
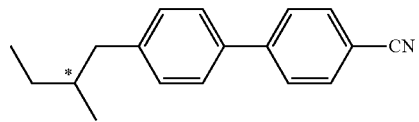

(Op-3)
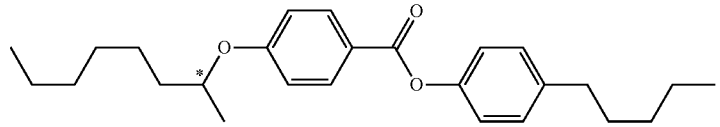

(Op-4)
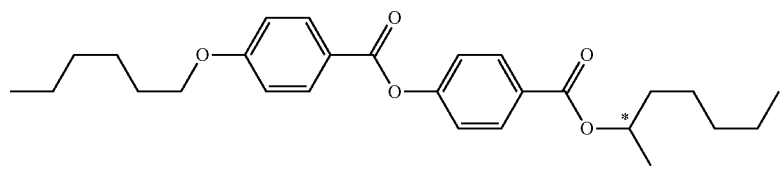

(Op-5)
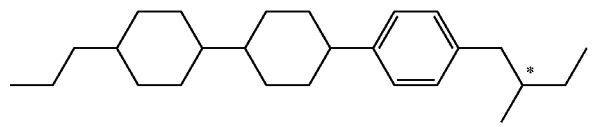

-continued
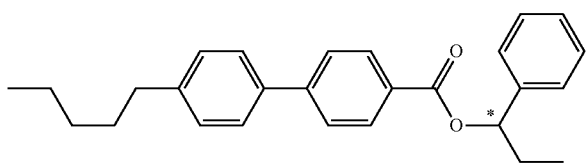
(Op-6)
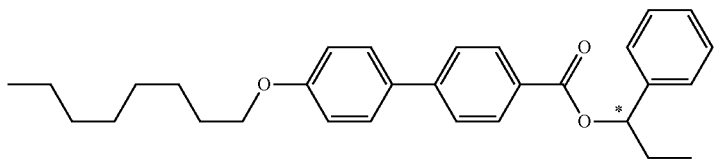
(Op-7)
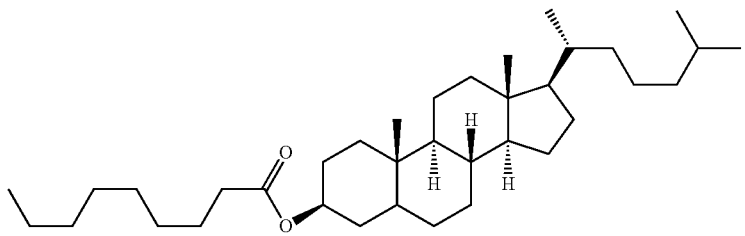
(Op-8)
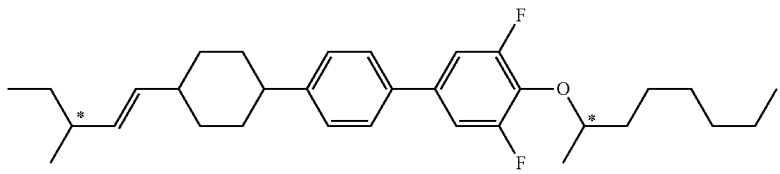
(Op-9)
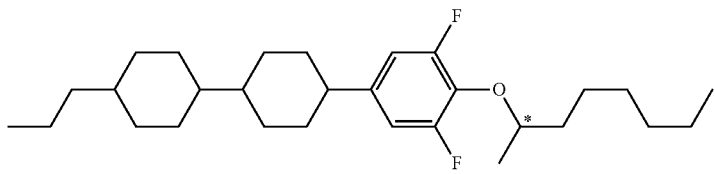
(Op-10)
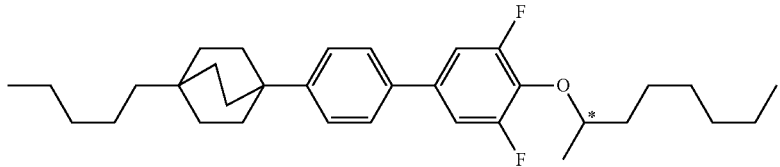
(Op-11)
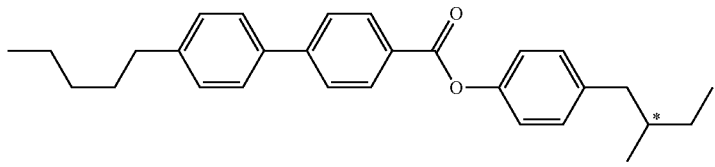
(Op-12)
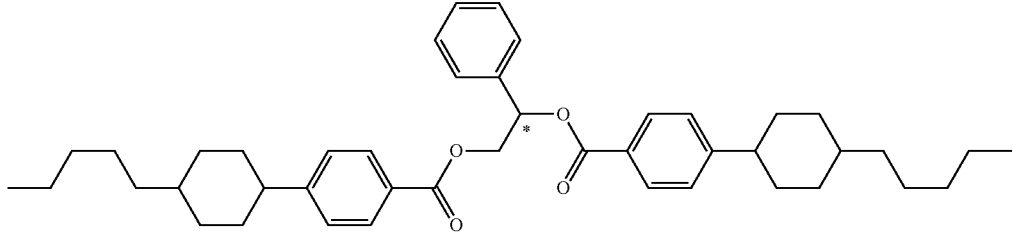
(Op-13)

When the optically active compound is added to the liquid crystal composition of the invention, a helical pitch can be adjusted. The helical pitch is preferably adjusted to the range of approximately 40 to approximately 200 micrometers for a liquid crystal composition for application to the TFT mode and the TN mode; in the range of approximately 6 to approximately 20 micrometers for a liquid crystal composition for application to the STN mode; and in the range of approximately 1.5 to approximately 4 micrometers for a liquid crystal composition for application to the BTN mode. Moreover, two or more kinds of optically active compounds may be added for the purpose of adjusting temperature dependence of the pitch.

2-5. Polymerizable Compound

The liquid crystal composition of the invention can also be used as a liquid crystal composition for application to the PSA mode by adding one kind of polymerizable compound, or two or more kinds of polymerizable compounds (however, excluding a compound corresponding to component A to component C as described above). Moreover, when adding the polymerizable compound, a polymerization initiator is preferably used. In the cases, content of the polymerizable compound is preferably in the range of approximately 0.1 to approximately 2% by mass based on the total mass of the liquid crystal composition.

Specific examples of the polymerizable compounds include a compound having a polymerizable group, such as an acrylate compound, a methacrylate compound, a vinyl compound, a vinyloxy compound, a propenyl ether compound, an oxirane ring-containing compound, an oxetane ring-containing compound and a vinyl ketone compound. The polymerizable compound is preferably polymerized by irradiation with ultraviolet light in the presence of a suitable polymerization initiator such as a photopolymerization initiator.

Suitable conditions for polymerization, suitable types and suitable amounts of the polymerization initiator are known to those skilled in the art and described in each literature. For example, Irgacure 651 (registered tradename; BASF), Irgacure 184 (registered tradename; BASF) or Darocure 1173 (registered tradename; BASF), each being the photopolymerization initiator, are suitable for radical polymerization.

2-6. Antioxidant and Ultraviolet Absorber

The liquid crystal composition of the invention may further contain at least one kind selected from the group of an antioxidant and an ultraviolet absorber. The antioxidant is an effective component to maintain a large voltage holding ratio. Specific examples of the antioxidants include a phenolic antioxidant such as 2,6-di-tert-butyl 4-alkyl phenol. The ultraviolet absorber is an effective component in prevent a decrease of the maximum temperature. Specific examples of the ultraviolet absorbers include a benzophenone derivative, a benzoate derivative and a triazole derivative, and also preferably include a light stabilizer such as an amine having steric hindrance.

2-7. Any Other Component

The liquid crystal composition of the invention can also be used as a liquid crystal composition for application to a guest-host (GH) mode by adding a dye, such as a dichroic dye of a merocyanine type, a styryl type, an azo type, an azomethine type, an azoxy type, a quinophthalone type, an anthraquinone type and a tetrazine type.

2-8. Method for Preparing a Liquid Crystal Composition and Characteristics Thereof When the liquid crystal composition of the invention is prepared, various kinds of compounds can be selected, for example, in consideration of a value of dielectric anisotropy of component A. The liquid crystal composition of the invention has a high maximum temperature, a low minimum temperature, a small viscosity, a large negative dielectric anisotropy, a suitable optical anisotropy and a suitable elastic constant. A term "suitable" herein means that a suitable range of the optical anisotropy and the elastic constant, for example, is appropriately determined according to the operating mode of the liquid crystal display device including the liquid crystal composition of the invention.

In the invention, when a kind and a ratio of components are suitably adjusted, a liquid crystal composition having a maximum temperatures of approximately 70° C. or higher and a minimum temperature of −10° C. or lower, more specifically, a liquid crystal composition having a wide temperature range of the nematic phase can be prepared. Accordingly, the liquid crystal display device including the liquid crystal composition can be used in a wide temperature range.

In the invention, when a kind and a ratio of components are suitably adjusted, a liquid crystal composition having a value of optical anisotropy in the range of approximately 0.10 to approximately 0.13 or in the range of approximately 0.05 to approximately 0.18 can be prepared.

In a similar manner, a liquid crystal composition having a value of dielectric anisotropy ordinarily in the range of approximately −5.0 to approximately −2.0, preferably, in the range of approximately −4.5 to approximately −2.5 can be prepared. The liquid crystal composition having the dielectric anisotropy in the range can be suitably used for the liquid crystal display device to be operated according to the IPS mode, the VA mode or the PSA mode.

The liquid crystal composition is generally prepared by a publicly known method, for example, a method for dissolving required components under a high temperature. Moreover, the liquid crystal compositions for application to various kinds of modes can be prepared by adding an additive well known to those skilled in the art (examples: an optically active compound, a polymerizable compound, a polymerization initiator, an antioxidant, an ultraviolet absorber, a dye). The additive is well known to those skilled in the art, and in addition to the compounds as described above, is described in detail in various kinds of literatures.

3. Liquid Crystal Display Device

The liquid crystal display device of the invention includes the liquid crystal composition of the invention, and has a wide temperature range in which the device can be used, a short response time, a large voltage holding ratio, a large contrast ratio and a long service life.

The liquid crystal composition of the invention can be used for a liquid crystal display device that has the operating mode such as the PC mode, the TN mode, the STN mode, the OCB mode, the IPS mode, the VA mode and the PSA mode, and is driven according to an active matrix (AM) mode. The liquid crystal composition of the invention can also be used for a liquid crystal display device that has the operating mode such as the PC mode, the TN mode, the STN mode, the OCB mode, the IPS mode and the VA mode, and is driven according to a passive matrix (PM) mode. The liquid crystal display device according to the AM mode and the PM mode can be applied to any liquid crystal display of a reflective type, a transmissive type and a transflective type.

The liquid crystal composition of the invention has a negative dielectric anisotropy, and therefore can be preferably used for a liquid crystal display device having the operating mode such as the IPS mode, the VA mode or the PSA mode, and is driven according to the AM mode, particularly preferably, a liquid crystal display device having the VA mode and is driven according to the AM mode.

The liquid crystal composition of the invention can also be used for a nematic curvilinear aligned phase (NCAP) device prepared by microencapsulating nematic liquid crystals, a polymer dispersed liquid crystal display device (PDLCD) prepared by forming a three-dimensional network polymer in the liquid crystals, and a polymer network liquid crystal display device (PNLCD).

In the liquid crystal display device to be operated according to the TN mode, the VA mode or the like, a direction of an electric field is perpendicular to a direction of a liquid crystal layer. On the other hand, in the liquid crystal display device to be operated according to the IPS mode or the like, the direction of the electric field is parallel to the direction of the liquid crystal layer. A structure of the liquid crystal display device to be operated according to the VA mode is reported in K. Ohmuro, S. Kataoka, T. Sasaki and Y. Koike, SID'97 Digest of Technical Papers, 28, 845 (1997). A structure of the liquid crystal display device to be operated according to the IPS mode is reported in WO 91/10936 A.

It will be apparent to those skilled in the art that various modifications and variations can be made in the invention and specific examples provided herein without departing from the spirit or scope of the invention. Thus, it is intended that the invention covers the modifications and variations of this invention that come within the scope of any claims and their equivalents.

The following examples are for illustrative purposes only and are not intended, nor should they be interpreted to, limit the scope of the invention.

EXAMPLES

Hereinafter, the invention will be explained in more detail by way of Examples, but the invention is not limited by the Examples. Unless otherwise noted, "%" in the description of Examples and so forth is expressed in terms of "% by mass."

Methods for measuring physical properties are as described below.

NMR Analysis

As a measuring apparatus, DRX-500 (made by Bruker BioSpin Corporation) was used. A sample was dissolved into a deuterated solvent such as $CDCl_3$, and measurement of $^1H$-NMR was carried out under conditions of room temperature, 500 MHz and 16 times of accumulation. Tetramethylsilane was used as a reference material. Measurement of $^{19}F$-NMR was carried out under conditions of 24 times of accumulation by using $CFCl_3$ as a reference material. In the explanation of nuclear magnetic resonance spectra, s, d, t, q, quin, sex, m, br and dd stand for a singlet, a doublet, a triplet, a quartet, a quintet, a sextet, a multiplet, broad and double doublet, respectively.

Sample for Determining Values of Physical Properties of a Liquid Crystal Compound or the Like A liquid crystal compound per se was used as a sample, and (1) phase structure and (2) phase transition temperature of the liquid crystal compound were measured. A composition prepared by mixing a liquid crystal compound with a base liquid crystal was used as a sample, and values of physical properties of the composition were determined, such as (3) compatibility at a low temperature, (4), (5) a maximum temperature of a nematic phase and a minimum temperature of the nematic phase, (6), (7) viscosity, (8) optical anisotropy, (9) dielectric anisotropy, (10) elastic constant, (11) threshold voltage, and (12), (13) voltage holding ratio.

In the latter case where the composition prepared by mixing the liquid crystal compound with the base liquid crystal was used as the sample, measurement was carried out according to the method described below. First, a sample was prepared by mixing 15% of liquid crystal compound obtained and 85% of base liquid crystal. Extrapolated values were calculated according to an extrapolation method as described below from measured values of the sample obtained, and the extrapolated values were described as values of physical properties of the liquid crystal compound obtained. However, when a smectic phase was maintained at 25° C. or a crystal precipitated at 25° C. even when a mixing ratio of the liquid crystal compound to the base liquid crystal was as described above, a mixing ratio of the liquid crystal compound to the base liquid crystal (liquid crystal compound:base liquid crystal) was changed in the order of (10%:90%), (5%:95%) and (1%:99%), and physical properties were measured at a composition in which no smectic phase was maintained at 25° C. or no crystal precipitated at 25° C., and extrapolated values were determined according to an equation as described below, and the values were described as the values of physical properties. In addition, unless otherwise noted, the mixing ratio of the liquid crystal compound to the base liquid crystal is 15%:85%.

(Extrapolated value)={100×(measured value of a sample)−(% by mass of base liquid crystal)× (measured value of the base liquid crystal)}/(% by mass of liquid crystal compound).   Equation 1

As a base liquid crystal, base liquid crystal A was used for measurement.

Formula 23

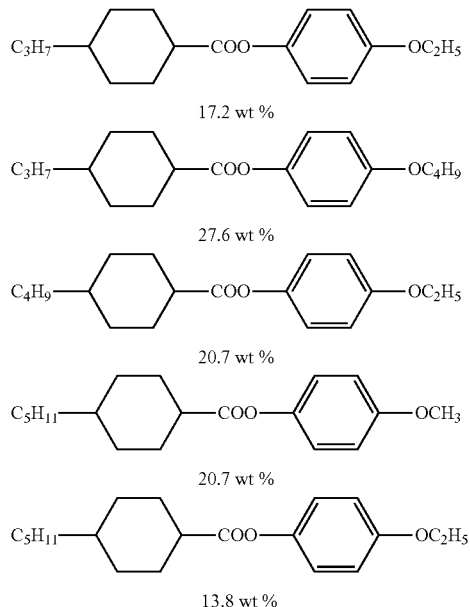

Base liquid crystal A having a nematic phase was prepared by mixing five compounds as described above. Physical properties of base liquid crystal A having the nematic phase (measuring methods were described below) were as described below: maximum temperature $(T_{NI})$=74.6° C., value of dielectric anisotropy $(\Delta\varepsilon)$=−1.3, value of optical anisotropy $(\Delta n)$=0.087. In addition, base liquid crystal A per se was used as a sample for measuring the physical properties.

Method for Measuring Physical Properties of a Liquid Crystal Compound or the Like Physical properties were measured according to the methods described below. Most of the methods were applied as described in JEIAT standard (JEITA ED-2521A) to be discussed and established in Japan Electronics and Information Technology Industries Association (hereinafter, may be referred to also as "JEITA"), or as modified thereon. Moreover, no TFT was attached to a TN device used for measurement.

(1) Phase Structure

A sample (liquid crystal compound) was placed on a hot plate of a melting point apparatus (FP-52 Hot Stage made by Mettler-Toledo International Inc.) equipped with a polarizing microscope, and a state of phase and a change thereof were observed with the polarizing microscope while heating the sample at a rate of 3° C. per minute, and a kind of the phase was specified.

(2) Phase Transition Temperature (° C.)

A sample was heated and then cooled at a rate of 3° C. per minute using a differential scanning calorimeter, DSC-7 System or Diamond DSC System, made by PerkinElmer, Inc. A starting point of an endothermic peak or an exothermic peak caused by a phase change of a sample (liquid crystal compound) was determined by an extrapolation method, and thus a phase transition temperature was determined.

A crystal was expressed as C. When kinds of crystals were distinguishable, each of the crystals was expressed as $C_1$ or $C_2$. Moreover, a smectic phase was expressed as S, and a nematic phase as N. Among the smectic phases, when smectic A phase, smectic B phase, smectic C phase or smectic F phase was distinguishable, each was expressed as $S_A$, $S_B$, $S_C$ or $S_F$. An isotropic liquid (isotropic) was expressed as I. The phase transition temperature was expressed such as "C 50.0 N 100.01," for example. The expression shows that a phase transition temperature from the crystal to the nematic phase is 50.0° C., and a phase transition temperature from the nematic phase to the isotropic liquid is 100.0° C. A same rule applies to other expressions. All units of the phase transition temperature are ° C.

(3) Compatibility at a Low Temperature

Samples were prepared in which base liquid A and a liquid crystal compound were mixed for a mixing ratio of the liquid crystal compound to be 20%, 15%, 10%, 5%, 3% and 1%, and put into glass vials. The glass vials were kept in freezers at −10° C. or −20° C. for a fixed period of time, and then whether or not a crystal (or smectic phase) precipitated was observed.

(4) Maximum Temperature of a Nematic Phase ($T_{NI}$ or NI; ° C.)

A sample (a liquid crystal composition, or a mixture of a liquid crystal compound and a base liquid crystal) was placed on a hot plate of a melting point apparatus (FP-52 Hot Stage made by Mettler-Toledo International Inc.) equipped with a polarizing microscope, and was heated at a rate of 1° C. per minute. Temperature when part of the sample changed from the nematic phase to the isotropic liquid was measured. When the sample was a mixture of the liquid crystal compound and base liquid crystal A, the maximum temperature was expressed using a symbol $T_{NI}$. When the sample was a mixture of the liquid crystal compound and component B or the like, the maximum temperature was expressed using NI. $T_{NI}$ of the liquid crystal compound is an extrapolated value calculated according to the extrapolation method described above, and $T_{NI}$ and NI of the liquid crystal composition are measured values of the mixture per se.

(5) Minimum Temperature of a Nematic Phase ($T_c$; ° C.)

Samples each having a nematic phase were kept in freezers at 0° C., −10° C., −20° C., −30° C. and −40° C. for 10 days, and then liquid crystal phases were observed. For example, when a sample maintained the nematic phase at −20° C. and changed to a crystal or a smectic phase at −30° C., $T_c$ was expressed as $T_c \leq -20°$ C.

(6) Viscosity (Bulk Viscosity; η; Measured at 20° C.; mPa·s)

Viscosity (bulk viscosity) was measured using a cone-plate (E type) rotational viscometer.

(7) Viscosity (Rotational Viscosity; γ1; Measured at 25° C.; mPa·s)

Viscosity (rotational viscosity) was measured according to the method described in M. Imai et al., Molecular Crystals and Liquid Crystals, Vol. 259, p. 37 (1995). A sample was put in a VA device in which a distance (cell gap) between two glass substrates was 20 micrometers. Voltage was stepwise applied to the device in the range of 30 V to 50 V at an increment of 1 V. After a period of 0.2 second with no voltage application, voltage was applied repeatedly under the conditions of only one of rectangular waves (rectangular pulse; 0.2 second) and no voltage application (2 seconds). A peak current and a peak time of a transient current generated by the applied voltage were measured. A value of rotational viscosity was obtained from the measured values and a calculation equation (8) on page 40 of the paper presented by M. Imai et al. A value measured as described below (value of dielectric anisotropy (Δ∈; measured at 25° C.)) was applied as a value of dielectric anisotropy required for the calculation.

(8) Value of Optical Anisotropy (Δn; Measured at 25° C.)

Optical anisotropy was measured by means of Abbe refractometer with a polarizing plate mounted on an ocular by using light at a wavelength of 589 nanometers at a temperature of 25° C. A surface of a main prism was rubbed in one direction, and then a sample (a mixture of the liquid crystal compound and the base liquid crystal) was added dropwise onto the main prism. A refractive index (n∥) was measured when the direction of polarized light was parallel to the direction of rubbing. A refractive index (n( ) was measured when the direction of polarized light was perpendicular to the direction of rubbing. A value of optical anisotropy (Δn) was calculated from an equation: Δn= n((−n(.

(9) Value of Dielectric Anisotropy (Δ∈; Measured at 25° C.)

A value of dielectric anisotropy was calculated from an equation: Δ∈=∈((−∈(.

(1) Measurement of dielectric constant (∈(( ): An ethanol (20 mL) solution of octadecyl triethoxysilane (0.16 mL) was applied onto a well-washed glass substrate. After rotating the glass substrate with a spinner, the glass substrate was heated at 150° C. for 1 hour. A sample was put in a VA device in which a distance (cell gap) was 4 micrometers, and the device was sealed with an ultraviolet-curable adhesive. Sine waves (0.5 V, 1 kHz) were applied to the device, and after two seconds, a dielectric constant (∈(( ) in the minor direction of liquid crystal molecules was measured.

(2) Measurement of dielectric constant (∈⊥): A polyimide solution was applied onto a well-washed glass substrate. After calcining the glass substrate, rubbing treatment was applied to the alignment film obtained. A sample was put in a TN device in which a distance (cell gap) between two glass substrates was 9 micrometers and a twist angle was 80 degrees. Sine waves (0.5 V, 1 kHz) were applied to the device, and after 2 seconds, a dielectric constant (∈⊥) in the minor axis direction of the liquid crystal molecules was measured.

(10) Elastic Constant ($K_{11}$ and $K_{33}$; Measured at 25° C.; pN)

Elastic Constant Measurement System Model EC-1 (made by TOYO Corporation) was used for measurement of an elastic constant. A sample was put in a vertical alignment device in which a distance (cell gap) between two glass substrates was 20 micrometers. A voltage from 20 V to 0 V was applied to the device, and electrostatic capacity and applied voltage were measured. Values of the electrostatic capacity (C) and the applied voltage (V) were fitted to equation (2.98) and equation (2.101) on page 75 of "Liquid Crystal Device Handbook" (Ekisho Debaisu Handobukku in Japanese) (The Nikkan Kogyo Shimbun, Ltd.) and values of elastic constants were obtained from equation (2.100).

(11) Threshold Voltage ($V_{th}$; Measured at 25° C.; V)

An LCD-5100 luminance meter made by Otsuka Electronics Co., Ltd. was used for measurement. A light source was a halogen lamp. A sample was put in a normally black mode VA device in which a distance (cell gap) between two glass substrates was 4 micrometers and a rubbing direction was anti-parallel, and the device was sealed with an ultraviolet-curable adhesive. Voltage (60 Hz, rectangular waves) to be applied to the device was increased stepwise from 0 V to 20 V at an increment of 0.02 V. On the occasion, the device was irradiated with light from a direction perpendicular to the device, and the amount of light transmitted through the device was measured. A voltage-transmittance curve was prepared, in which the maximum amount of light corresponds to 100% transmittance and the minimum amount of light corresponds to 0% transmittance. A threshold voltage is a voltage at 10% transmittance.

(12) Voltage Holding Ratio (VHR-1; Measured at 25° C.; %)

A TN device used for measurement of a voltage holding ratio (VHR-1) had a polyimide alignment film, and a distance (cell gap) between two glass substrates was 5 micrometers. A sample was put in the device, and then the device was sealed with an ultraviolet-curable adhesive. A pulse voltage (60 microseconds at 5 V) was applied to the TN device and the device was charged. A decaying voltage was measured for 16.7 milliseconds with a high-speed voltmeter, and area A between a voltage curve and a horizontal axis in a unit cycle was determined. Area B is an area without decay. A voltage holding ratio is a percentage of area A to area B.

(13) Voltage Holding Ratio (VHR-2; Measured at 80° C.; %)

A TN device used for measurement of a voltage holding ratio (VHR-2) had a polyimide alignment film, and a distance (cell gap) between two glass substrates was 5 micrometers. A sample was put in the device, and then the device was sealed with an ultraviolet-curable adhesive. A pulse voltage (60 microseconds at 5 V) was applied to the TN device and the device was charged. A decaying voltage was measured for 16.7 milliseconds with a high-speed voltmeter, and area A between a voltage curve and a horizontal axis in a unit cycle was determined. Area B is an area without decay. A voltage holding ratio is a percentage of area A to area B.

Synthesis of a Liquid Crystal Compound

Example 1

Synthesis of Compound (No. 81)

Formula 24

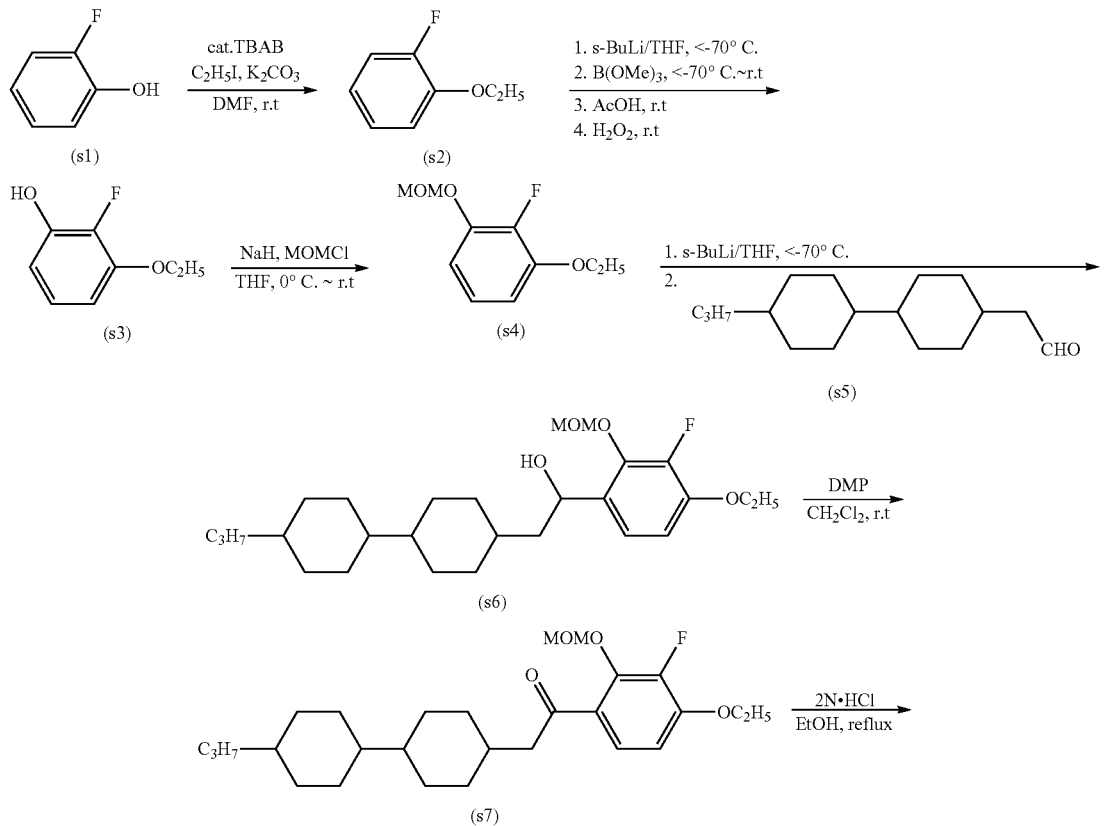

-continued

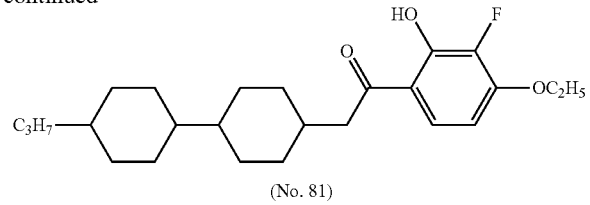

(No. 81)

First Step

Into a reaction vessel, o-fluorophenol (s1) (50 g, 446 mmol), potassium carbonate (123.3 g, 892 mmol), tetrabutylammonium bromide (TBAB) (7.2 g, 22.3 mmol) and N,N-dimethylformamide (DMF) (250 mL) were put. Ethyl iodide (139.1 g, 892 mmol) was slowly added dropwise at room temperature, and then the resulting mixture was stirred at room temperature for 5 hours. The reaction mixture was poured into saturated brine, and extracted with hexane. Combined organic layers were washed with water and saturated brine, and then dried over anhydrous sodium sulfate. The solution was concentrated under reduced pressure, and the residue was purified with vacuum distillation (2,670 Pa), and thus compound (s2) (52.3 g, 373 mmol; 83 mol %) was obtained.

Second Step

Under a nitrogen atmosphere, compound (s2) (20 g, 142.7 mmol) and THF (300 mL) were added into a reaction vessel, and the resulting mixture was cooled to −70° C. or lower. Then, sec-butyllithium (1.08 M; n-hexane/cyclohexane solution; 165 mL, 178.3 mmol) was added dropwise in the temperature range from −75° C. to −70° C., and the resulting mixture was further stirred for 1 hour. A THF (50 mL) solution of trimethyl borate (21.05 mL, 178.3 mmol) was added dropwise in the temperature range from −75° C. to −70° C., the resulting mixture was stirred for 3 hours while returning to 25° C. Thereto, acetic acid (12.25 mL, 214.0 mmol) was added dropwise in the temperature range of 20° C. to 25° C. After 30 minutes, hydrogen peroxide (30% aqueous solution, 32.3 g, 285.4 mmol) was added dropwise in the temperature range from 25° C. to 35° C., and the resulting mixture was further stirred for 10 hours. The reaction mixture was poured into water, and extracted with ethyl acetate. Combined organic layers were washed with water, an aqueous solution of sodium sulfite, water and saturated brine, and then dried over anhydrous sodium sulfate. The solution was concentrated under reduced pressure, and thus compound (s3) (22.0 g, 141.0 mol; 99 mol %) was obtained. Compound (s3) was used for the next reaction without further purification.

Third Step

Into a reaction vessel, sodium hydride (60%, 6.77 g, 169.2 mol) and THF (220 mL) were added, and the resulting mixture was subjected to ice-cooling. A THF (30 mL) solution of compound (s3) (22.0 g, 141.0 mol) was added dropwise in the temperature range from 0° C. to 10° C., and the resulting mixture was stirred for 3 hours while returning to 25° C. The resulting mixture was subjected ice-cooling again, and then chloromethyl methyl ether (MOMCl) (13.6 g, 169.2 mol) was added dropwise in the temperature range from 0° C. to 10° C., and the resulting mixture was stirred for 3 hours while returning to 25° C. The reaction mixture was poured into ice water, stirred for 10 minutes, and then extracted with ethyl acetate. Combined organic layers were washed with water and saturated brine, and then dried over anhydrous sodium sulfate. The solution was concentrated under reduced pressure, and the residue was purified with chromatography on silica gel (heptane:ethyl acetate=20:1 in a volume ratio), and then vacuum distillation (530 Pa), and thus compound (s4) (17.7 g, 88.6 mmol; 62 mol %) was obtained.

Fourth Step

Under a nitrogen atmosphere, compound (s4) (5 g, 25.0 mmol) and THF (75 mL) were added into a reaction vessel, and the resulting mixture was cooled to −70° C. or lower. Thereto, sec-butyllithium (1.08M; n-hexane/cyclohexane solution; 27.8 mL, 30.0 mmol) was added dropwise in the temperature range from −75° C. to −70° C., and the resulting mixture was further stirred for 1 hour. A THF (20 mL) solution of compound (s5) (6.26 g, 25.0 mmol) was added dropwise in the temperature range from −75° C. to −70° C., and the resulting mixture was stirred at 70° C. or lower for 3 hours. The reaction mixture was poured into ice water, and then the resulting mixture was stirred for 30 minutes, and extracted with ethyl acetate. Combined organic layers were sequentially washed with water and saturated brine, and then dried over anhydrous sodium sulfate. The solution was concentrated under reduced pressure, and the residue was purified with chromatography on silica gel (heptane:ethyl acetate=4:1 in a volume ratio), and thus compound (s6) (8.8 g, 19.5 mmol; 78 mol %) was obtained.

Fifth Step

Under a nitrogen atmosphere, compound (s6) (4.5 g, 9.99 mmol) and methylene chloride (45 mL) were added into a reaction vessel. The solution was cooled to 0° C., and Dess-Martin periodinane (DMP; 5.1 g, 12.0 mmol) was added thereto separately three times. The resulting mixture was further stirred for 2 hours while warming up to room temperature. The reaction mixture was poured into a saturated aqueous solution of sodium hydrogencarbonate, and extracted with ethyl acetate. Combined organic layers were sequentially washed with water, an aqueous solution of sodium sulfite, water and saturated brine, and then dried over anhydrous sodium sulfate. The solution was concentrated under reduced pressure, and the residue was purified with chromatography on silica gel (heptane:ethyl acetate=9:1 in a volume ratio), and thus compound (s7) (1.61 g, 3.6 mmol; 36 mol %) was obtained.

Sixth Step

Into a reaction vessel, compound (s7) (1.61 g, 3.6 mmol), 2 N hydrochloric acid (2.15 mL, 4.3 mmol) and ethanol (30 mL) were added. The mixture was stirred under heating reflux for an hour and a half. The resulting mixture was cooled to 25° C., and then water was added to the reaction mixture, and the resulting mixture was extracted with ethyl acetate. Combined organic layers were washed with water and saturated brine, and then dried over anhydrous sodium sulfate. The solution was concentrated under reduced pressure, and the residue was purified with chromatography on silica gel (heptane:ethyl acetate=20:1 in a volume ratio), and thus compound (No. 81) (17.7 g, 88.6 mmol; 62 mol %) was obtained.

$^1$H-NMR (δ ppm; CDCl$_3$): 12.72 (s, 1H, phenol), 7.48 (dd, 1H), 6.48 (dd, 1H), 4.19 (q, 2H), 2.74 (d, 2H), 1.85-1.66 (m, 9H), 1.48 (t, 2H), 1.31-0.91 (m, 16H), 0.86 (t, 3H).

A phase transition temperature of compound (No. 81) obtained was as described below.

Phase transition temperature: C 137.2 I.

Example 2

Synthesis of Compound (No. 83)

First Step

Compound (s9) (5.64 g, 11.1 mmol) was obtained by using compound (s4) (2.93 g, 14.7 mmol) and compound (s8) (4.5 g, 14.7 mmol) as starting materials, using sec-butyllithium (1.06 M; n-hexane/cyclohexane solution; 16.6 mL, 17.6 mmol) as a reactant, and by performing reaction operations in a manner similar to the operations in the fourth step in Example 1. A yield based on compound (s8) was 76 mol %.

Second Step

Compound (s10) (4.3 g, 8.5 mmol) was obtained by using compound (s9) (5.64 g, 11.1 mmol) as a starting material, using Dess-Martin periodinane (DMP; 5.65 g, 13.3 mmol) as a reactant, and by performing reaction operations in a manner similar to the operations in the fifth step in Example 1. A yield based on compound (s9) was 77 mol %.

Third Step

Compound (No. 83) (2.2 g, 4.77 mmol) was obtained by using compound (s10) (4.3 g, 8.5 mmol) as starting materials, using 2 N hydrochloric acid (5.1 mL, 10.2 mmol) as a reactant, and by performing reaction operations in a manner similar to the operations in the sixth step in Example 1. A yield based on compound (s10) was 56 mol %.

$^1$H-NMR (δ ppm; CDCl$_3$): 12.73 (s, 1H, phenol), 7.47 (dd, 1H), 6.48 (dd, 1H), 4.20 (q, 2H), 2.74 (d, 2H), 1.86-1.68 (m, 9H), 1.48 (t, 2H), 1.32-0.91 (m, 24H), 0.87 (t, 3H).

A phase transition temperature of compound (No. 83) obtained was as described below.

Phase transition temperature: C 129.0 (N 122.0) I.

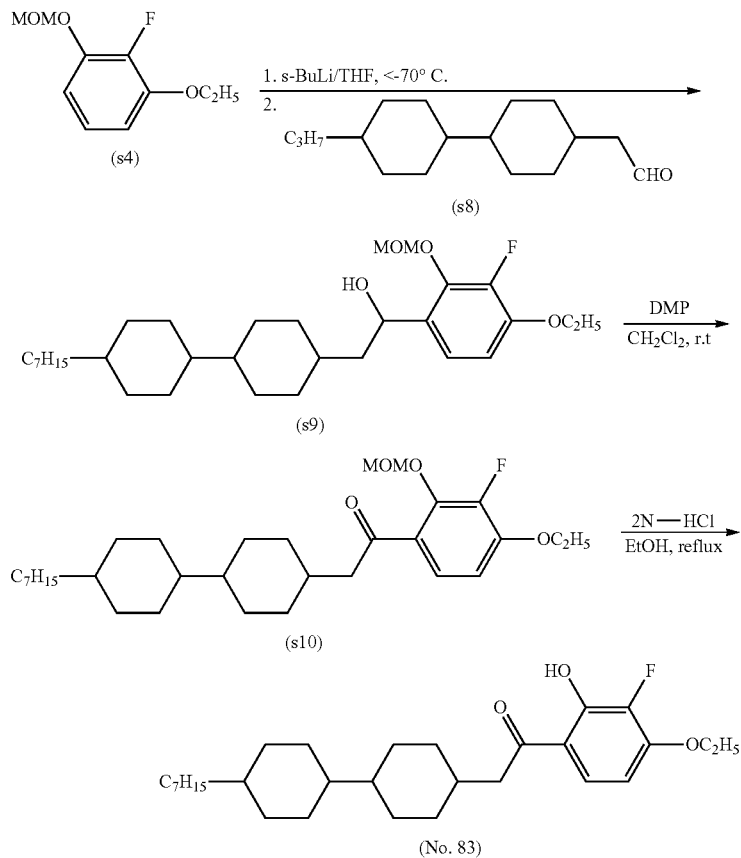

Example 3

Synthesis of Compound (No. 121)

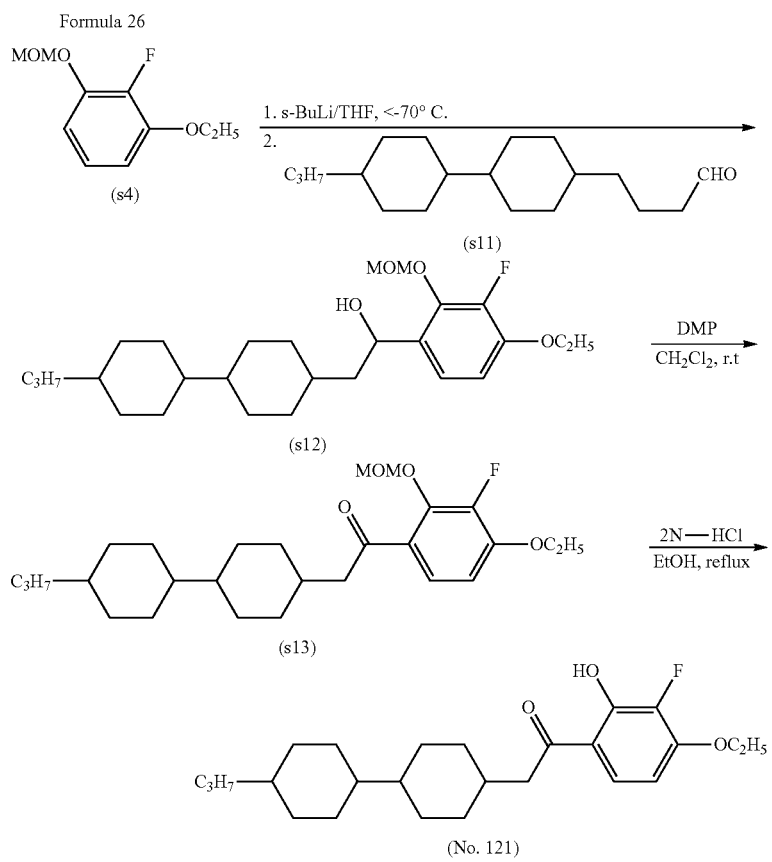

First Step

Compound (s12) (2.57 g, 5.37 mmol) was obtained by using compound (s4) (1.8 g, 9.0 mmol) and compound (s11) (2.5 g, 9.0 mmol) as starting materials, using sec-butyllithium (1.06 M; n-hexane/cyclohexane solution; 10.2 mL, 10.8 mmol) as a reactant, and by performing reaction operations in a manner similar to the operations in the fourth step in Example 1. A yield based on compound (s11) was 60 mol %.

Second Step

Compound (s13) (2.25 g, 4.7 mmol) was obtained by using compound (s12) (2.57 g, 5.37 mmol) as a starting material, using Dess-Martin periodinane (DMP; 2.7 g, 6.4 mmol) as a reactant, and by performing reaction operations in a manner similar to the operations in the fifth step in Example 1. A yield based on compound (s12) was 88 mol %.

Third Step

Compound (No. 121) (1.5 g, 3.5 mmol) was obtained by using compound (s13) (2.25 g, 4.7 mmol) as a starting material and 2 N hydrochloric acid (2.8 mL, 5.6 mmol) as a reactant, and by performing reaction operations in a manner similar to the operations in the sixth step in Example 1. A yield based on compound (s13) was 74 mol %.

$^1$H-NMR (δ ppm; CDCl$_3$): 12.70 (s, 1H, phenol), 7.46 (dd, 1H), 6.48 (dd, 1H), 4.18 (q, 2H), 2.91 (d, 2H), 1.85-1.66 (m, 9H), 1.46 (t, 2H), 1.31-0.91 (m, 20H), 0.87 (t, 3H).

A phase transition temperature of compound (No. 121) obtained was as described below.

Phase transition temperature: C 99.3 C 147.8 N 158.7 I.

Example 4

Synthesis of Compound (No. 21)

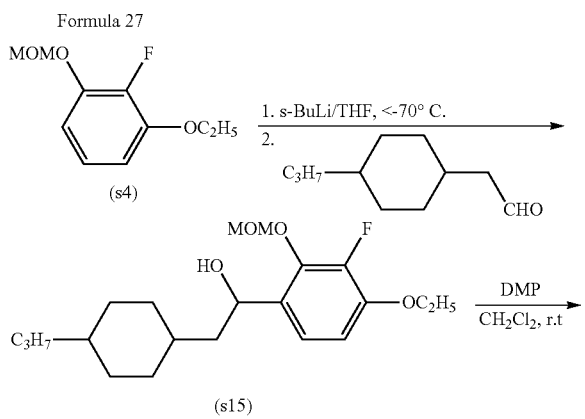

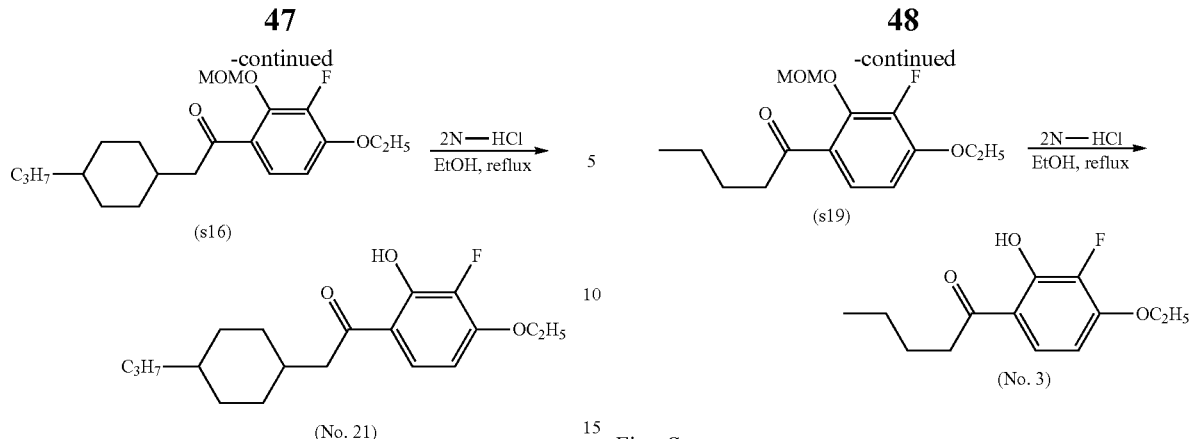

First Step

Compound (s15) (3.4 g, 9.2 mmol) was obtained by using compound (s4) (3.0 g, 15.0 mmol) and compound (s14) (2.5 g, 15.0 mmol) as starting materials and sec-butyllithium (1.08 M; n-hexane/cyclohexane solution; 16.7 mL, 18.0 mmol) as a reactant, and by performing reaction operations in a manner similar to the operations in the fourth step in Example 1. A yield based on compound (s14) was 61 mol %.

Second Step

Compound (s16) (2.9 g, 7.9 mmol) was obtained by using compound (s15) (3.1 g, 8.4 mmol) as a starting material and Dess-Martin periodinane (DMP; 4.3 g, 10.1 mmol) as a reactant, and by performing reaction operations in a manner similar to the operations in the fifth step in Example 1. A yield based on compound (s15) was 94 mol %.

Third Step

Compound (No. 21) (1.9 g, 5.9 mmol) was obtained by using compound (s16) (2.8 g 7.6 mmol) as a starting material and 2 N hydrochloric acid (4.6 mL, 9.2 mmol) as a reactant, and by performing reaction operations in a manner similar to the operations in the sixth step in Example 1. A yield based on compound (s16) was 78 mol %.

$^1$H-NMR (δ ppm; CDCl$_3$): 12.72 (s, 1H, phenol), 7.49 (dd, 1H), 6.48 (dd, 1H), 4.19 (q, 2H), 2.75 (d, 2H), 1.84-1.65 (m, 5H), 1.47 (t, 2H), 1.33-0.91 (m, 10H), 0.87 (t, 3H).

A phase transition temperature of compound (No. 21) obtained was as described below.

Phase transition temperature: C 107.4 I.

Example 5

Synthesis of Compound (No. 3)

Formula 28

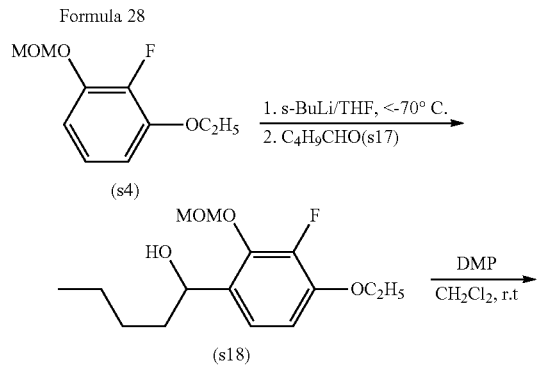

First Step

Compound (s18) (8.7 g, 30.4 mmol) was obtained by using compound (s4) (7.5 g, 37.5 mmol) and valeraldehyde (s17) (3.87 g, 45 mmol) as starting materials and sec-butyllithium (1.06 M; n-hexane/cyclohexane solution; 42.4 mL, 45 mmol) as a reactant, and by performing reaction operations in a manner similar to the operations in the fourth step in Example 1. A yield based on compound (s17) was 81 mol %.

Second Step

Compound (s19) (6.0 g, 21.2 mmol) was obtained by using compound (s18) (8.2 g, 28.6 mmol) as a starting material and Dess-Martin periodinane (DMP; 14.6 g, 34.4 mmol) as a reactant, and by performing reaction operations in a manner similar to the operations in the fifth step in Example 1. A yield based on compound (s18) was 74 mol %.

Third Step

Compound (No. 3) (3.5 g, 14.6 mmol) was obtained by using compound (s19) (6.0 g, 21.2 mmol) as a starting material and 2 N hydrochloric acid (12.7 mL 25.4 mmol) as a reactant, and by performing reaction operations in a manner similar to the operations in the sixth step in Example 1. A yield based on compound (s19) was 69 mol %.

$^1$H-NMR (δ ppm; CDCl$_3$): 12.75 (s, 1H), 7.50 (dd, 1H), 6.50 (dd, 1H), 4.20 (q, 2H), 2.91 (t, 2H), 1.71 (quintet, 2H), 1.48 (t, 2H), 1.42 (sextet, 2H), 0.96 (t, 3H).

A phase transition temperature of compound (No. 3) obtained was as described below.

Phase transition temperature: C 47.0 C 48.7 I.

Various compounds as described in Examples 6 to 9 were prepared by using the corresponding starting materials according to the techniques as shown in Examples 1 to 5, and the compounds were confirmed to be target compounds.

Example 6

Compound (No. 6)

Formula 29

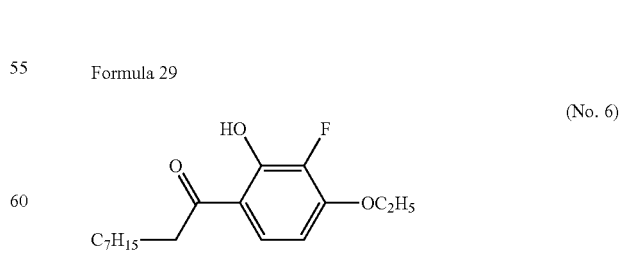

Chemical shifts (δ (ppm)) according to a $^1$H NMR analysis were as described below, and the compound obtained was identified to be compound (No. 6). In addition, a solvent for measurement was CDCl$_3$.

¹H-NMR (δ ppm; CDCl₃): 12.76 (s, 1H), 7.50 (dd, 1H), 6.51 (dd, 1H), 4.19 (q, 2H), 2.91 (t, 2H), 1.71 (quintet, 2H), 1.48 (t, 2H), 1.46-1.42 (m, 11H), 0.97 (t, 3H).

A phase transition temperature of compound (No. 6) obtained was as described below.

Phase transition temperature: C 53.6 I.

Example 7

Compound (No. 127)

Formula 30

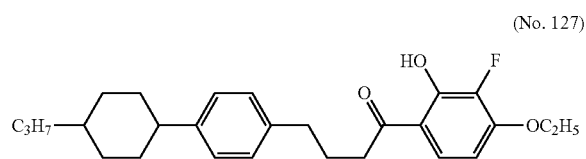

(No. 127)

Chemical shifts (δ (ppm)) according to a ¹H NMR analysis were as described below, and the compound obtained was identified to be compound (No. 127). In addition, a solvent for measurement was CDCl₃.

¹H-NMR (δ ppm; CDCl₃): 12.57 (s, 1H), 7.40 (dd, 1H), 7.13-7.10 (m, 4H), 6.45 (dd, 1H), 4.16 (q, 2H), 2.91 (t, 2H), 2.67 (t, 2H), 2.43 (tt, 1H), 2.05 (quintet, 2H), 1.89-1.83 (m, 4H), 1.46 (t, 4H), 1.43-0.99 (m, 8H), 0.89 (t, 3H).

A phase transition temperature of compound (No. 127) obtained was as described below.

Phase transition temperature: C 117.7 I.

Example 8

Compound (No. 131)

Formula 31

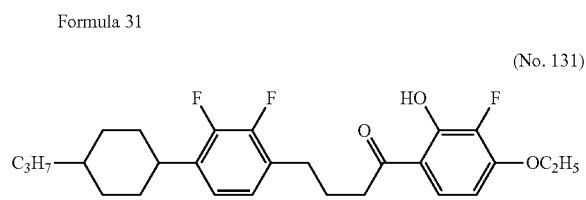

(No. 131)

Chemical shifts (δ (ppm)) according to a ¹H NMR analysis were as described below, and the compound obtained was identified to be compound (No. 131). In addition, a solvent for measurement was CDCl₃.

¹H-NMR (δ ppm; CDCl₃): 12.51 (s, 1H), 7.44 (dd, 1H), 6.88-6.87 (m, 2H), 6.48 (dd, 1H), 4.19 (q, 2H), 2.95 (t, 3H), 2.79 (tt, 1H), 2.73 (t, 2H), 2.05 (quintet, 2H), 1.85 (d, 4H), 1.49-1.02 (m, 11H), 0.89 (t, 3H).

A phase transition temperature of compound (No. 131) obtained was as described below.

Phase transition temperature: C 99.0 I.

Example 9

Synthesis of Compound (No. 141)

Formula 32

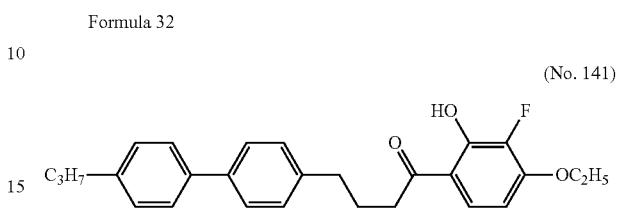

(No. 141)

Chemical shifts (δ (ppm)) according to a ¹H NMR analysis were as described below, and the compound obtained was identified to be compound (No. 141). In addition, a solvent for measurement was CDCl₃.

¹H-NMR (δ ppm; CDCl₃): 12.58 (s, 1H), 7.50 (dd, 1H), 7.40 (dd, 1H), 7.25-7.22 (m, 4H), 6.44 (dd, 1H), 4.15 (q, 2H), 2.93 (t, 2H), 2.74 (t, 2H), 2.63 (t, 2H), 2.09 (quintet, 2H), 1.64 (quintet, 2H), 1.45 (t, 2H), 1.39-1.31 (m, 4H), 0.89 (t, 3H).

A phase transition temperature of compound (No. 141) obtained was as described below.

Phase transition temperature: C 125.4 I.

Example 10

Synthesis of Compound (No. 14)

Formula 33

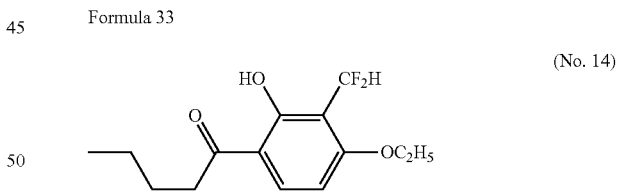

(No. 14)

Chemical shifts (δ (ppm)) according to a ¹H NMR analysis were as described below, and the compound obtained was identified to be compound (No. 14). In addition, a solvent for measurement was CDCl₃.

¹H-NMR (δ ppm; CDCl₃): 13.35 (s, 1H), 7.81 (d, 1H), 7.13 (t, 1H, J=53.7), 6.46 (d, 1H), 4.17 (q, 2H), 2.91 (t, 2H), 1.71 (quintet, 2H), 1.46 (t, 3H), 1.43 (sextet, 2H), 0.86 (t, 3H).

A phase transition temperature of compound (No. 14) obtained was as described below.

Phase transition temperature: C 72.8 I.

Comparative Example 1

Synthesis of Comparative Compound (CoNo. 1)

Formula 33

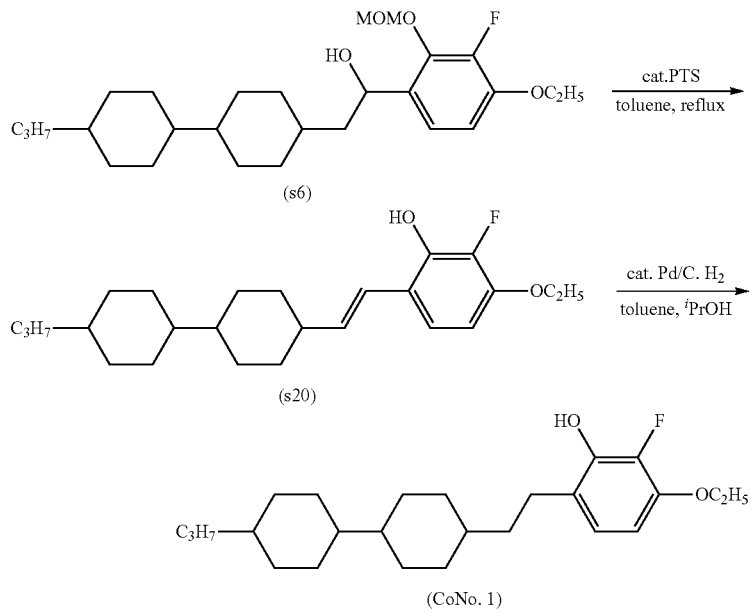

First Step

A mixture of compound (s6) (3.0 g, 6.66 mmol) as obtained in the fourth step in Example 1 and p-toluenesulfonic acid (60 mg, 0.33 mmol) in toluene (60 mL) were stirred under reflux for 1 hour. The reaction mixture was cooled to room temperature, and then washed with a saturated aqueous solution of sodium hydrogencarbonate, water and saturated brine, and then dried over anhydrous sodium sulfate. The solution was concentrated under reduced pressure, and the residue was purified with chromatography on silica gel (heptane:ethyl acetate=20:1 in a volume ratio) and by recrystallization (solvent; heptane), and thus compound (s20) (0.9 g, 2.32 mmol; 35 mol %) was obtained.

Second Step

Compound (s20) (0.9 g, 2.32 mmol) and 5% palladium-on-carbon catalyst Dess-Martin periodinane (14.6 g) were mixed in toluene (4.5 mL) and isopropanol 4.5 mL), and then the resulting mixture was stirred under a hydrogen atmosphere for 3 hours. The reaction mixture was filtered, the filtrate was concentrated, and the residue was purified with chromatography on silica gel (heptane:ethyl acetate=20:1 in a volume ratio), and recrystallization (solvent; heptane), and thus compound (CoNo. 1) (0.6 g, 1.54 mmol; 66 mol %) was obtained.

$^1$H-NMR ($\delta$ ppm; CDCl$_3$): 6.75 (dd, 1H), 6.53 (t, 1H), 5.09 (d, 1H), 4.07 (q, 2H), 2.57 (t, 2H), 1.83-1.67 (m, 8H), 1.42 (t, 3H), 1.31-0.94 (m, 17H), 0.86 (t, 3H).

A phase transition temperature of compound (CoNo. 1) obtained was as described below.

Phase transition temperature: C 85.3 S$_A$ 153 N 167 I.

Comparative Example 2

Synthesis of Comparative Compound (CoNo. 2)

Formula 34

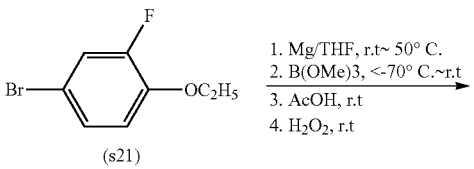

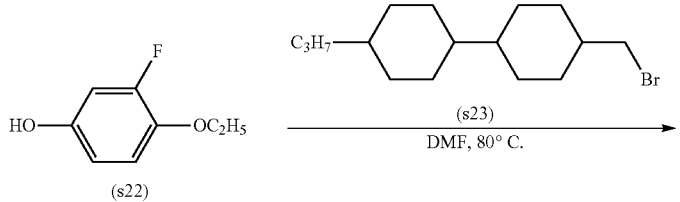

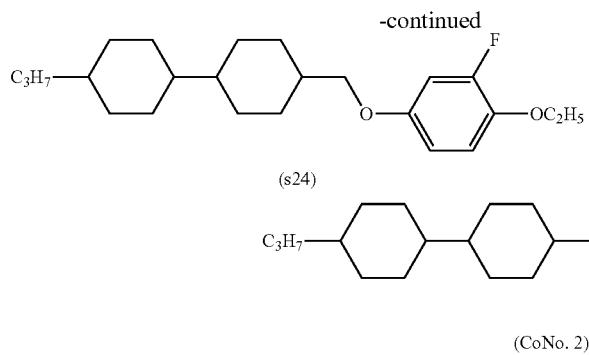
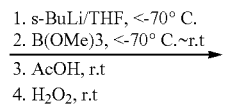

First Step

Under a nitrogen atmosphere, compound (s21) (80 g, 365 mmol) and metal magnesium (10.65 g, 438 mmol) were added into a reaction vessel, and thus a Grignard reagent was prepared in THF (800 mL). After 2 hours, a THF (110 mL) solution of trimethyl borate (56.0 mL, 474.5 mmol) was added dropwise in the temperature range from −75° C. to −70° C., and the resulting mixture was stirred for 20 hours while returning to 25° C. Thereto, acetic acid (31.3 mL, 547.5 mmol) was added dropwise in the temperature range of 20° C. to 25° C. After 30 minutes, hydrogen peroxide (30% aqueous solution, 82.7 g, 730 mmol) was added dropwise in the temperature range of 25° C. to 35° C., and the resulting mixture was further stirred for 10 hours. The reaction mixture was poured into water, and extracted with ethyl acetate. Combined organic layers were washed with water, an aqueous solution of sodium sulfite, water and saturated brine, and then dried over anhydrous sodium sulfate. The solution was concentrated under reduced pressure, and then the residue was purified with chromatography on silica gel (heptane:ethyl acetate=20:1 in a volume ratio) and by vacuum distillation (930 Pa), and thus compound (s22) (38.0 g, 243 mmol; 66 mol %) was obtained.

Second Step

Compound (s22) (19.4 g, 124 mmol), potassium carbonate (34.2 g, 248 mmol), tetrabutylammonium bromide (TBAB) (4.0 g, 12.4 mmol) and N,N-dimethylformamide (DMF) (450 mL) were added into a reaction vessel. Compound (s23) (45 g, 149 mmol) was slowly added dropwise at room temperature, and the resulting mixture was stirred at 80° C. for 10 hours. After cooling to room temperature, the reaction mixture was poured into saturated brine, and extracted with toluene. Combined organic layers were washed with water and saturated brine, and then dried over anhydrous sodium sulfate. The solution was concentrated under reduced pressure, and the residue was purified with silica gel chromatography (heptane:ethyl acetate=20:1 in a volume ratio) and by recrystallization (solvent; heptane, ethanol), and thus compound (s24) (32.4 g, 87.6 mmol; 69 mol %) was obtained.

Third Step

Under a nitrogen atmosphere, compound (s24) (5 g, 13.3 mmol) and THF (125 mL) were added into a reaction vessel, and the resulting mixture was cooled to −70° C. or lower. Thereto, sec-butyllithium (1.08 M; n-hexane/cyclohexane solution; 14.77 mL, 15.96 mmol) was added dropwise in the temperature range of −75° C. to −70° C., and the resulting mixture was further stirred for 1 hour. A THF (5 mL) solution of trimethyl borate (1.88 mL, 15.96 mmol) was added dropwise in the temperature range from −75° C. to −70° C. while returning to 25° C. Thereto, acetic acid (1.14 mL, 19.95 mmol) was added dropwise in the temperature range of 20° C. to 25° C. After 30 minutes, hydrogen peroxide (30% aqueous solution, 3.76 g, 33.25 mmol) was added dropwise in the temperature range from 25° C. to 35° C., and the resulting mixture was further stirred for 10 hours. The reaction mixture was poured into water, and extracted with ethyl acetate. Combined organic layers were washed with water, an aqueous solution of sodium sulfite, water and saturated brine, and then dried over anhydrous sodium sulfate. The solution was concentrated under reduced pressure, and the residue was purified with chromatography on silica gel (heptane:ethyl acetate=9:1 in a volume ratio) and by recrystallization (solvent; heptane), and thus compound (CoNo. 2) (3.1 g, 7.9 mmol; 59 mol %) was obtained.

$^1$H-NMR (δ ppm; CDCl$_3$): 6.50 (dd, 1H), 6.40 (t, 1H), 5.44 (d, 1H), 4.03 (q, 2H), 3.78 (d, 2H), 1.90-1.69 (m, 8H), 1.53 (t, 3H), 1.42-0.93 (m, 15H), 0.87 (t, 3H).

A phase transition temperature of compound (CoNo. 2) obtained was as described below.

Phase transition temperature: C 100 N 157.6 I.

Physical Properties of Liquid Crystal Compounds (1) A sample (liquid crystal composition) including 95% of base liquid crystal A and 5% of liquid crystal compound (No. 81) was prepared. Physical properties of the sample were as described below. Maximum temperature $(T_{NI})$= 76.2° C.; value of dielectric anisotropy (Δ∈)=−2.00; value of optical anisotropy (Δn)=0.0895. Values of physical properties of liquid crystal compound (No. 81) as calculated according to the extrapolation method from values of physical properties of base liquid crystal A and the sample and a mixing ratio of the liquid crystal compound were as described below. Maximum temperature $(T_{NI})$=106.6° C.; value of dielectric anisotropy (Δ∈)=−15.30; value of optical anisotropy (Δn)=0.137.

(2) A sample (liquid crystal composition) including 97% of base liquid crystal A and 3% of liquid crystal compound (No. 83) was prepared. Physical properties of the sample were as described below. Maximum temperature $(T_{NI})$= 75.3° C.; value of dielectric anisotropy (Δ∈)=−1.73; value of optical anisotropy (Δn)=0.0882. Values of physical properties of liquid crystal compound (No. 83) as calculated according to the extrapolation method from values of physical properties of base liquid crystal A and the sample and a mixing ratio of the liquid crystal compound were as described below. Maximum temperature $(T_{NI})$=97.9° C.; value of dielectric anisotropy (Δ∈)=−15.63; value of optical anisotropy (Δn)=0.127.

(3) A sample (liquid crystal composition) including 95% of base liquid crystal A and 5% of liquid crystal compound (No. 121) was prepared. Physical properties of the sample were as described below. Maximum temperature $(T_{NI})$=

78.1° C.; value of dielectric anisotropy (Δ∈)=−1.96; value of optical anisotropy (Δn)=0.090. Values of physical properties of liquid crystal compound (No. 121) as calculated according to the extrapolation method from values of physical properties of base liquid crystal A and the sample and a mixing ratio of the liquid crystal compound were as described below. Maximum temperature $(T_{NI})$=144.6° C.; value of dielectric anisotropy (Δ∈)=−11.80; value of optical anisotropy (Δn)=0.147.

(4) A sample (liquid crystal composition) including 95% of base liquid crystal A and 5% of liquid crystal compound (No. 21) was prepared. Physical properties of the sample were as described below. Maximum temperature $(T_{NI})$=70.0° C.; value of dielectric anisotropy (Δ∈)=−2.24; value of optical anisotropy (Δn)=0.0875. Values of physical properties of liquid crystal compound (No. 21) as calculated according to the extrapolation method from values of physical properties of base liquid crystal A and the sample and a mixing ratio of the liquid crystal compound were as described below. Maximum temperature $(T_{NI})$=−17.4° C.; value of dielectric anisotropy (Δ∈)=−20.10; value of optical anisotropy (Δn)=0.097.

(5) A sample (liquid crystal composition) including 85% of base liquid crystal A and 15% of liquid crystal compound (No. 3) was prepared. Physical properties of the sample were as described below. Maximum temperature $(T_{NI})$=48.4° C.; value of dielectric anisotropy (Δ∈)=−3.07; value of optical anisotropy (Δn)=0.081. Values of physical properties of liquid crystal compound (No. 3) as calculated according to the extrapolation method from values of physical properties of base liquid crystal A and the sample and a mixing ratio of the liquid crystal compound were as described below. Maximum temperature $(T_{NI})$=−100.1° C.; value of dielectric anisotropy (Δ∈)=−13.10; value of optical anisotropy (Δn)=0.047.

(6) A sample (liquid crystal composition) including 85% of base liquid crystal A and 15% of liquid crystal compound (No. 6) was prepared. Physical properties of the sample were as described below. Maximum temperature $(T_{NI})$=51.8° C.; value of dielectric anisotropy (Δ∈)=−3.07; value of optical anisotropy (Δn)=0.082. Values of physical properties of liquid crystal compound (No. 6) as calculated according to the extrapolation method from values of physical properties of base liquid crystal A and the sample and a mixing ratio of the liquid crystal compound were as described below. Maximum temperature $(T_{NI})$=−77.4° C.; value of dielectric anisotropy (Δ∈)=−13.10; value of optical anisotropy (Δn)=0.052.

(7) A sample (liquid crystal composition) including 95% of base liquid crystal A and 5% of liquid crystal compound (No. 127) was prepared. Physical properties of the sample were as described below. Maximum temperature $(T_{NI})$=75.0° C.; value of dielectric anisotropy (Δ∈)=−1.91; value of optical anisotropy (Δn)=0.091. Values of physical properties of liquid crystal compound (No. 127) as calculated according to the extrapolation method from values of physical properties of base liquid crystal A and the sample and a mixing ratio of the liquid crystal compound were as described below. Maximum temperature $(T_{NI})$=82.6° C.; value of dielectric anisotropy (Δ∈)=−11.98; value of optical anisotropy (Δn)=0.165.

(8) A sample (liquid crystal composition) including 95% of base liquid crystal A and 5% of liquid crystal compound (No. 141) was prepared. Physical properties of the sample were as described below. Maximum temperature $(T_{NI})$=75.6° C.; value of dielectric anisotropy (Δ∈)=−1.83; value of optical anisotropy (Δn)=0.093. Values of physical properties of liquid crystal compound (No. 141) as calculated according to the extrapolation method from values of physical properties of base liquid crystal A and the sample and a mixing ratio of the liquid crystal compound were as described below. Maximum temperature $(T_{NI})$=94.6° C.; value of dielectric anisotropy (Δ∈)=−10.38; value of optical anisotropy (Δn)=0.207.

(9) A sample (liquid crystal composition) including 85% of base liquid crystal A and 15% of liquid crystal compound (CoNo. 1) was prepared. Physical properties of the sample were as described below. Maximum temperature $(T_{NI})$=82.7° C.; value of dielectric anisotropy (Δ∈)=−1.28; value of optical anisotropy (Δn)=0.0883. Values of physical properties of liquid crystal compound (CoNo. 1) as calculated according to the extrapolation method from values of physical properties of base liquid crystal A and the sample and a mixing ratio of the liquid crystal compound were as described below. Maximum temperature $(T_{NI})$=128.6° C.; value of dielectric anisotropy (Δ∈)=−1.17; value of optical anisotropy (Δn)=0.096.

(10) A sample (liquid crystal composition) including 85% of base liquid crystal A and 15% of liquid crystal compound (CoNo. 2) was prepared. Physical properties of the sample were as described below. Maximum temperature $(T_{NI})$=82.4° C.; value of dielectric anisotropy (Δ∈)=−1.80; value of optical anisotropy (Δn)=0.0885. Values of physical properties of liquid crystal compound (CoNo. 2) as calculated according to the extrapolation method from values of physical properties of base liquid crystal A and the sample and a mixing ratio of the liquid crystal compound were as described below. Maximum temperature $(T_{NI})$=126.6° C.; value of dielectric anisotropy (Δ∈)=−4.63; value of optical anisotropy (Δn)=0.097.

Synthesis Examples

Compounds (No. 1 to No. 220) as described below can be prepared in a manner similar to the synthetic processes described above, and the synthesis methods described in Examples 1 to 5. In addition, compounds (Nos. 3, 6, 21, 81, 83, 121, 127, 131 and 141) according to Examples 1 to 9 were also exemplified.

Formula 35

No.

1

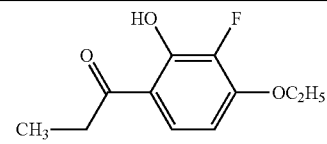

2

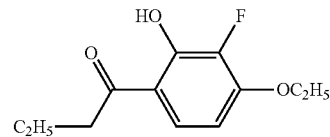

3

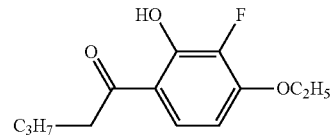

C 47.0 C 48.7 I
$T_{NI}$; −100.1☐, Δ ∈; −12.65, Δ n; 0.047

| Formula 35 | |
|---|---|
| No. | |
| 4 | 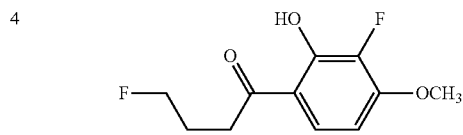 |
| 5 | 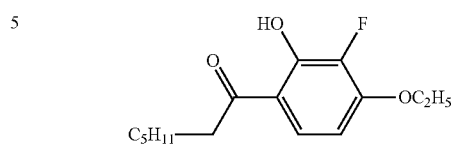 |
| 6 | 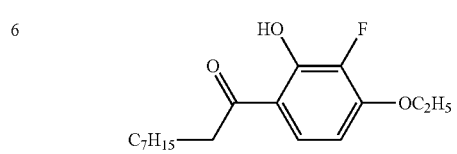
C 53.6 I
T$_{Ni}$; −77.4, Δ ε; −12.53, Δ n; 0.052 |
| 7 | 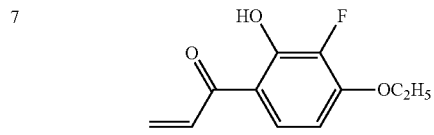 |
| 8 | 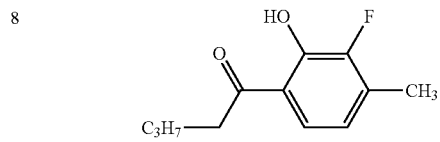 |
| 9 | 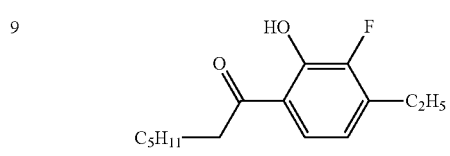 |
| 10 | 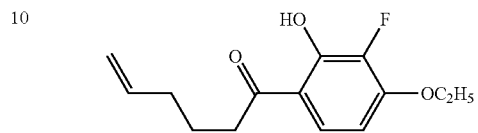 |
| 11 | 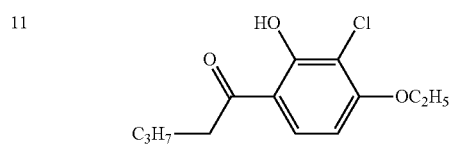 |
| 12 | 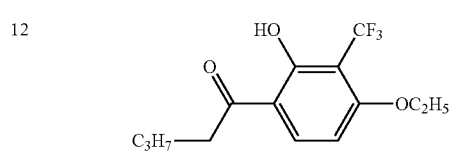 |
| 13 | 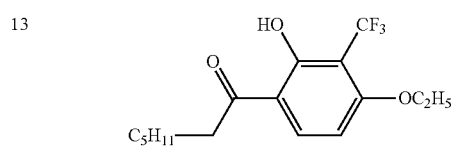 |
| Formula 35 | |
|---|---|
| No. | |
| 14 | 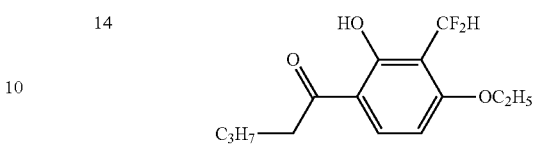 |
| 15 | 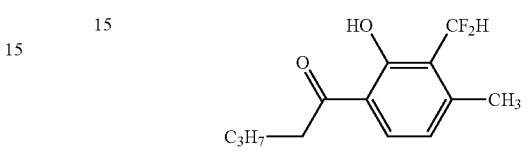 |
| 16 | 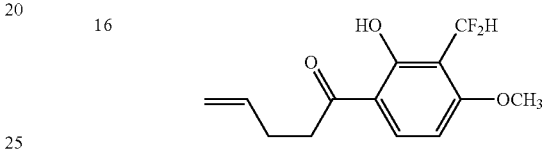 |
| 17 | 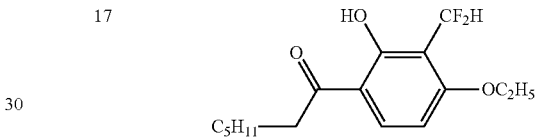 |
| 18 | 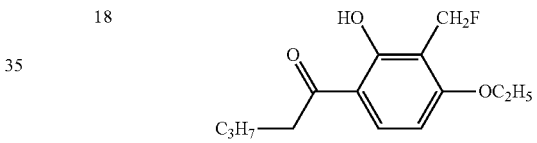 |
| 19 | 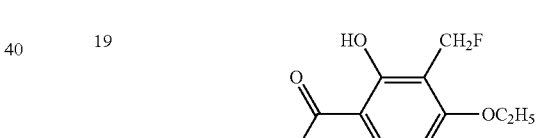 |
| 20 | 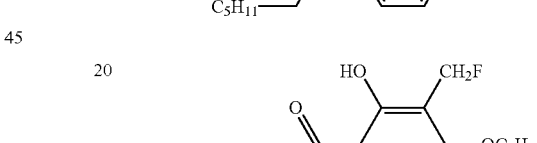 |
| Formula 36 | |
|---|---|
| No. | |
| 21 | 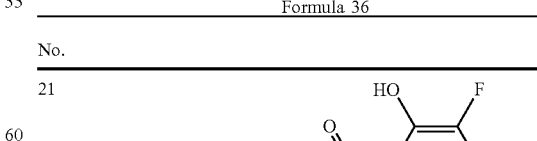
C 107.4 I
T$_{Ni}$; −17.4° C., Δ ε;−20.10, Δ n; 0.097 |

-continued
Formula 36
| No. | |
|---|---|
| 22 | 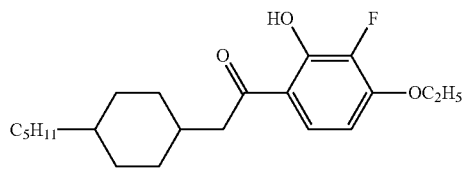 |
| 23 | 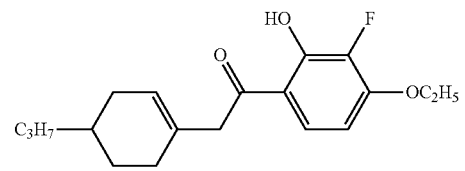 |
| 24 | 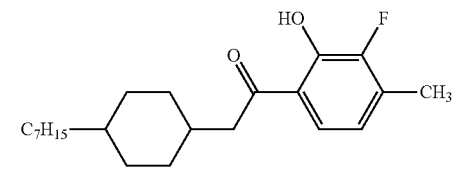 |
| 25 | 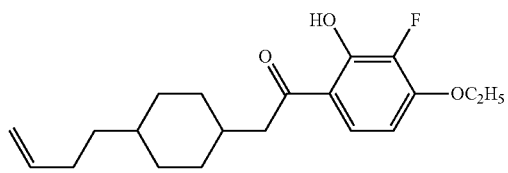 [SMILES: C=CCCC1CCC(CC(=O)c2ccc(OCC)c(F)c2O)CC1] |
| 26 | 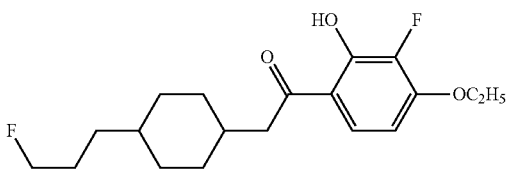 [SMILES: CCOc1ccc(C(=O)CC2CCC(CCCF)CC2)c(O)c1F] |
| 27 | 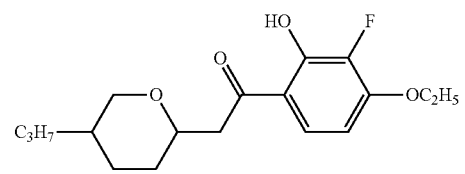 |
| 28 | 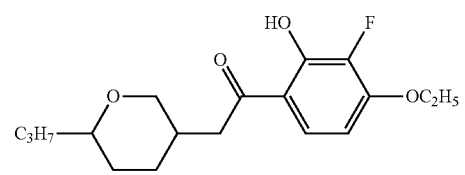 |
| 29 | 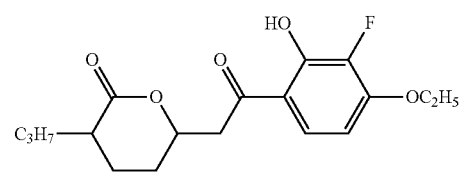 |
-continued
Formula 36
| No. | |
|---|---|
| 30 | 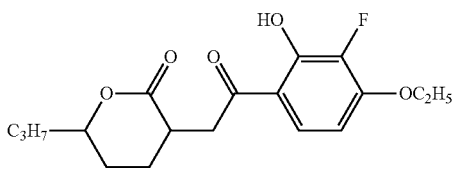 |
| 31 | 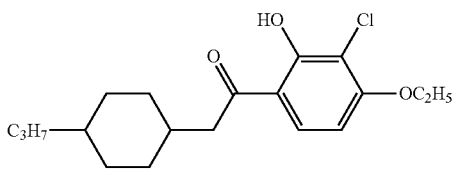 |
| 32 | 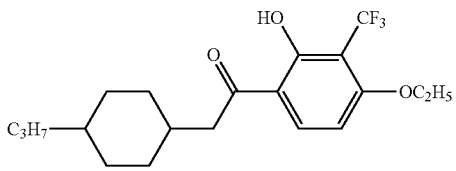 |
| 33 | 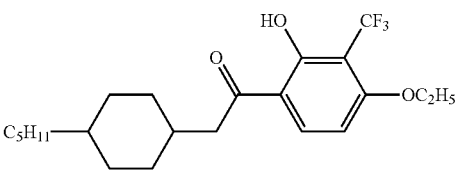 |
| 34 | 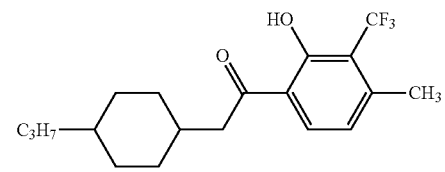 |
| 35 | 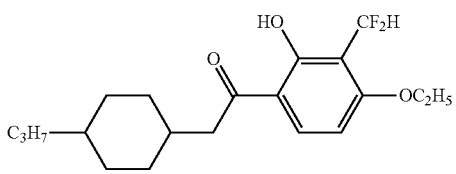 |
| 36 | 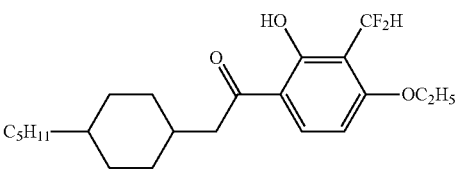 |
| 37 | 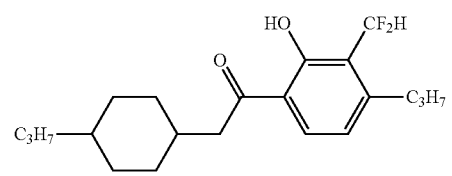 |

| Formula 36 |
| --- |
| No. |
| 38 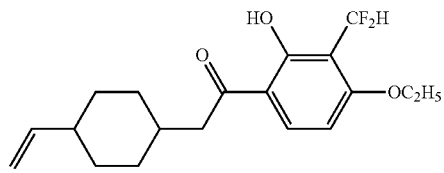 [SMILES: C=CC1CCC(CC(=O)c2ccc(OCC)c(C(F)F)c2O)CC1] |
| 39 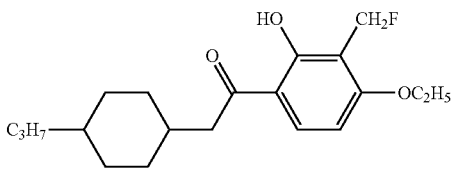 |
| 40 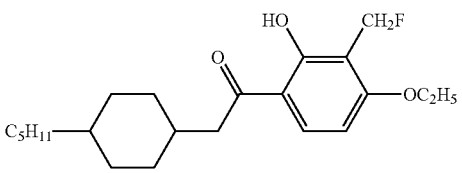 |
| Formula 37 |
| --- |
| No. |
| 41 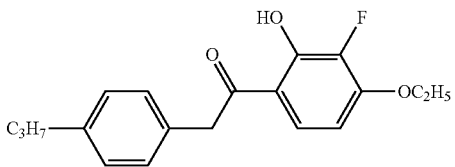 |
| 42 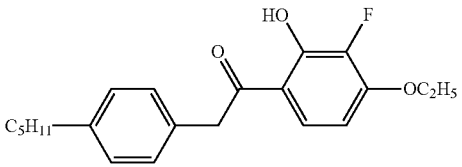 |
| 43 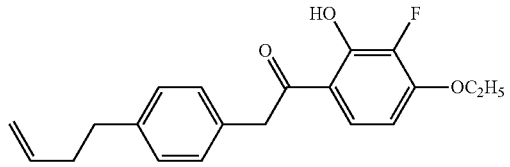 [SMILES: C=CCCc1ccc(CC(=O)c2ccc(OCC)c(F)c2O)cc1] |
| 44 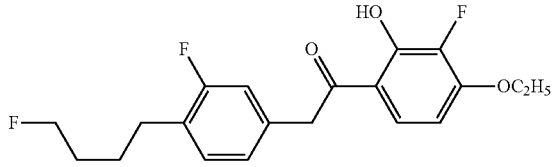 [SMILES: CCOc1ccc(C(=O)Cc2ccc(CCCCF)c(F)c2)c(O)c1F] |
| 45 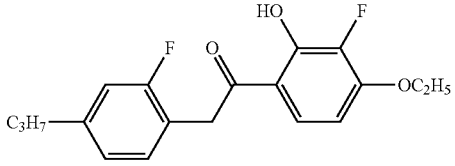 |
| Formula 37 |
| --- |
| No. |
| 46 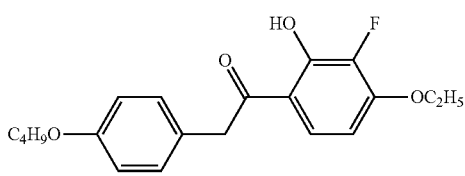 |
| 47 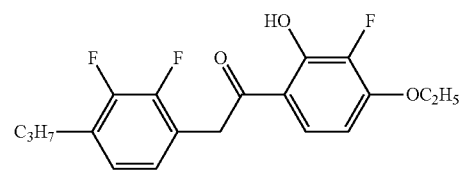 |
| 48 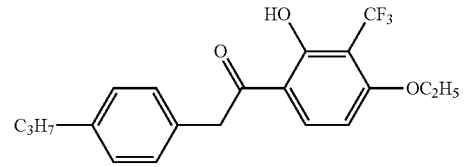 |
| 49 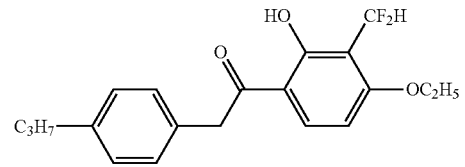 |
| 50 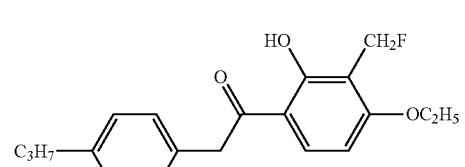 |
| 51 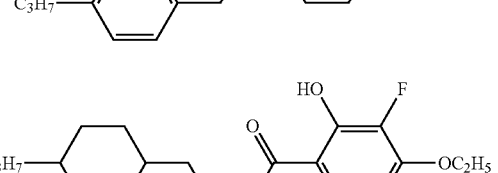 |
| 52 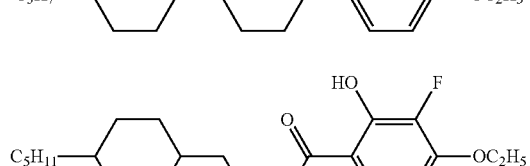 |
| 53 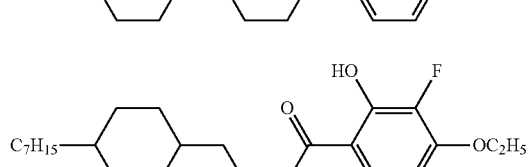 |
| 54 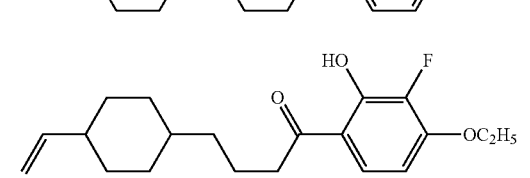 |

-continued

| Formula 37 |
| --- |
| No. |

55, 56, 57, 58, 59, 60

-continued

| Formula 38 |
| --- |
| No. |

65, 66, 67, 68, 69, 70, 71, 72, 73, 74, 75

| Formula 38 |
| --- |
| No. |

61, 62, 63, 64

| Formula 38 |
|---|
| No. |
76 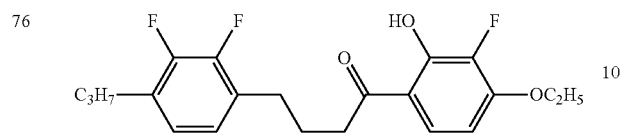
77 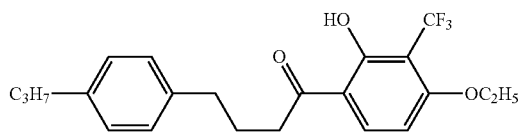
78 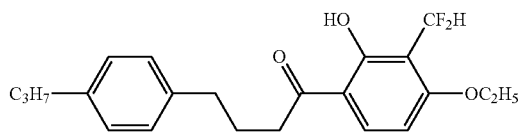
79 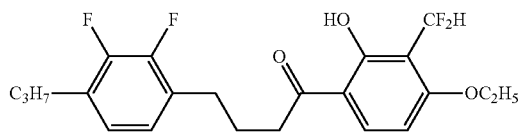
80 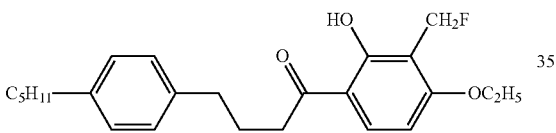
| Formula 39 |
|---|
| No. |
81 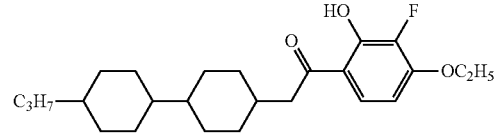
C 137.2 I
$T_{NI}$; 106.6° C., Δ ϵ; −15.30, Δ n; 0.137
82 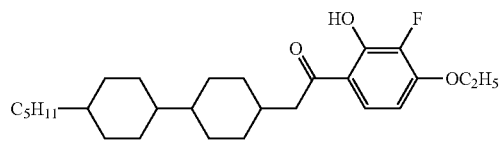
83 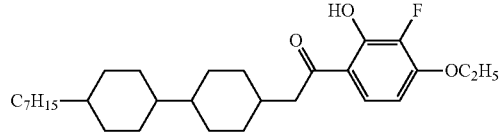
C 129.0 (N 122.0) I
$T_{NI}$; 97.9° C., Δ ϵ; −15.63, Δ n; 0.127
| Formula 39 |
|---|
| No. |
84 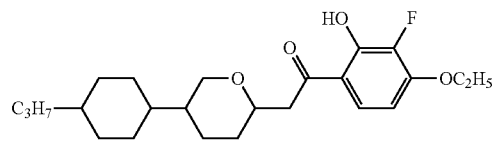
85 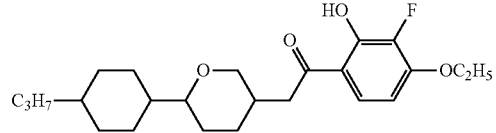
86 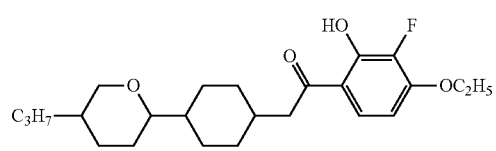
87 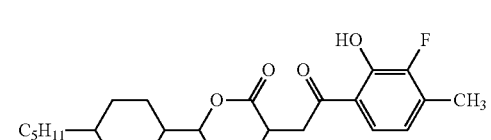
88 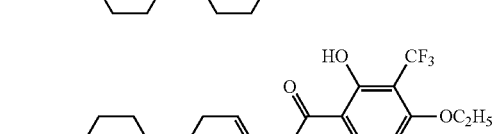
89 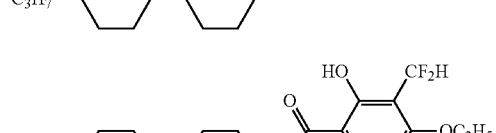
90 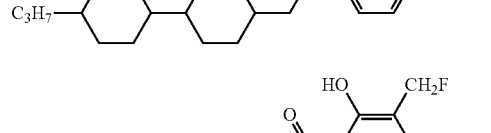
91 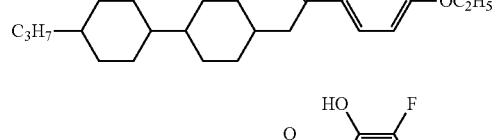
92 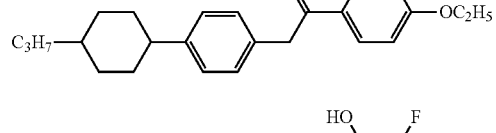
93 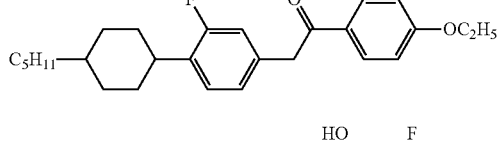
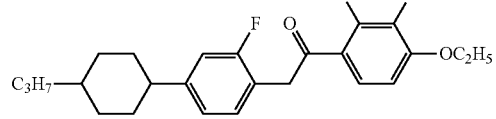

| Formula 39 |
| --- |
| No. |
94 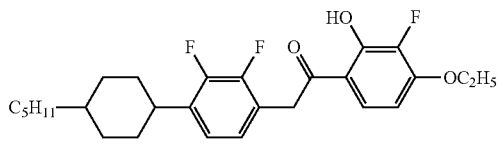
95 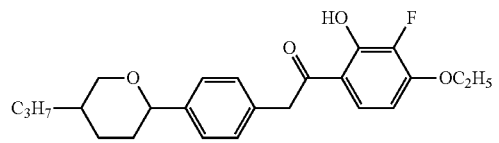
96 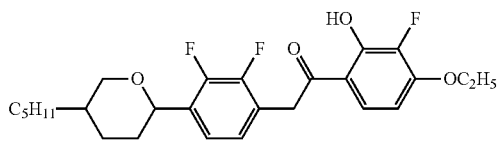
97 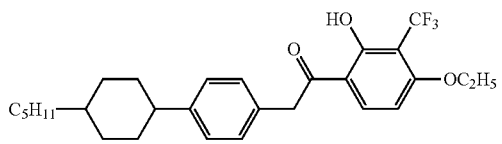
98 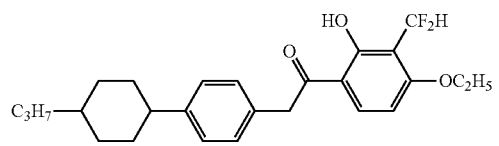
99 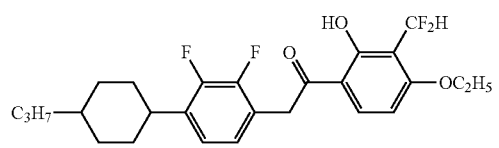
100 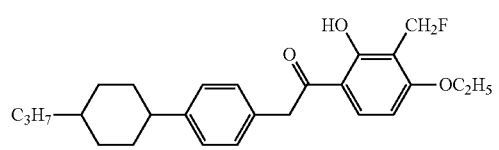
| Formula 40 |
| --- |
| No. |
101 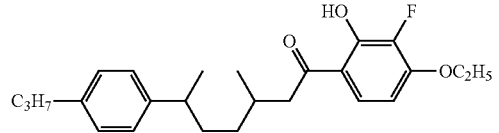
102 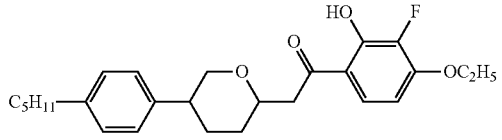
| Formula 40 |
| --- |
| No. |
103 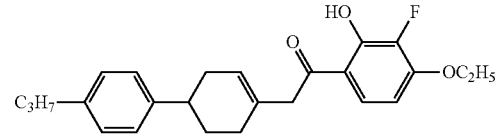
104 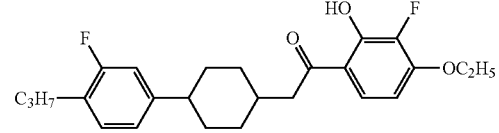
105 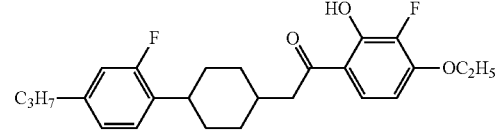
106 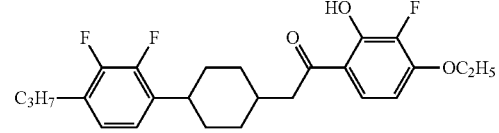
107 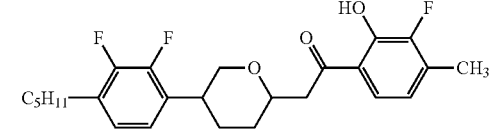
108 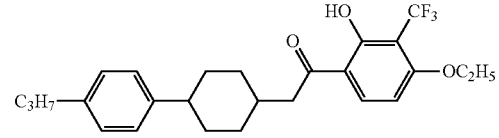
109 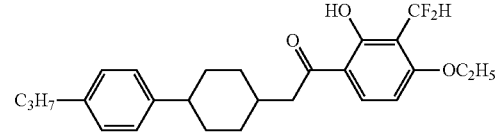
110 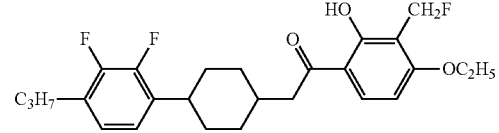
111 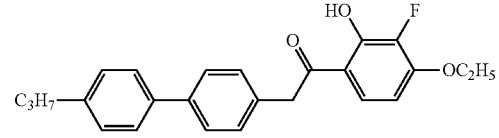
112 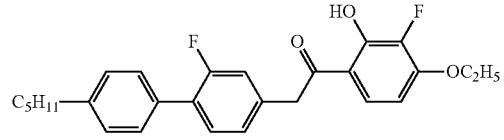

| Formula 40 | |
|---|---|
| No. | |
| 113 | 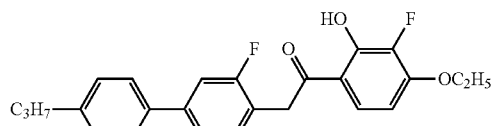 |
| 114 | 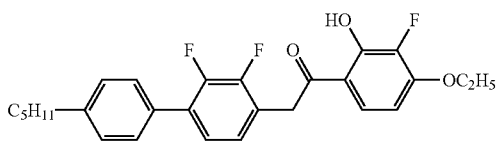 |
| 115 | 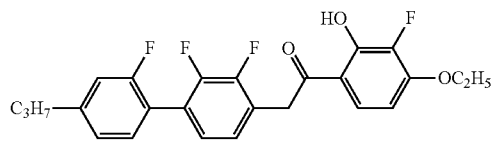 |
| 116 | 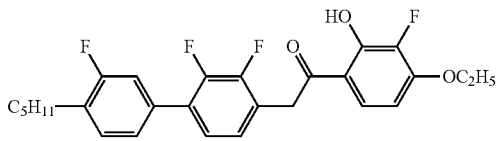 |
| Formula 40 | |
|---|---|
| No. | |
| 117 | 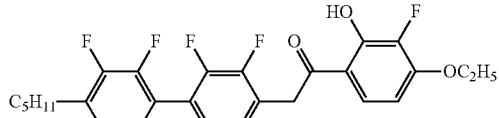 |
| 118 | 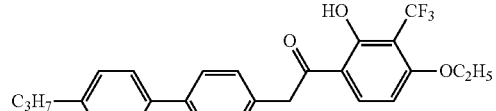 |
| 119 | 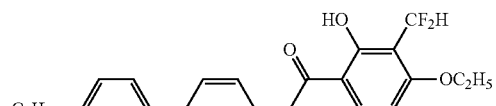 |
| 120 | 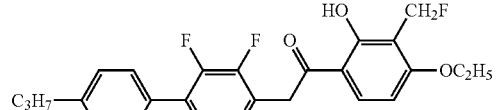 |
| Formula 41 | |
|---|---|
| No. | |
| 121 | 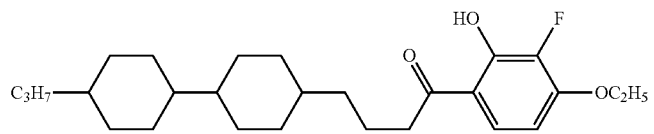 |
C 99.3 C 147.8 N 158.7 I
$T_{NI}$; 144.6° C., Δ ε; −14.50, Δ n: 0.147
| | |
|---|---|
| 122 | 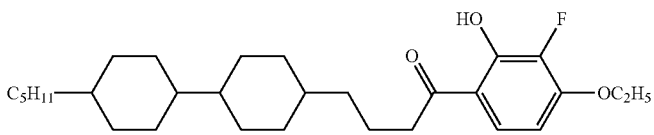 |
| 123 | 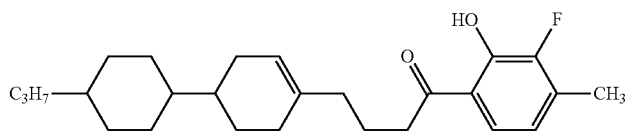 |
| 124 | 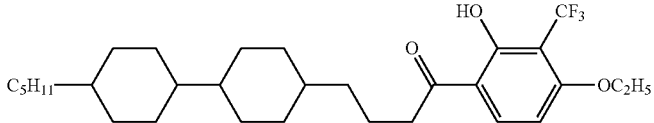 |
| 125 | 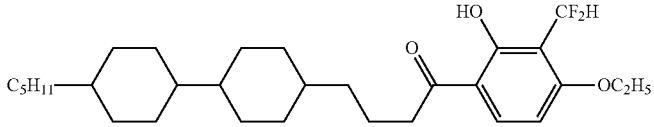 |

Formula 41
No.
126
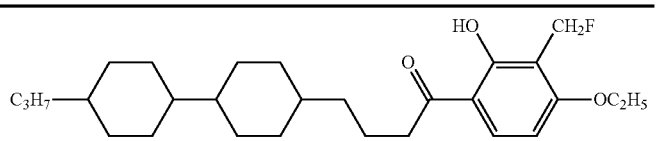
127
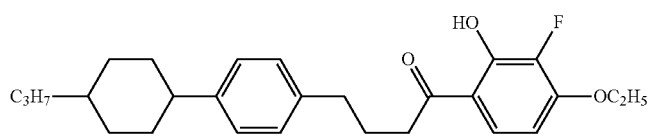
128
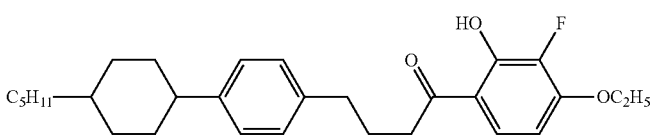
129
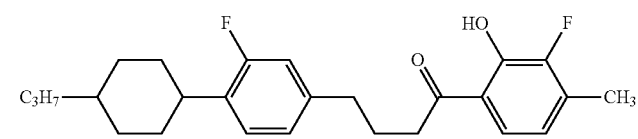
130
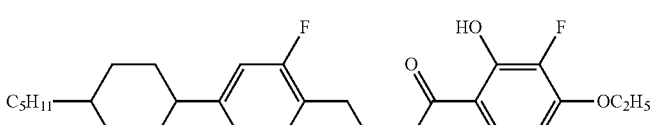
131
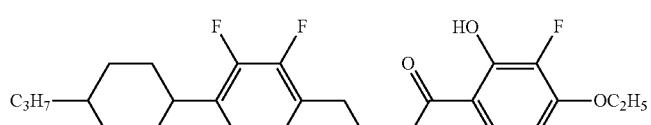
132
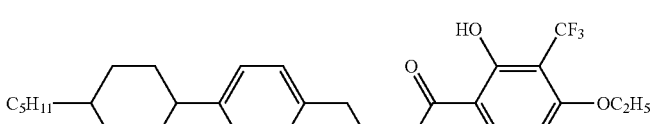
133
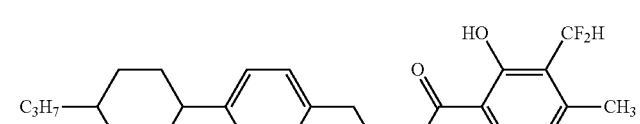
134
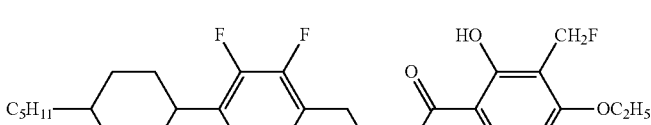
135
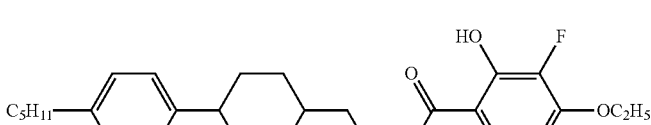
136
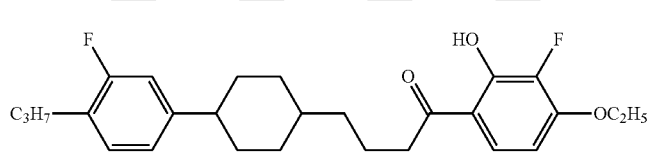

Formula 41
| No. | |
|---|---|
| 137 | 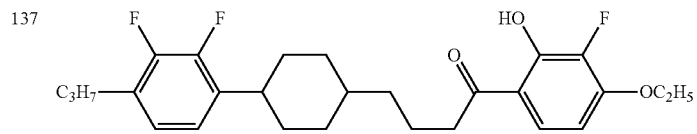 |
| 138 | 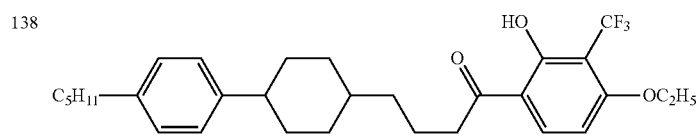 |
| 139 | 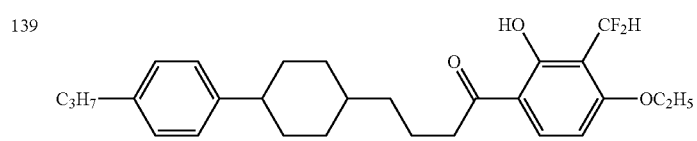 |
| 140 | 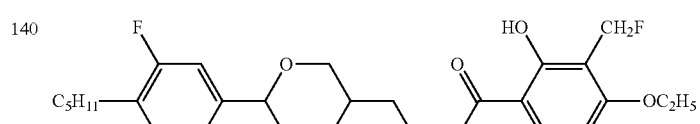 |
Formula 42
| No. | |
|---|---|
| 141 | 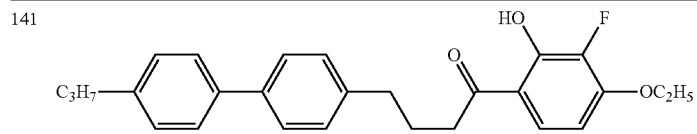 |
| 142 | 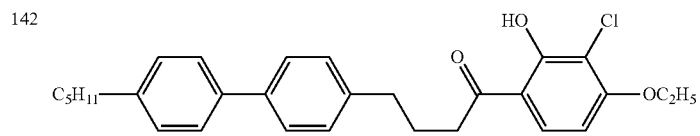 |
| 143 | 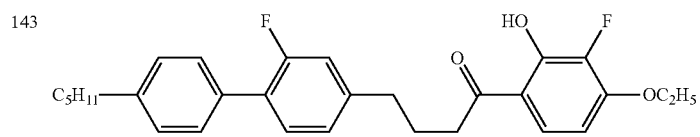 |
| 144 | 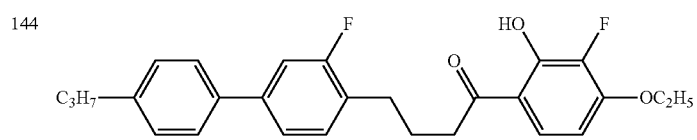 |
| 145 | 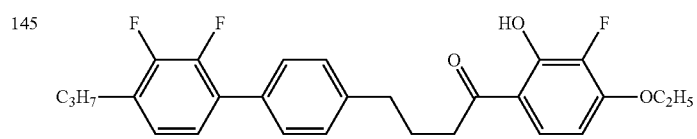 |
| 146 | 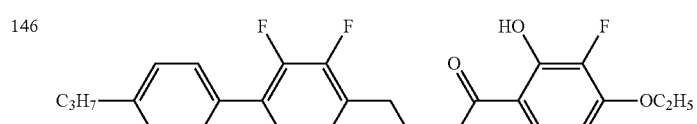 |

| Formula 42 |
|---|
| No. |
147
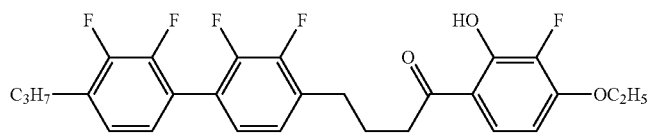
148
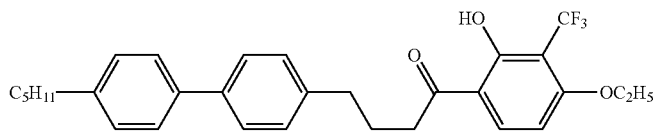
149
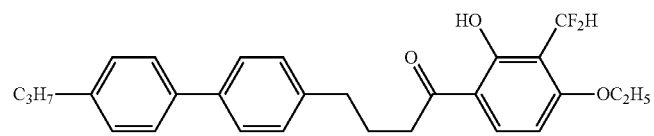
150
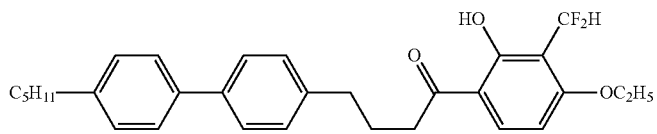
151
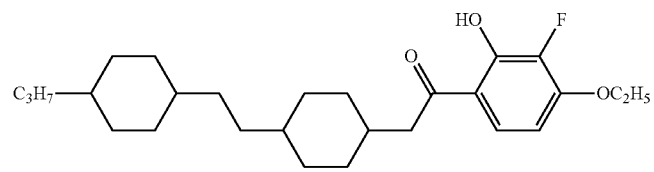
152
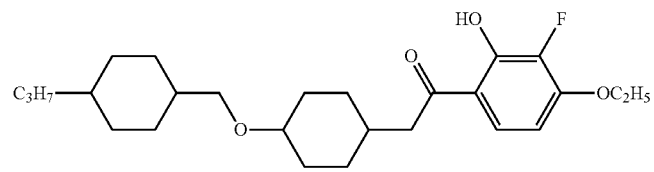
153
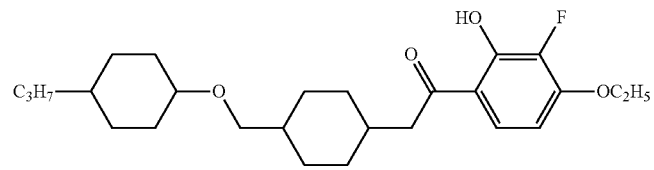
154
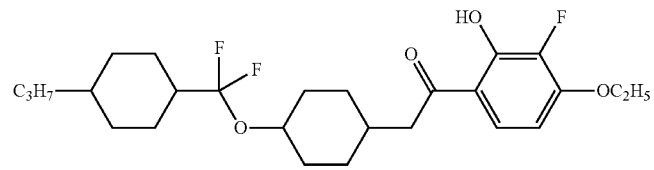
155
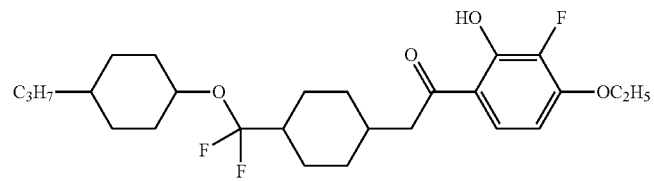

Formula 42
| No. | |
|---|---|
| 156 | 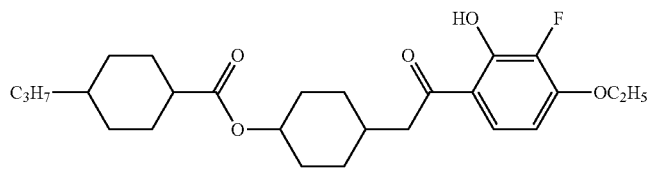 |
| 157 | 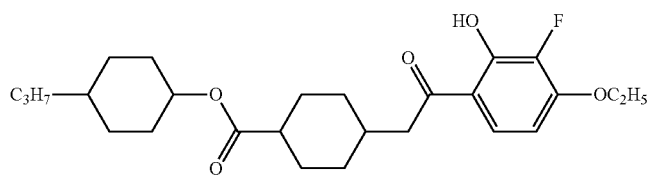 |
| 158 | 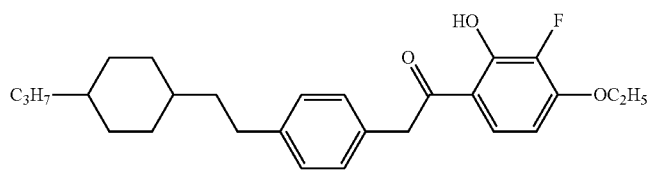 |
| 159 | 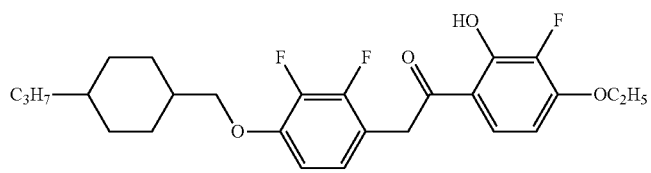 |
| 160 | 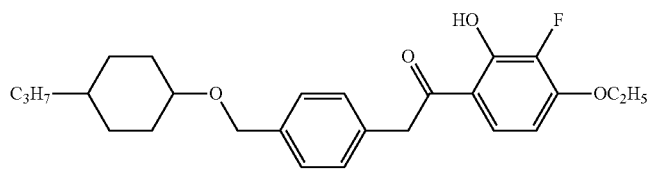 |
Formula 43
| No. | |
|---|---|
| 161 | 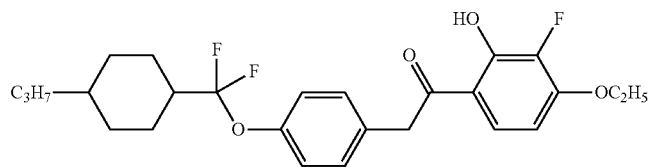 |
| 162 | 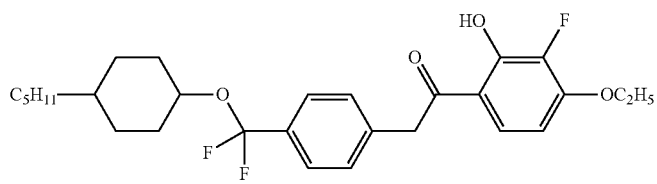 |

| Formula 43 |
|---|
| No. |
163 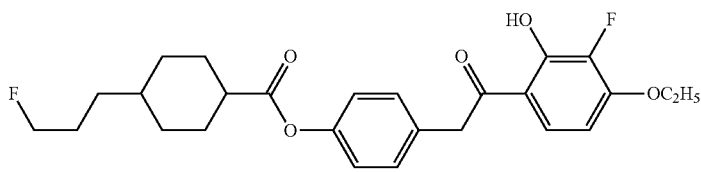 [SMILES: CCOc1ccc(C(=O)Cc2ccc(OC(=O)C3CCC(CCCF)CC3)cc2)c(O)c1F]
164 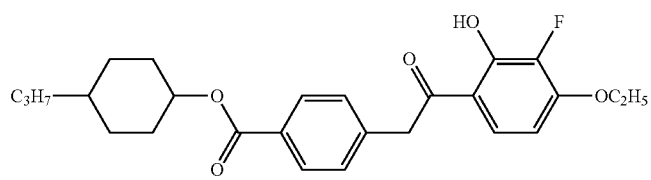
165 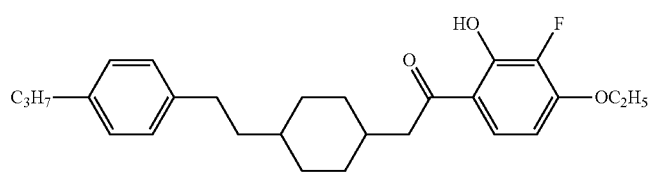
166 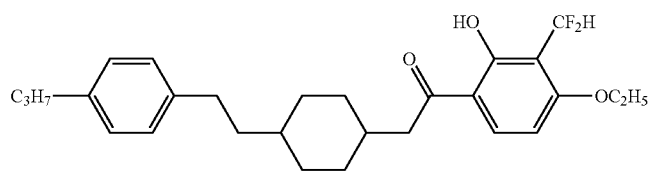
167 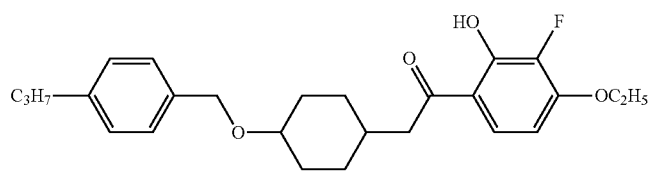
168 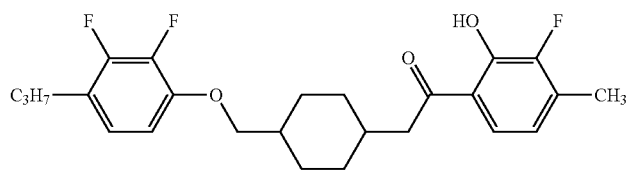
169 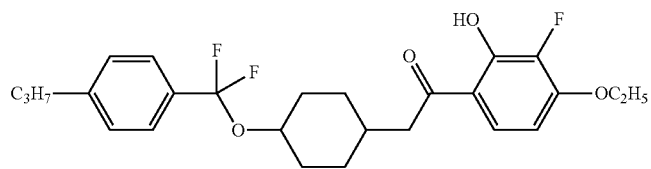
170 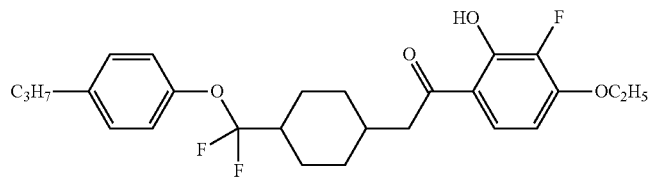

-continued
Formula 43
No.
171 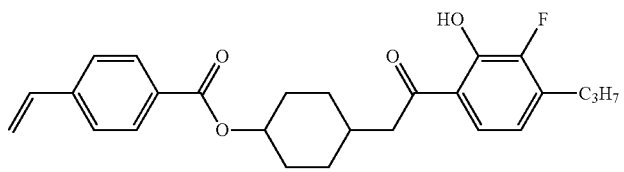
172 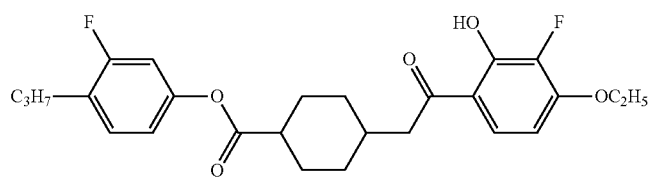
173 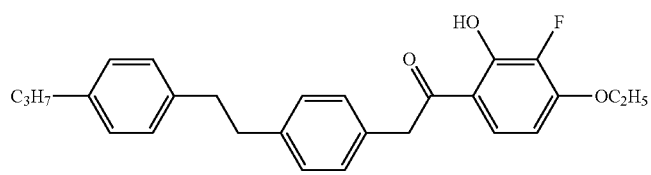
174 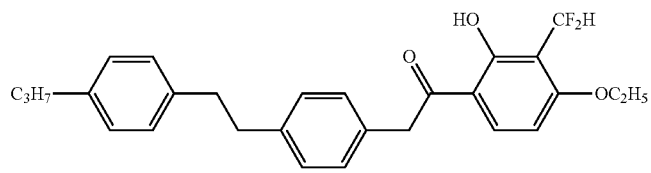
175 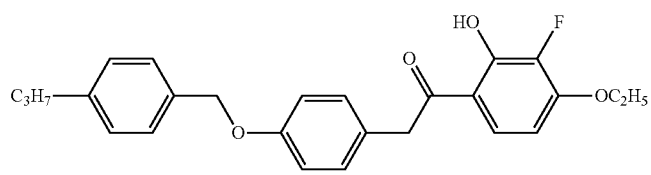
176 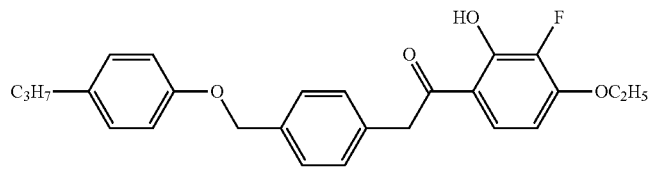
177 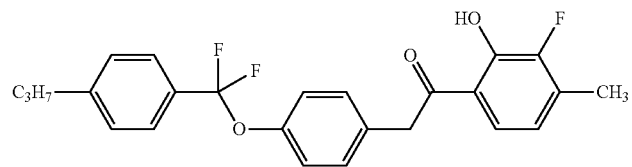
178 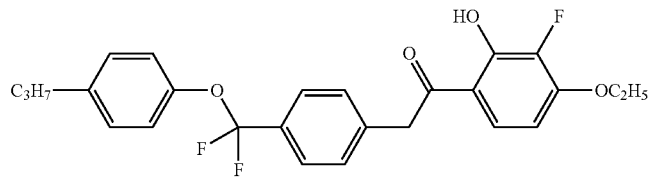

| Formula 43 |
| --- |
| No. |
| 179 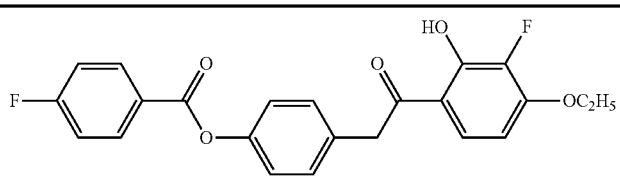 |
| 180 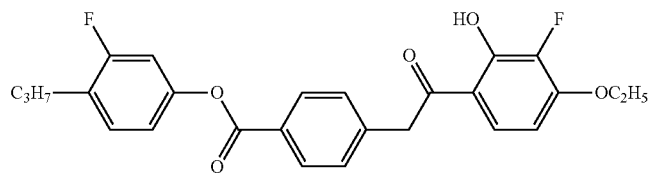 |
| Formula 44 |
| --- |
| No. |
| 181 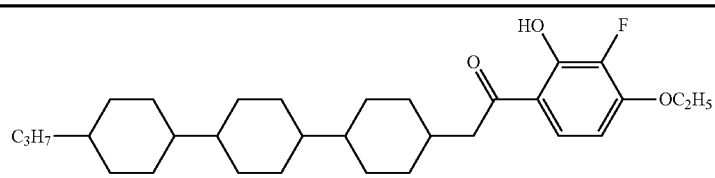 |
| 182 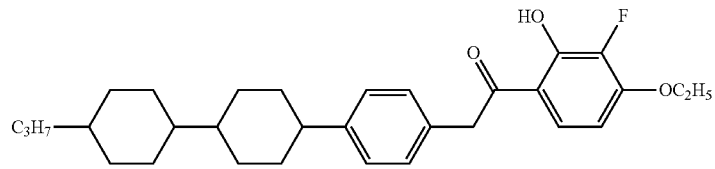 |
| 183 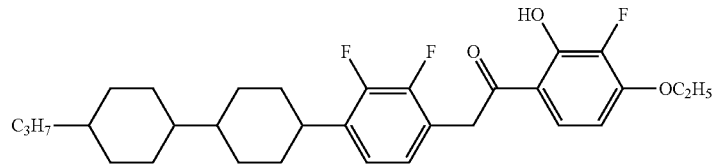 |
| 184 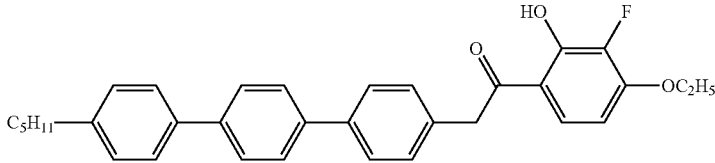 |
| 185 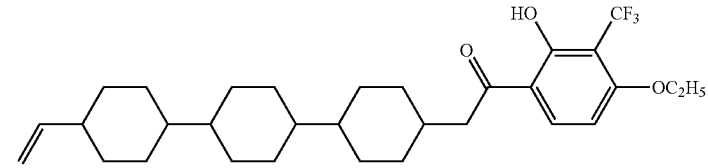 [SMILES: C=CC1CCC(C2CCC(C3CCC(CC(=O)c4ccc(OCC)c(C(F)(F)F)c4O)CC3)CC2)CC1] |
| 186 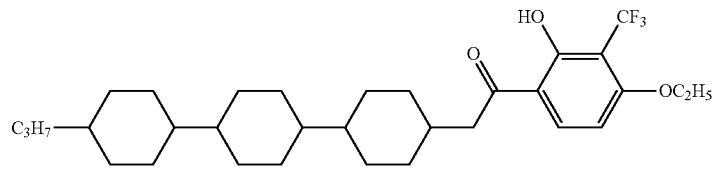 |

| Formula 44 |
|---|
| No. |
| 187 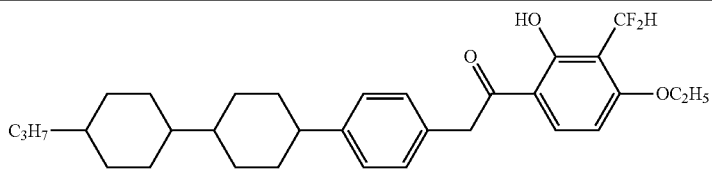 |
| 188 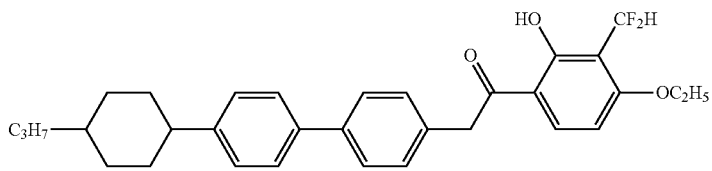 |
| 189 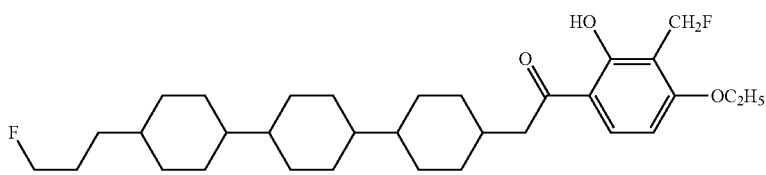 |
| 190 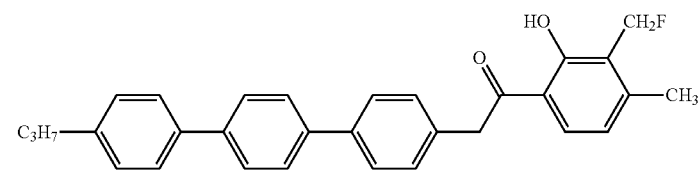 |
| Formula 45 |
|---|
| No. |
| 191 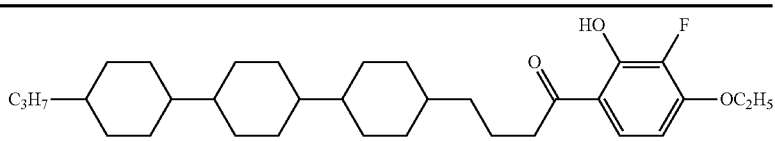 |
| 192 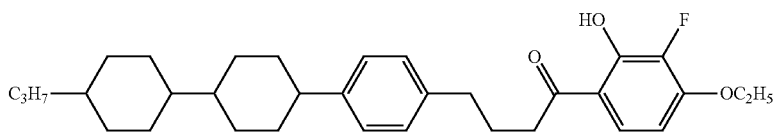 |
| 193 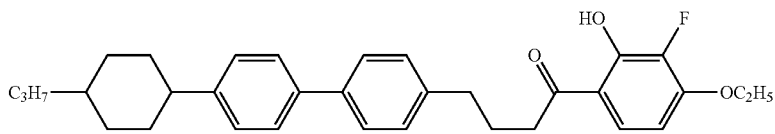 |
| 194 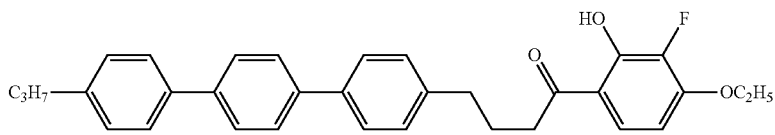 |
| 195 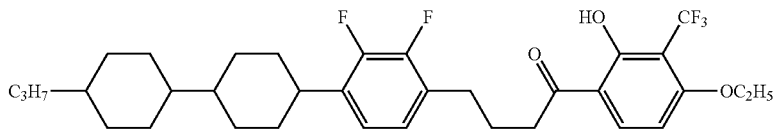 |

| Formula 45 |
|---|
| No. |
| 196 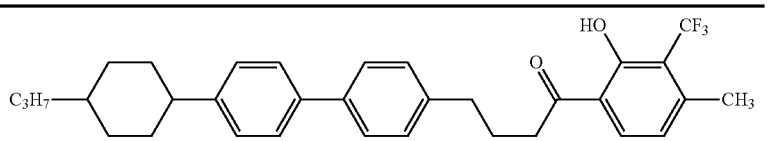 |
| 197 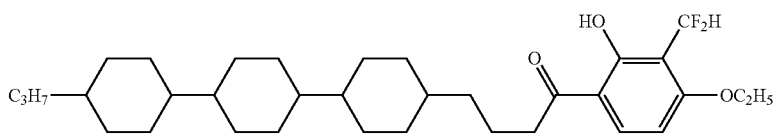 |
| 198 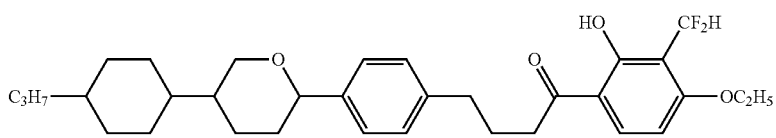 |
| 199 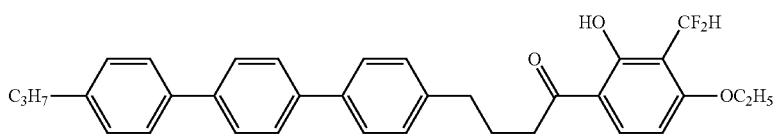 |
| 200 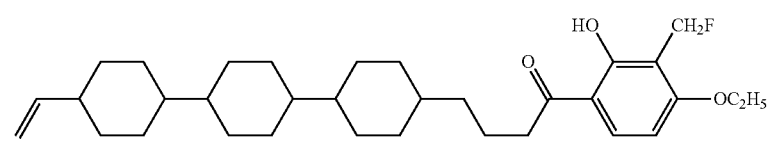 |
| Formula 46 |
|---|
| No. |
| 201 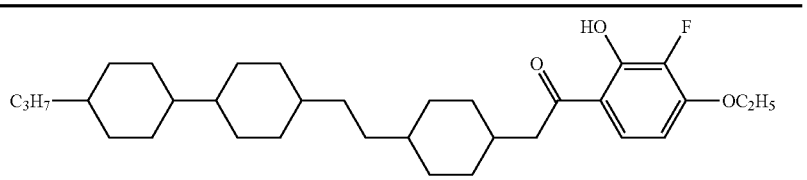 |
| 202 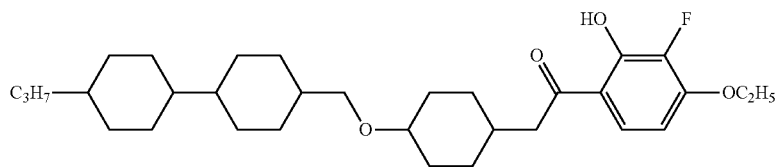 |
| 203 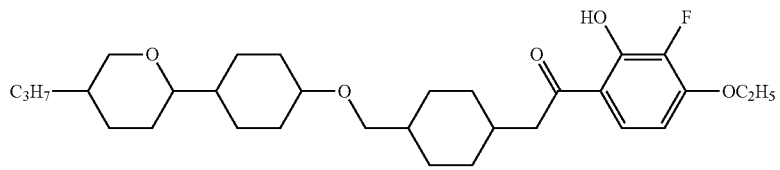 |
| 204 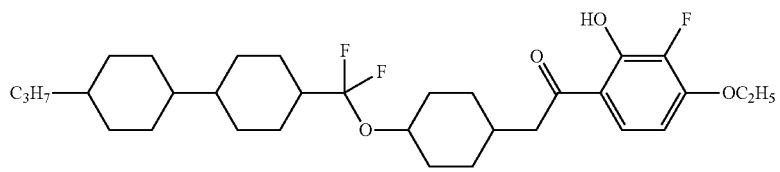 |

| Formula 46 |
|---|
| No. |
| 205 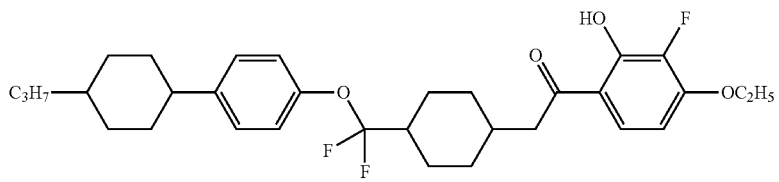 |
| 206 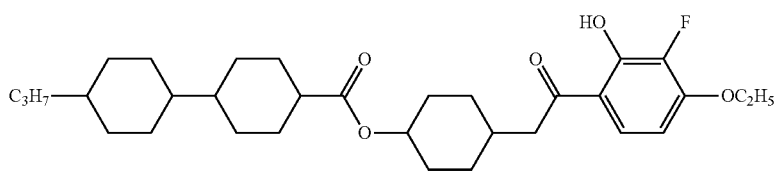 |
| 207 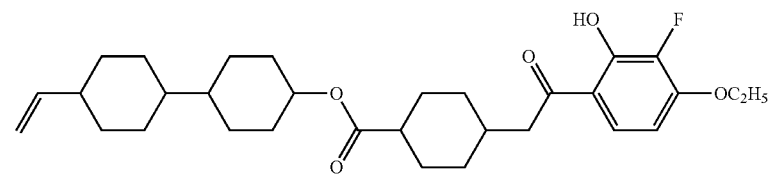 [SMILES: C=CC1CCC(C2CCC(OC(=O)C3CCC(CC(=O)c4ccc(OCC)c(F)c4O)CC3)CC2)CC1] |
| 208 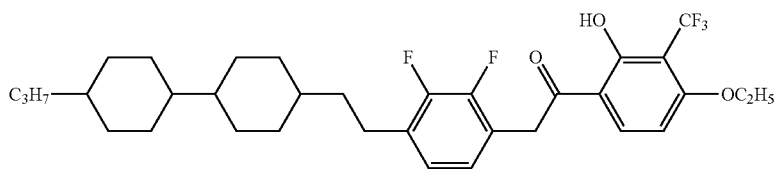 |
| 209 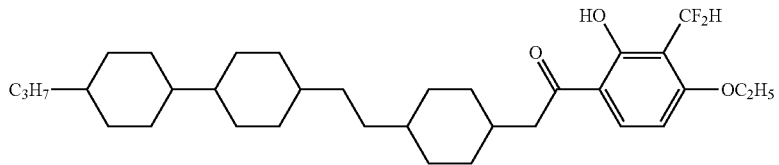 |
| 210 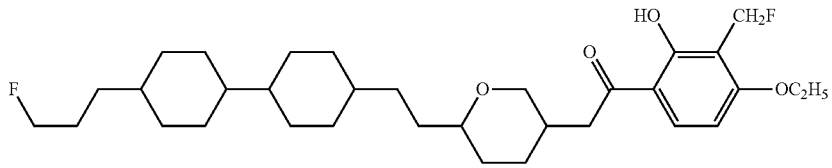 |
| Formula 47 |
|---|
| No. |
| 211 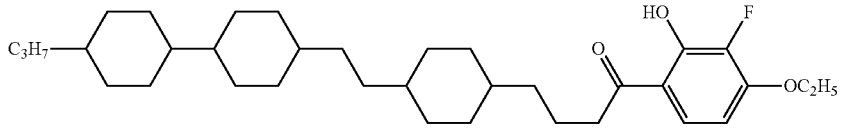 |
| 212 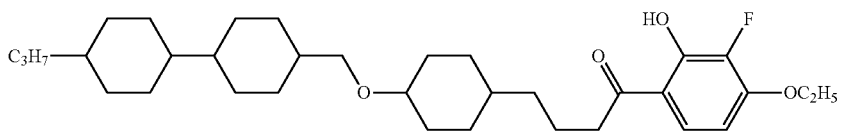 |

-continued

Formula 47

No.

213 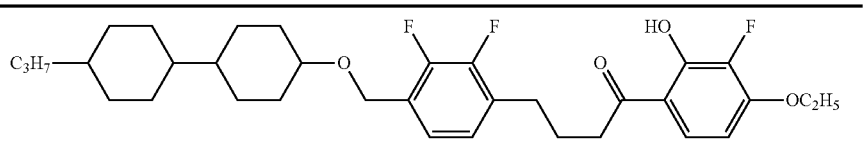

214 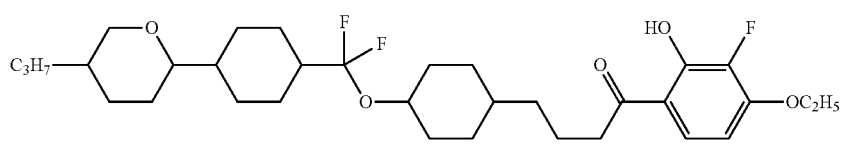

215 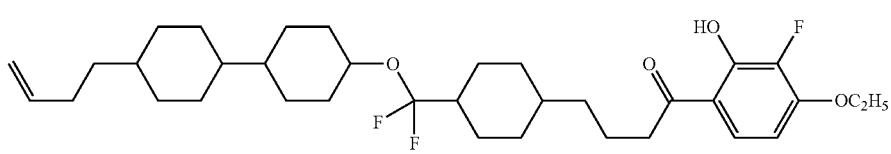 [SMILES: C=CCCC1CCC(C2CCC(OC(F)(F)C3CCC(CCCC(=O)c4ccc(OCC)c(F)c4O)CC3)CC2)CC1]

216 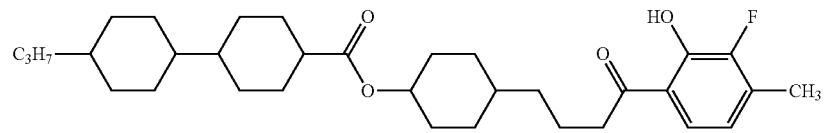

217 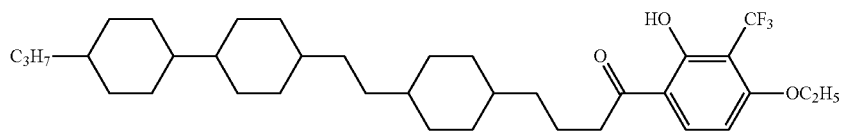

218 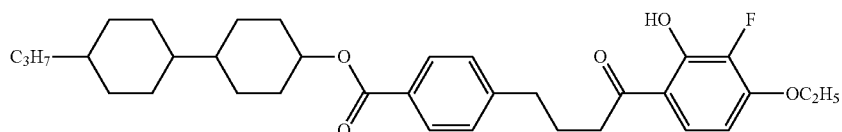

219 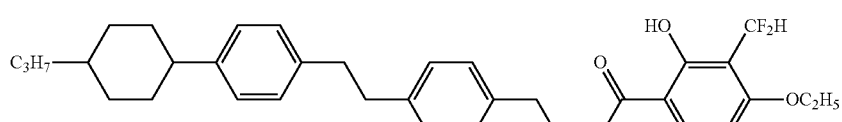

220 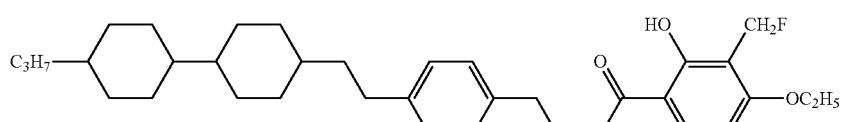

Although the invention has been described and illustrated with a certain degree of particularity, it is understood that the disclosure has been made only by way of example, and that numerous changes in the conditions and order of steps can be resorted to by those skilled in the art without departing from the spirit and scope of the invention.

INDUSTRIAL APPLICABILITY

A liquid crystal compound of the invention has a high stability to heat, light and so forth, a high clearing point and a high maximum temperature, a low minimum temperature of a liquid crystal phase, a small viscosity, a suitable optical anisotropy, a large negative dielectric anisotropy, a suitable elastic constant and an excellent solubility in other liquid crystal compounds. A liquid crystal composition of the invention contains the compound, and has a high maximum temperature of a nematic phase, a low minimum temperature of the nematic phase, a small viscosity, a suitable optical anisotropy, a large negative dielectric anisotropy and a suitable elastic constant. The composition has a suitable balance regarding at least two of physical properties. A liquid crystal display device of the invention includes the composition, and has a wide temperature range in which the device can be used, a short response time, a large voltage holding ratio, a large contrast ratio and a long service life. Accordingly, the device can be widely utilized for a display of a personal computer, a television and so forth.

What is claimed is:

1. A compound represented by formula (1):

Formula 1

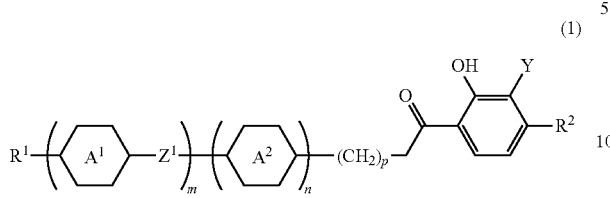

wherein, in formula (1), $R^1$ and $R^2$ are independently alkyl having 1 to 10 carbons, and in the alkyl, at least one of —$CH_2$— may be replaced by —O—, at least one of —$(CH_2)_2$— may be replaced by —CH=CH—, and at least one of hydrogen may be replaced by halogen;

ring $A^1$ and ring $A^2$ are independently 1,4-cyclohexylene or 1,4-phenylene, at least one of —$(CH_2)_2$— constituting 1,4-cyclohexylene may be replaced by —CH=CH—, at least one of Formula 2

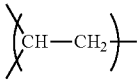

constituting 1,4-cyclohexylene may be replaced by

Formula 3

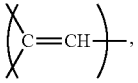

at least one of —$CH_2$— constituting 1,4-cyclohexylene may be replaced by —O— or —CO—, and at least one of hydrogen directly bonded with the rings may be replaced by halogen, —$CF_3$, —$CF_2H$ or —$CH_2F$;

$Z^1$ is a single bond, —$(CH_2)_2$—, —$CH_2O$—, —$OCH_2$—, —$CF_2O$—, —$OCF_2$—, —COO— or —OCO—;

Y is fluorine, chlorine, —$CF_3$, —$CF_2H$ or —$CH_2F$; and m, n and p are independently 0, 1 or 2, and a sum (m+n) of m and n is 0, 1 or 2.

2. The compound according to claim 1, wherein, in formula (1), $R^1$ and $R^2$ are independently alkyl having 1 to 10 carbons, alkenyl having 2 to 10 carbons, alkoxy having 1 to 9 carbons, alkoxyalkyl having 2 to 9 carbons or alkenyloxy having 2 to 9 carbons, and in the groups, at least one of hydrogen may be replaced by halogen; and ring $A^1$ and ring $A^2$ independently 1,4-cyclohexylene, 1,4-cyclohexenylene, tetrahydropyran-2,5-diyl, 1,4-phenylene, 2-fluoro-1,4-phenylene or 2,3-difluoro-1,4-phenylene.

3. The compound according to claim 2, wherein, in formula (1), Y is fluorine.

4. The compound according to claim 2, wherein, in formula (1), a relational expression: m=n=1 applies.

5. The compound according to claim 2, wherein, in formula (1), a relational expression: m=0 and n=1 applies.

6. The compound according to claim 2, wherein, in formula (1), a relational expression m=n=p=0 applies.

7. A liquid crystal composition, containing at least one kind of the compound according to claim 1.

8. The liquid crystal composition according to claim 7, further containing at least one kind selected from an optically active compound and a polymerizable compound.

9. The liquid crystal composition according to claim 7, further containing at least one kind selected from an antioxidant and an ultraviolet absorber.

10. A liquid crystal display device including the liquid crystal composition according to claim 7.

* * * * *